US010688186B2

(12) United States Patent
Shailubhai

(10) Patent No.: US 10,688,186 B2
(45) Date of Patent: Jun. 23, 2020

(54) ANTI-CD3 ANTIBODY FORMULATIONS

(71) Applicant: Tiziana Life Sciences PLC, London (GB)

(72) Inventor: Kunwar Shailubhai, Audubon, PA (US)

(73) Assignee: Tiziana Life Sciences PLC, London (GB)

( * ) Notice: Subject to any disclaimer, the term of this patent is extended or adjusted under 35 U.S.C. 154(b) by 52 days.

(21) Appl. No.: 15/690,192

(22) Filed: Aug. 29, 2017

(65) Prior Publication Data

US 2018/0177880 A1 Jun. 28, 2018

Related U.S. Application Data

(60) Provisional application No. 62/380,652, filed on Aug. 29, 2016.

(51) Int. Cl.
| | |
|---|---|
| *A61K 39/395* | (2006.01) |
| *A61K 47/20* | (2006.01) |
| *C07K 16/28* | (2006.01) |
| *A61P 1/16* | (2006.01) |
| *A61P 37/06* | (2006.01) |
| *A61K 9/48* | (2006.01) |
| *A61K 45/06* | (2006.01) |
| *A61K 47/02* | (2006.01) |
| *A61K 47/12* | (2006.01) |
| *A61K 47/18* | (2017.01) |
| *A61K 47/26* | (2006.01) |
| *A61K 39/00* | (2006.01) |

(52) U.S. Cl.
CPC .............. *A61K 47/20* (2013.01); *A61K 9/485* (2013.01); *A61K 9/4858* (2013.01); *A61K 9/4866* (2013.01); *A61K 9/4891* (2013.01); *A61K 39/3955* (2013.01); *A61K 39/39591* (2013.01); *A61K 45/06* (2013.01); *A61K 47/02* (2013.01); *A61K 47/12* (2013.01); *A61K 47/183* (2013.01); *A61K 47/26* (2013.01); *A61P 1/16* (2018.01); *A61P 37/06* (2018.01); *C07K 16/2809* (2013.01); *A61K 2039/505* (2013.01); *A61K 2039/54* (2013.01); *A61K 2039/545* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 2003/0235583 A1 | 12/2003 | Sturis et al. | |
| 2004/0037826 A1 | 2/2004 | Michelsen et al. | |
| 2007/0065437 A1* | 3/2007 | Elson | A61K 9/0019 424/144.1 |
| 2011/0158987 A1* | 6/2011 | Adler | A61K 9/0019 424/133.1 |

FOREIGN PATENT DOCUMENTS

| | | |
|---|---|---|
| WO | WO 2007/033230 A2 | 3/2007 |
| WO | WO 2007/113648 A2 | 10/2007 |
| WO | WO 2010/148337 A1 | 12/2010 |
| WO | WO 2011/080209 A2 | 7/2011 |
| WO | WO 2018/044948 A1 | 3/2018 |

OTHER PUBLICATIONS

Hussan et al. Journal of Pharmacy, vol. 2, p. 5-11, 2012 (Year: 2012).*
Baldrick P. "Pharmaceutical excipient development: the need for preclinical guidance." Regul. Toxicol Pharmacol. 32(2):2 W-8 (2000).
Charman WN "Lipids, lipophilic drugs, and oral drug delivery—some emerging concepts." J Pharm Sci. 89(8):967-78 (2000).
Davies et al. "Antibody-Antigen Complexes", Annual Rev Biochem, vol. 59, p. 439-473 (1990).
Malmqvist, M. "Biospecific interaction analysis using biosensor technology", Nature, vol. 361, p. 186-187 (1993).
Powell et al. "Compendium of excipients for parenteral formulations" PDA J Pharm Sci Technol. 52:238-311 (1998).
Wang W. "Lyophilization and development of solid protein pharmaceuticals." Int. J. Pharm. 203: 1-60 (2000).
Baldrick P. "Pharmaceutical excipient development: the need for preclinical guidance." Regul. Toxicol Pharmacol. 32(2):210-8 (2000).
Charman W. "Lipids, lipophilic drugs, and oral drug delivery—some emerging concepts." J Pharm Sci. 89(8):967-78 (2000).
Davies et al., "Antibody-Antigen Complexes", Annual Rev Biochem 59:439-473 (1990).
International Search Report issued for Application PCT/US2017/049211, dated Jan. 10, 2018.
Kang J. et al. "Rapid Formulation Development for Monoclonal Antibodies", BioProcess International, 14(4), 4 pages (2016).
Malmqvist M. "Biosepcific interaction analysis using biosensor technology", Nature 361:186-187 (1993).
Medi M. B. et al. "Excipient selection in biologics and vaccines formulation development", European Pharmaceutical Review 19(1): 16-20 (2014).
Wang W. "Lyophilization and development of solid protein pharmaceuticals." Int. J. Pharm. 203(1-2):1-60 (2000).

* cited by examiner

*Primary Examiner* — Yunsoo Kim
(74) *Attorney, Agent, or Firm* — Cooley LLP; Ivor R. Elrifi; Cynthia A. Kozakiewicz

(57) ABSTRACT

This invention relates to therapeutic, diagnostic and/or prophylactic formulations and dosages and dosing regimens of anti-CD3 antibodies, as well as to methods for using such formulations and dosages and dosing regimens.

33 Claims, 36 Drawing Sheets

Specification includes a Sequence Listing.

10% Tre-    10% Tre-Met    10% Tre-Arg    Sod. Asc    20%Tre-EDTA

T14 at 4°C    T14 at 50°C

Lane 1=Markers
Lane 2= T0 (Control)
Lane 3=T14-50C (Control)
Lane 4=T14-4C (Control)
Lane 5= T0 (Tre-Met)
Lane 6=T14-50C (Tre-Met)
Lane 7=T14-4C (Tre-Met)
Lane 8= T0 (Tre-Met-EDTA)
Lane 9=T14-50C (Tre-Met-EDTA)
Lane 10=T14-4C (Tre-Met-EDTA)
Lane 11= Buffer
Lane 12 =Ref Std

A. T0

B. T14 at 4°C

C. T14 at 50 °C a) Full Scale b) Expanded Scale

C. Overlay

Figure A: showing the overlay of chromatogram for NI0401 lead formulations vs control formulation: T14 kept at 50°C

Figure B: showing the overlay (enlarged) of chromatogram for NI0401 lead formulations vs control formulation: T14 Lyo kept at 50°C

SEQUENCE LISTING

```
<160> NUMBER OF SEQ ID NOS: 11

<210> SEQ ID NO 1
<211> LENGTH: 5
<212> TYPE: PRT
<213> ORGANISM: Artificial Sequence
<220> FEATURE:
<223> OTHER INFORMATION: anti-CD3 CDRH1

<400> SEQUENCE: 1

Gly Tyr Gly Met His
1               5

<210> SEQ ID NO 2

<400> SEQUENCE: 2

000

<210> SEQ ID NO 3
<211> LENGTH: 17
<212> TYPE: PRT
<213> ORGANISM: Artificial Sequence
<220> FEATURE:
<223> OTHER INFORMATION: anti-CD3 CHRH2

<400> SEQUENCE: 3

Val Ile Trp Tyr Asp Gly Ser Lys Lys Tyr Tyr Val Asp Ser Val Lys
1               5                   10                  15

Gly

<210> SEQ ID NO 4
<211> LENGTH: 9
<212> TYPE: PRT
<213> ORGANISM: Artificial Sequence
<220> FEATURE:
<223> OTHER INFORMATION: anti-CD3 CHRH3

<400> SEQUENCE: 4

Gln Met Gly Tyr Trp His Phe Asp Leu
1               5

<210> SEQ ID NO 5
<211> LENGTH: 11
<212> TYPE: PRT
<213> ORGANISM: Artificial Sequence
<220> FEATURE:
<223> OTHER INFORMATION: anti-CD3 CDRL1

<400> SEQUENCE: 5

Arg Ala Ser Gln Ser Val Ser Ser Tyr Leu Ala
1               5                   10

<210> SEQ ID NO 6
<211> LENGTH: 7
<212> TYPE: PRT
<213> ORGANISM: Artificial Sequence
<220> FEATURE:
<223> OTHER INFORMATION: anti-CD3 CDRL2

<400> SEQUENCE: 6

Asp Ala Ser Asn Arg Ala Thr
1               5

<210> SEQ ID NO 7
<211> LENGTH: 10
```

```
<212> TYPE: PRT
<213> ORGANISM: Artificial Sequence
<220> FEATURE:
<223> OTHER INFORMATION: anti-CD3 CDRL3

<400> SEQUENCE: 7

Gln Gln Arg Ser Asn Trp Pro Pro Leu Thr
1               5                   10

<210> SEQ ID NO 8
<211> LENGTH: 118
<212> TYPE: PRT
<213> ORGANISM: Artificial Sequence
<220> FEATURE:
<223> OTHER INFORMATION: anti-CD3 variable heavy chain

<400> SEQUENCE: 8

Gln Val Gln Leu Val Glu Ser Gly Gly Val Val Gln Pro Gly Arg
1               5                   10                  15

Ser Leu Arg Leu Ser Cys Ala Ala Ser Gly Phe Lys Phe Ser Gly Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Met Gly Tyr Trp His Phe Asp Leu Trp Gly Arg Gly Thr
            100                 105                 110

Leu Val Thr Val Ser Ser
            115

<210> SEQ ID NO 9
<211> LENGTH: 108
<212> TYPE: PRT
<213> ORGANISM: Artificial Sequence
<220> FEATURE:
<223> OTHER INFORMATION: anti-CD3 variable light chain

<400> SEQUENCE: 9

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Leu Thr Phe Gly Gly Gly Thr Lys Val Glu Ile Lys
            100                 105

<210> SEQ ID NO 10
<211> LENGTH: 448
<212> TYPE: PRT
```

<213> ORGANISM: Artificial Sequence
<220> FEATURE:
<223> OTHER INFORMATION: anti-CD3 heavy chain

<400> SEQUENCE: 10

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Lys Phe Ser Gly Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Met Gly Tyr Trp His Phe Asp Leu Trp Gly Arg Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Glu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
```

-continued

```
                  385              390              395              400
Ser Asp Gly Ser Phe Phe Leu Tyr Ser Lys Leu Thr Val Asp Lys Ser
                405              410              415

Arg Trp Gln Gln Gly Asn Val Phe Ser Cys Ser Val Met His Glu Ala
                420              425              430

Leu His Asn His Tyr Thr Gln Lys Ser Leu Ser Leu Ser Pro Gly Lys
                435              440              445

<210> SEQ ID NO 11
<211> LENGTH: 215
<212> TYPE: PRT
<213> ORGANISM: Artificial Sequence
<220> FEATURE:
<223> OTHER INFORMATION: anti-CD3 light chain

<400> SEQUENCE: 11

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
                35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Leu Thr Phe Gly Gly Gly Thr Lys Val Glu Ile Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
        210                 215
```

ANTI-CD3 ANTIBODY FORMULATIONS

RELATED APPLICATIONS

This application claims benefit of, and priority to, U.S. Ser. No. 62/380,652 filed on Aug. 29, 2016; the contents of which are hereby incorporated by reference in its entirety.

FIELD OF THE INVENTION

This invention relates to formulations, dosages, and dosing regimens of anti-CD3 antibodies as well as to methods for use thereof.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: TIZI_013_001US_SeqList_ST25.txt, date recorded: Jan. 18, 2018, file size 9.34 kilobytes).

BACKGROUND OF THE INVENTION

Antibodies to the CD3 epsilon signaling molecule of the T-cell receptor complex have proven to be useful as immunosuppressants and in the treatment of autoimmune disorders. Thus, improved methods of preparing anti-CD3 antibodies, methods of purifying anti-CD3 antibodies and pharmaceutical formulations containing anti-CD3 antibodies would be useful.

SUMMARY OF THE INVENTION

The present disclosure provides formulation, dosages, and dosing regimens for monoclonal antibodies specifically directed against CD3 The formulations of the present disclosure include an anti-CD3 antibody, and these formulations are referred to herein as "anti-CD3 antibody formulations." In some embodiments, the anti-CD3 antibody formulation is an oral formulation.

In various aspects the invention provides a formulation including an anti-CD3 antibody or antigen binding fragment thereof, sodium acetate trihydrate, sodium chloride, polysorbate 80, trehalose, and methionine. Optionally, the formulation further includes EDTA. The formulation is a liquid or a lyophilized powder. The formulation includes a unit does of the anti-CD3 antibody or antigen binding fragment. The unit dose is for example, about 0.1 mg to 10 mg. Preferably the unit dose is 0.5 mg, 2.5 mg or 5.0 mg.

When the formulation is a liquid, the concentration of sodium acetate trihydrate is about 10 mM to 500 mM; the concentration of sodium chloride is about 10 mM to 500 mM; the concentration of polysorbate 80 is about 0.01% to 1% (w/v); the concentration of trehalose is about 5% to 50% (w/v); and the concentration of methionine is about 0.01% to 1% (w/v). When EDTA is include the concentration of EDTA is about 0.01% to 1% (w/v). The pH of the solution is in the range of pH 4 to pH 6. In various aspects the formulation is in an oral dosage form such as a capsule. The capsule is enteric coated. Also included in the invention is a lyophilized powder of the liquid formulation.

In another aspect the invention provide a liquid formulation having a unit dose of about 0.1 mg to 10 mg of an anti-CD3 antibody or antigen binding fragment thereof, 25 mM sodium acetate trihydrate, 125 mM sodium chloride, 0.02% polysorbate 80 (w/v), 20% trehalose (w/v), and 0.1% methionine (w/v). Optionally, the formulation further includes 0.1% EDTA (w/v). The unit dose is 0.5 mg, 2.5 mg or 5.0 mg. The pH of the solution is in the range of pH 4 to pH 6. In various aspects, the formulation is in an oral dosage form such as a capsule. The capsule is enteric coated. Also included in the invention is a lyophilized powder of the liquid formulation.

When the formulation is a lyophized powder the the ratio of anti-CD3 antibody or antigen binding fragment to: polysorbate 80 is about 1:0.01 to 0.1 (w/w); the ratio of anti-CD3 antibody or antigen binding fragment to trehalose is about 1:10 to 50 (w/w); the ratio of anti-CD3 antibody or antigen binding fragment to methionine about 1:0.1 to 0.5 (w/w); the ratio of anti-CD3 antibody or antigen binding fragment to sodium acetate trihydrate is about 1:0.1 to 1.0 (w/w); and the ratio of anti-CD3 antibody or antigen binding fragment to sodium chloride is about 1:0.5 to 2.0 (w/w). When EDTA is included the ratio of anti-CD3 antibody or antigen binding fragment to:EDTA is about 1:0.1 to 0.5 (w/w). In various aspects, the formulation is in an oral dosage form such as a capsule. The capsule is enteric coated.

In another aspect the invention provide a powder formulation having a unit dose of about 0.1 mg to 10 mg of an anti-CD3 antibody or antigen binding fragment thereof and about 0.58 mg of sodium acetate trihydrate, 1.25 mg sodium chloride, 0.034 mg polysorbate 80, 34 mg trehalose and 0.17 mg methionine per 1 mg of anti-CD3 antibody or antigen binding fragment thereof. Optionally, the powder formulation further includes 0.17 mg EDTA per 1 mg of anti-CD3 antibody or antigen binding fragment thereof. The unit dose is 0.5 mg, 2.5 mg or 5.0 mg.

Also included in the invention is an enteric coated oral capsule containing any of the formulations of the invention.

In a further aspect, the invention provides an enteric coated oral capsule containing an anti-CD3 antibody lyophilized formulation having a unit dose of about 0.1 mg to 10 mg of an anti-CD3 antibody or antigen binding fragment thereof and about 0.58 mg of sodium acetate trihydrate, 1.25 mg sodium chloride, 0.034 mg polysorbate 80, 34 mg trehalose and 0.17 mg methionine per 1 mg of anti-CD3 antibody or antigen binding fragment thereof. Optionally, anti-CD3 antibody lyophilized formulation further includes 0.17 mg EDTA per 1 mg of anti-CD3 antibody or antigen binding fragment thereof. The unit dose is 0.5 mg, 2.5 mg or 5.0 mg.

In yet another aspect, the invention provides n enteric coated oral capsule containing an anti-CD3 antibody liquid formulation having a unit dose of about 0.1 mg to 10 mg of an anti-CD3 antibody or antigen binding fragment thereof, 25 mM sodium acetate trihydrate, 125 mM sodium chloride, 0.02% polysorbate 80 (w/v), 20% trehalose (w/v), and 0.1% methionine (w/v). Optionally, the anti-CD3 antibody liquid formulation further includes 0.1% EDTA. The unit dose is 0.5 mg, 2.5 mg or 5.0 mg.

The anti-CD3 antibody according the formulations of the invention -CD3 antibody has for example, a heavy chain complementarity determining region 1 (CDRH1) comprising the amino acid sequence GYGMH (SEQ ID NO: 1), a heavy chain complementarity determining region 2 (CDRH2) comprising the amino acid sequence VIWYDG-SKKYYVDSVKG (SEQ ID NO: 3), a heavy chain complementarity determining region 3 (CDRH3) comprising the amino acid sequence QMGYWHFDL (SEQ ID NO: 4), a light chain complementarity determining region 1 (CDRL1) comprising the amino acid sequence RASQSVSSYLA (SEQ ID NO: 5), a light chain complementarity determining region 2 (CDRL2) comprising the amino acid sequence DASNRAT (SEQ ID NO: 6), and a light chain complementarity determining region 3 (CDRL3) comprising the amino acid sequence QQRSNWPPLT (SEQ ID NO: 7).

Alternatively the -CD3 antibody has a variable heavy chain amino acid sequence comprising the amino acid sequence of SEQ ID NO: 8 and a variable light chain amino acid sequence comprising the amino acid sequence of SEQ ID NO: 9. In other aspects the anti-CD3 antibody has a heavy chain amino acid sequence comprising the amino acid sequence of SEQ ID NO: 10 and a light chain amino acid sequence comprising the amino acid sequence of SEQ ID NO: 11.

In various aspects the formulation of the invention has at least one additional active agent. The additional active agent includes for example, an NF-kB inhibitor, a GLP-1 or a beta cell resting compound, mesalamine or another 5-ASA drug, pentoxifylline, ursodeoxycholic acid, a PPARγ agonist, All Trans Retinoic Acid (ATRA), DPP-4 (gliptins-sitagliptin), a fatty acid synthesis inhibitor (e.g., cerulenin, quercetin, C7, apigenin, AICAR), a FXR agonist (e.g., bile salt activators, chenodeoxycholic acid, Obeticholic acid (OIBA, Ocaliva), fexaramine, cafestol, bile Acid Sequestrants (cholestyramine, cholestipol, coleserelam), SGLT2 inhibitors (ex-dapagliflozin (reduce HbA1c levels), an anti-IL-6R mAb, anti-TNF antibody (Remicade® (Infliximab), and Humira® (Adalimumab), Enbrel® (Etanercept) anti-inflammatory and/or immunosuppressive compounds (e.g., methotrexate, cyclosporin A cyclosporin microemulsion), tacrolimus, corticosteroids, statins, interferon beta, glatiramer acetate (Copaxone), interferon beta-1a (Avonex), interferon beta-1a (Rebif), interferon beta-1b (Betaseron or Betaferon), mitoxantrone (Novantrone), dexamethasone (Decadron), methylprednisolone (Depo-Medrol), prednisone (Deltasone) or an anti-obesity drug.

The invention further provides methods of treating or alleviating a symptom of autoimmune disease, an inflammatory disorder, a neurodegenerative disease or cancer by administering to a subject in need thereof a formulation according to the invention. Preferably the formulation is in an enteric-coated oral capsule. The autoimmune disease is for example, nonalcoholic steatohepatitis (NASH), primary biliary cirrhosis (PBC), Type 1 diabetes, Type 2 diabetes, or ulcerative colitis (UC). The method further includes administering to the subject at least one additional active agent. The active agent is for example, an NF-kB inhibitor, a GLP-1 or a beta cell resting compound, mesalamine or another 5-ASA drug, pentoxifylline, ursodeoxycholic acid, a PPARγ agonist, All Trans Retinoic Acid (ATRA), DPP-4 (gliptins-sitagliptin), a fatty acid synthesis inhibitor (e.g., cerulenin, quercetin, C7, apigenin, AICAR), a FXR agonist (e.g., bile salt activators, chenodeoxycholic acid, Obeticholic acid (OIBA, Ocaliva), fexaramine, cafestol, bile Acid Sequestrants (cholestyramine, cholestipol, coleserelam), SGLT2 inhibitors (ex-dapagliflozin (reduce HbA1c levels), an anti-IL-6R mAb, anti-TNF antibody (Remicade® (Infliximab), and Humira® (Adalimumab), Enbrel® (Etanercept) anti-inflammatory and/or immunosuppressive compounds (e.g., methotrexate, cyclosporin A cyclosporin microemulsion), tacrolimus, corticosteroids, statins, interferon beta, glatiramer acetate (Copaxone), interferon beta-1a (Avonex), interferon beta-1a (Rebif), interferon beta-1b (Betaseron or Betaferon), mitoxantrone (Novantrone), dexamethasone (Decadron), methylprednisolone (Depo-Medrol), prednisone (Deltasone) and an anti-obesity drug.

In another aspect, the invention provides method of activating mucosal immunity and immunomodulation in a subject comprising orally administering to a subject in need thereof an anti-CD-3 antibody. For example, the method included administering any of the formulations according to the invention. Preferably, the formulation is in an enteric-coated oral capsule.

In a further aspect, the invention provide a method of activating regulatory T-cells (Tregs) comprising orally administering to a subject in need thereof an anti-CD-3 antibody. For example, the method included administering any of the formulations according to the invention. Preferably, the formulation is in an enteric-coated oral capsule.

The invention further provides an enteric coated oral capsule containing an antibody liquid formulation having a unit dose of an antibody or antigen binding fragment thereof, 20% trehalose (w/v), and 0.1% methionine (w/v). The antibody has an IgG1 isotype The invention also provides an enteric coated oral capsule containing an antibody lyophilized formulation having a unit dose an antibody or antigen binding fragment thereof and about 34 mg trehalose and 0.17 mg methionine per mg of antibody or antigen binding fragment thereof. The antibody has an IgG1 isotype. Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

DETAILED DESCRIPTION

Figure 1:
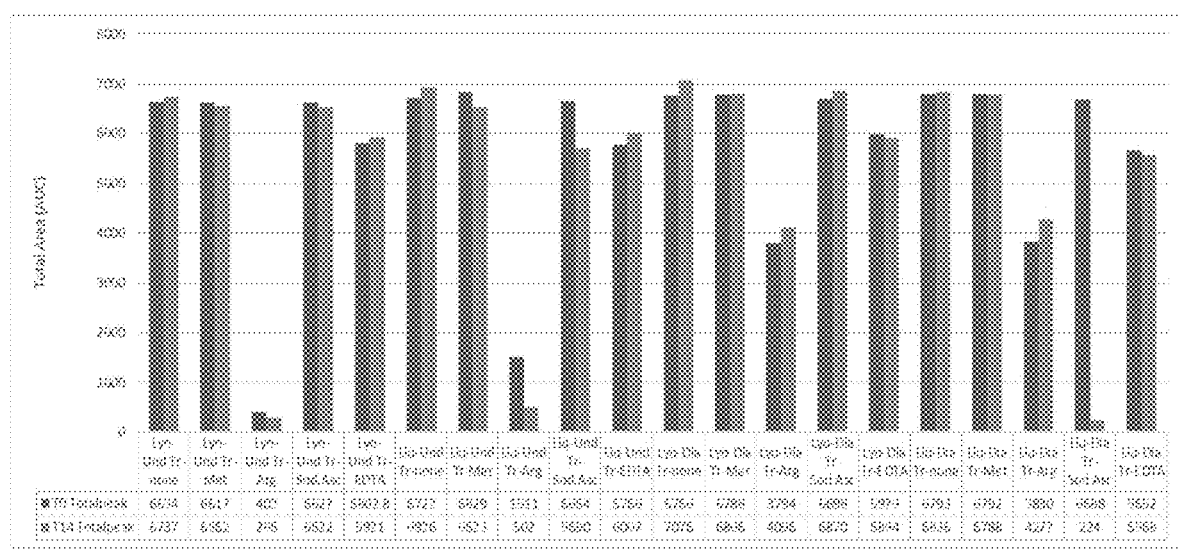
FIG. 1 is a bar chart showing the effect of time and temperature on NI-0401 formulations: SEC-HPLC: Total area (AUC).
Figure 2:
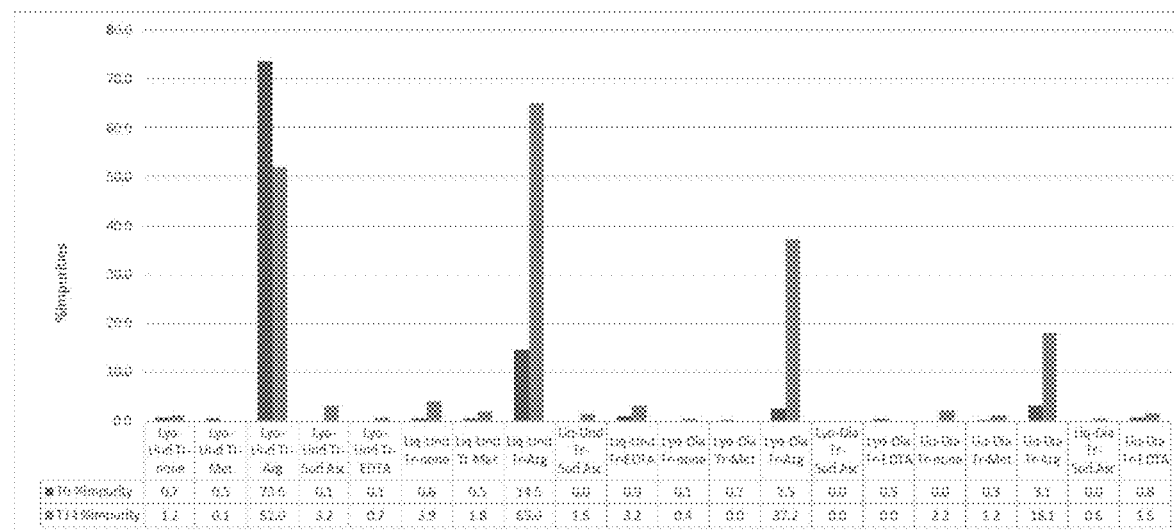
FIG. 2 is a bar chart showing the effect of time and temperature on NI-0401 formulations: SEC-HPLC: % Impurity.
Figure 3:
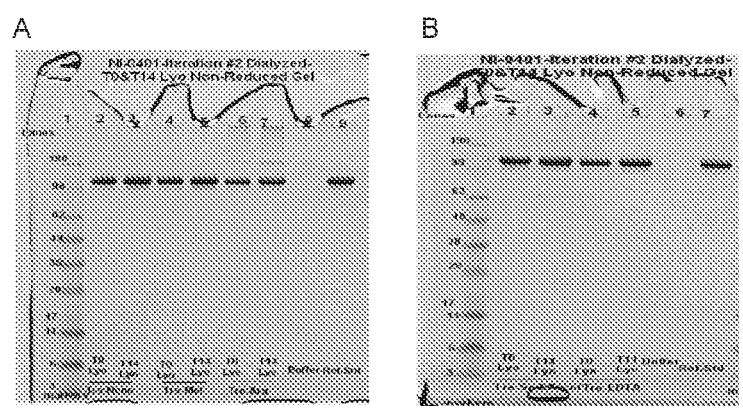
FIG. 3, panels A and B, are photographs of SDS gels showing the effect of time and temperature on the stability of dialyzed lyophilized NI-0401 formulations Iteration #2: Non-reduced SDS PAGE: T0&T14
Figure 4:
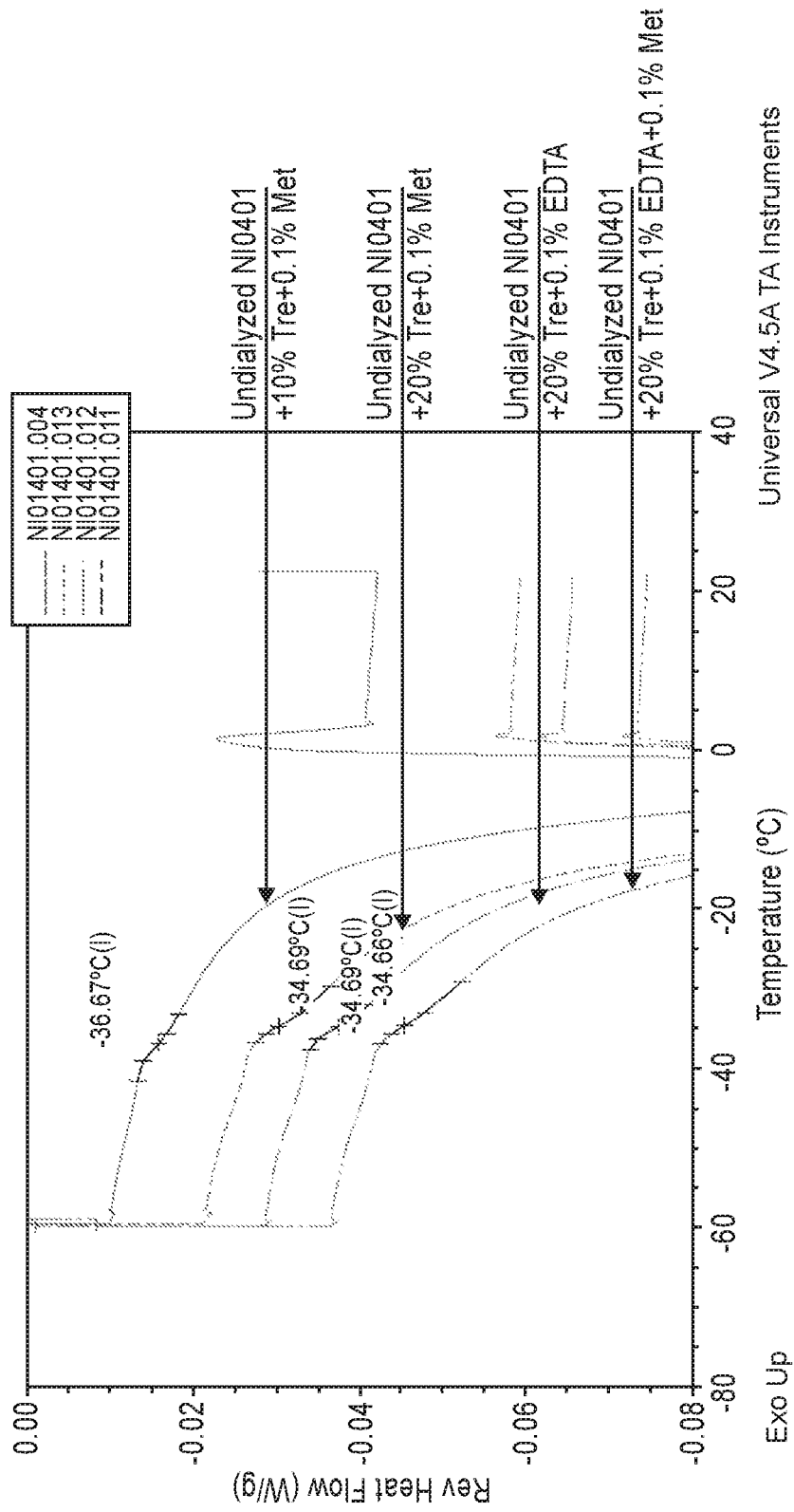
FIG. 4 is a graph showing the comparison of undilayzed lead formulation (10% Trehalose) glass transition temperature (tg) 10% Trehalose 0.1% methionine vs 20% Trehalose+/−EDTA; Overlay of Reverse heat flow change.

The present invention provides formulations and dosing for monoclonal antibodies, e.g., fully human monoclonal antibodies, specific against CD3 epsilon chain (CD3ε). Specifically, the invention provides oral, nasal and subcutaneous formulations of anti-CD3ε antibodies useful of target tissue specific immunomodulation. Unlike, systemic (e.g., intravenous) administration of anti-CD3 antibodies, the formulation of the present invention minimizes off target immunosuppression. An additional superior feature of the formulation of the invention, is the ability to dose at lower concentration of anti-CD3 antibodies than previously possible due to the target nature of the administration. The formulations are useful in treating or alleviating a symptom of autoimmune diseases, inflammatory disorders neurodegenerative disorders and cancer.

CD3 Antibodies

The present invention provides formulation of antibodies specific against CD3 epsilon chain (CD3ε). Antibodies specific for CD3 epsilon chain (CD3ε) and antigen binding fragments thereof are referred to herein as an anti-CD3 antibody, and the formulations are referred to herein as an "anti-CD3 antibody formulations." Any anti-CD3 antibody known in the art is suitable for use in the present invention. The anti-CD3 antibody is a monoclonal antibody.

Exemplary anti-CD3 antibodies, comprise a heavy chain complementarity determining region 1 (CDRH1) comprising the amino acid sequence GYGMH (SEQ ID NO: 1), a heavy chain complementarity determining region 2 (CDRH2) comprising the amino acid sequence VIWYDGSKKYYVDSVKG (SEQ ID NO: 3), a heavy chain complementarity determining region 3 (CDRH3) comprising the amino acid sequence QMGYWHFDL (SEQ ID NO: 4), a light chain complementarity determining region 1 (CDRL1) comprising the amino acid sequence RASQSVSSYLA (SEQ ID NO: 5), a light chain complementarity determining region 2 (CDRL2) comprising the amino acid sequence DASNRAT (SEQ ID NO: 6), and a light chain complementarity determining region 3 (CDRL3) comprising the amino acid sequence QQRSNWPPLT (SEQ ID NO: 7).

In some embodiments, the anti-CD3 antibody comprises a variable heavy chain amino acid sequence comprising QVQLVESGGGVVQPGRSLRLSCAASGFKFSGYGMHWVRQAPGKGLEWVAVIWYDGSK KYYVDSVKGRFTISRDNSKNTLYLQMNSLRAEDTAVYYCARQMGYWHFDLWGRGTLV TVSS (SEQ ID NO: 8) and a variable light chain amino acid sequence comprising EIVLTQSPATLSLSPGERATLSCRASQSVSSYLAWYQQKPGQAPRLLIYDASNRATGIPARF SGSGSGTDFTLTISSLEPEDFAVYYCQQRSNWPPLTFGGGTKVEIK (SEQ ID NO: 9).

Preferably, the anti-CD3 antibody comprises a heavy chain amino acid sequence comprising: QVQLVESGGGVVQPGRSLRLSCAASGFKFSGYGMHWVRQAPGKGLEWVAVIWYDGSK KYYVDSVKGRFTISRDNSKNTLYLQMNSLRAEDTAVYYCARQMGYWHFDLWGRG TLV TVSSASTKGPSVFPLAPSSKSTSGGTAALGCLVKDYFPEPVTVSWNSGALTSGVHTFPAVL QSSGLYSLSSVVTVPSSSLGTQTYICNVNHKPSNTKVDKRVEPKSCDKTHTCPPCPAPEAE GGPSVFLFPPKPKDTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQPREPQVYTLPPSR EEMTKNQVSLTCLVKGFYPSDIAVEWESNGQPENNYKTTPPVLDSDGSFFLYSKLTVDKS RWQQGNVFSCSVMHEALHNHYTQKSLSLSPGK (SEQ ID NO: 10) and a light chain amino acid sequence comprising: EIVLTQSPATLSLSPGERATLSCRASQSVSSYLAWYQQKPGQAPRLLIYDASNR ATGIPARFSGSGSGTDFTLTISSLEPEDFAVYYCQQRSNWPPLTFGGGTK VEIKRTVAAPSV FIFPPSDEQLKSGTASVVCLLNNFYPREAKVQWKVDNALQSGNSQESVTEQDSKDSTYSL SSTLTLSKADYEKHKVYACEVTHQGLSSPVTKSFNRGEC (SEQ ID NO: 11). This anti-CD3 antibody is referred to herein as NI-0401, Foralumab, or 28F11-AE. (See e.g., Dean Y, Dépis F, Kosco-Vilbois M. "Combination therapies in the context of anti-CD3 antibodies for the treatment of autoimmune diseases." Swiss Med Wkly. (2012) (the contents of which are hereby incorporated by reference in its entirety).

In some embodiments the anti-CD3 antibody is a fully human antibody or a humanized antibody. In some embodiments, the anti-CD3 antibody formulation includes a full length anti-CD3 antibody. In alternative embodiments, the anti-CD3 antibody formulation includes an antibody fragment that specifically binds CD3. In some embodiments, the anti-CD3 antibody formulation includes a combination of full-length anti-CD3 antibodies and antigen binding fragments that specifically bind CD3.

In some embodiments, the antibody or antigen-binding fragment thereof that binds CD3 is a monoclonal antibody, domain antibody, single chain, Fab fragment, a F(ab')$_2$ fragment, a scFv, a scAb, a dAb, a single domain heavy chain antibody, or a single domain light chain antibody. In some embodiments, such an antibody or antigen-binding fragment thereof that binds CD3 is a mouse, other rodent, chimeric, humanized or fully human monoclonal antibody.

Optionally, the anti-CD3 antibody or antigen binding fragment thereof used in the formulations of the disclosure includes at least one an amino acid mutation. Typically, the mutation is in the constant region. The mutation results in an antibody that has an altered effector function. An effector function of an antibody is altered by altering, i.e., enhancing or reducing, the affinity of the antibody for an effector molecule such as an Fc receptor or a complement component. For example, the mutation results in an antibody that is capable of reducing cytokine release from a T-cell. For example, the mutation is in the heavy chain at amino acid residue 234, 235, 265, or 297 or combinations thereof. Preferably, the mutation results in an alanine residue at either position 234, 235, 265 or 297, or a glutamate residue at position 235, or a combination thereof.

Preferably, the anti-CD3 antibody provided herein contains one or more mutations that prevent heavy chain constant region-mediated release of one or more cytokine(s) in vivo.

In some embodiments, the anti-CD3 antibody or antigen binding fragment thereof used in the formulations of the disclosure is a fully human antibody. The fully human CD3 antibodies used herein include, for example, a $L^{234}$ $L^{235} \rightarrow A^{234}$ $E^{235}$ mutation in the Fc region, such that cytokine release upon exposure to the anti-CD3 antibody is significantly reduced or eliminated. The $L^{234}$ $L^{235} \rightarrow A^{234}$ $E^{235}$ mutation in the Fc region of the anti-CD3 antibodies provided herein reduces or eliminates cytokine release when the anti-CD3 antibodies are exposed to human leukocytes, whereas the mutations described below maintain significant cytokine release capacity. For example, a significant reduction in cytokine release is defined by comparing the release of cytokines upon exposure to the anti-CD3 antibody having a $L^{234}$ $L^{235} \rightarrow A^{234}$ $E^{235}$ mutation in the Fc region to level of cytokine release upon exposure to another anti-CD3 antibody having one or more of the mutations described below. Other mutations in the Fc region include, for example, $L^{234}$ $L^{235} \rightarrow A^{234}$ $A^{235}$, $L^{235} \rightarrow E^{235}$, $N^{297} \rightarrow A^{297}$, and $D^{265} \rightarrow A^{265}$.

The term "cytokine" refers to all human cytokines known within the art that bind extracellular receptors expressed on the cell surface and thereby modulate cell function, including but not limited to IL-2, IFN-gamma, TNF-a, IL-4, IL-5, IL-6, IL-9, IL-10, and IL-13.

Formulations

The anti-CD3 formulation comprises a unit dose of the anti-CD3 antibody in the range of: about 0.1 mg to about 50 mg; about 0.1 mg to about 25 mg; or 0.1 mg to about 10 mg. For example, the unit dose is about 0.1, 0.2, 0.3, 0.4, 0.5, 0.6, 0.7, 0.8, 0.9, 1.0, 1.5, 2.0, 2.5, 3.0, 3.5, 4.0, 5.0, 5.5, 6.0, 6.5, 7.0, 7.5, 8.0, 8.5, 9, 9.5, 10 mg or more. Preferably, the unit dose is 0.5 mg, 2.5 mg or 5.0 mg.

The anti-CD3 formulation can be a liquid. For example the liquid formulation is aqueous. Alternatively, the anti-CD3 formulation is a lyophilized powder. When the anti-CD3 formulation is a lyophilized powder, additionally bulking agent may be added to provide adequate structure to the lyophilized cake. This additional bulking agent may increase the stability of the lyophilized cake upon storage. Alternatively, this additional bulking agent may aide in the production of the dosage form, e.g., oral capsule. Bulking agents are described herein and include polyols such as, trehalose, mannitol, maltose, lactose, sucrose, sorbitol, or glycerol, starch, microcrystalline cellulose, low moisture microcrystalline cellulose such as Avicel or polethylen glycols (PEG).

The anti-CD3 antibody formulation includes one or more salts (a buffering salt), one or more polyols and one or more excipients. The formulations of the present invention may also contain buffering agents, or preservatives. The anti-CD3 antibody formulation is buffered in a solution at a pH in the range of about 4 to 8; in the range of about 4 to 7; in the range of about 4 to 6; in the range of about 5 to 6; or in the range of about 5.5 to 6.5. Preferably, the pH is 5.5.

Examples of salts include those prepared from the following acids: hydrochloric, hydrobromic, sulfuric, nitric, phosphoric, maleic, acetic, salicylic, citric, boric, formic, malonic, succinic, and the like. Such salts can also be prepared as alkaline metal or alkaline earth salts, such as sodium, potassium or calcium salts. Examples of buffering agents include phosphate, citrate, acetate, and 2-(N-morpholino)ethanesulfonic acid (IVIES).

The formulations of the present invention may include a buffer system. As used in this application, the terms "buffer" or "buffer system" is meant a compound that, usually in combination with at least one other compound, provides a buffering system in solution that exhibits buffering capacity, that is, the capacity to neutralize, within limits, either acids or bases (alkali) with relatively little or no change in the original pH.

Buffers include borate buffers, phosphate buffers, calcium buffers, and combinations and mixtures thereof. Borate buffers include, for example, boric acid and its salts, for example, sodium borate or potassium borate. Borate buffers also include compounds such as potassium tetraborate or potassium metaborate that produce borate acid or its salt in solutions.

A phosphate buffer system includes one or more monobasic phosphates, dibasic phosphates and the like. Particularly useful phosphate buffers are those selected from phosphate salts of alkali and/or alkaline earth metals. Examples of suitable phosphate buffers include one or more of sodium dibasic phosphate (Na2HPO4), sodium monobasic phosphate (NaH2PO4) and potassium monobasic phosphate (KH2PO4). The phosphate buffer components frequently are used in amounts from 0.01% or to 0.5% (w/v), calculated as phosphate ion.

Other known buffer compounds can optionally be added to the according to the CD3 formulations, for example, citrates, sodium bicarbonate, TRIS, and the like. Other ingredients in the solution, while having other functions, may also affect the buffer capacity. For example, EDTA, often used as a complexing agent, can have a noticeable effect on the buffer capacity of a solution.

Preferred salts for use in the formulation of the invention include sodium chloride, sodium acetate, sodium acetate trihydrate and sodium citrate.

The concentration of salt in the formulations according to the invention is between about 10 mM and 500 mM, between about 25 m and 250 mM, between about 25 nM and 150 mM.

The sodium acetate trihydrate is at a concentration in the range of about 10 mM to 100 mM. For example, the sodium acetate trihydrate is at about 10, 15, 20, 25, 30, 35, 40, 45, 50, 55, 60, 65, 70, 75, 80, 85, 90, 95 or 100 mM. Preferably, the sodium acetate trihydrate is at 25 mM.

The sodium chloride at a concentration in the range of about 50 mM to 500 mM. For example, the sodium chloride is at about 50, 55, 60, 65, 70, 75, 80, 85, 90, 95, 100. 125, 150, 175, 200, 225, 250, 275, 300, 325, 350, 375, 400, 425, 450, 475 or 500 mM. Preferably, the sodium chloride is at a concentration of about 125 mM.

The sodium citrate is at a concentration in the range of about 10 mM to 100 mM For example the sodium citrate is at about 10, 15, 20, 25, 30, 35, 40, 45, 50, 55, 60, 65, 70, 75, 80, 85, 90, 95 or 100 mM. Preferably, the sodium citrate is in the range of about 25 to 50 mM.

In some embodiments, the salt is sodium acetate trihydrate at a concentration in the range of about 25 mm to 100 mm and sodium chloride at a concentration in the range of about 150 mm to 500 mm.

Preferably, the formulation includes about 25 mM sodium acetate trihydrate and about 150 mM sodium chloride.

The formulation includes one or more polyols as a bulking agent and/or stabilizing excipients. Polyols include for example, trehalose, mannitol, maltose, lactose, sucrose, sorbitol, or glycerol. The polyols is at a concentration in the range of about 0.1% to 50% or 5% to 25%. For example, the polyol is at about 1, 2, 3, 4, 5, 10, 15, 20, 25, 30, 35, 40, 45 or 50%

In some embodiments, the polyol is trehalose at a concentration in the range of about 1% to 50% or 5% to 25%. For example, the trehalose is at about 1, 2, 3, 4, 5, 10, 15, 20, 25, 30, 35, 40, 45 or 50%. Preferably the trehalose is at a concentration of about 10% or about 20%. Most preferably, the trehalose is at a concentration of about 20%.

In some embodiments, the polyol is sorbitol at a concentration in the range of about 1% to about 10%. In some embodiments, the polyol is glycerol at a concentration in the range of about 1% to about 10%.

In some embodiments, the polyol is mannitol at a concentration in the range of about 0.1% to about 10%. In some embodiments, the polyol is maltose at a concentration in the range of about 1% to about 10%.

The formulation includes one or more excipients and/or surfactants to suppress or otherwise reduce antibody aggregation. Suitable excipients to reduce antibody aggregation include, by way of non-limiting example, a surfactant such as, by way of non-limiting example, Polysorbate 20 or Polysorbate 80. In some embodiments, the Polysorbate 20 or Polysorbate 80 is present at a concentration in the range of about 0.01 to 1% or about 0.01 to 0.05%. For example the Polysorbate 20 or Polysorbate 80 is at a concentration of about 0.01. 0.02, 0.03, 0.04, 0.05, 0.06, 0.07. 0.08, 0.09, 0.1, 0.2, 0.3. 0.4, 0.5, 0.6, 0.7, 0.8. 0.9, or 1.0%.

Preferably the surfactant is Polysorbate 80 at a concentration in the range of about 0.01 to 0.05%. More preferably, the Polysorbate 80 is at 0.02%.

The formulation includes one or more excipients to reduce antibody oxidation. Suitable excipients to reduce antibody oxidation include, by way of non-limiting example, antioxidants. Antioxidants include for example, methionine, D-arginine, BHT or ascorbic acid. The antioxidant is present at a concentration in the range of about 0.01% to 1%; 0.1% to 1%; or 0.1% to 0.5%. In some embodiments, the antioxidant is methionine. In some embodiments, the methionine is present at a concentration in the range of about 0.01% to 1%; 0.1% to 1%; or 0.1% to 0.5%. For example, the methionine is present at a concentration of about 0.01.

0.02, 0.03, 0.04, 0.05, 0.06, 0.07. 0.08, 0.09, 0.1, 0.2, 0.3. 0.4, 0.5, 0.6, 0.7, 0.8. 0.9, or 1.0%. Preferably, the methionine is at about 0.1%.

The formulation includes one or more chelating agents, such as for example ethylenediaminetetraacetic acid (EDTA). The chelating agent is at a concentration in the range of 0.01% to 1%; 0.1% to 1%; or 0.1% to 0.5%. For example, the chelating agent is present at a concentration of about 0.01. 0.02, 0.03, 0.04, 0.05, 0.06, 0.07. 0.08, 0.09, 0.1, 0.2, 0.3. 0.4, 0.5, 0.6, 0.7, 0.8. 0.9, or 1.0%. Preferably, the chelating agent is EDTA at a concentration of about 0.1%.

In some embodiments, the formulation includes one or more excipients to increase stability. In some embodiments, the excipient to increase stability is human serum albumin. In some embodiments, the human serum albumin is present in the range of about 1 mg to about 5 mg.

In some embodiments, the formulation includes magnesium stearate (Mg stearate), an amino acid, or both mg-stearate and an amino acid. Suitable amino acids include for example, leucine, arginine, histidine, or combinations thereof.

In some embodiments the one or more additional excipients is low moisture microcrystalline cellulose, such as Avicel, polyethylene glycols (PEG), or a starch.

Further examples of pharmaceutically acceptable carriers and excipients useful for the formulations of the present invention include, but are not limited to binders, fillers, disintegrants, lubricants, anti-microbial agents, antioxidant, and coating agents such as: BINDERS: corn starch, potato starch, other starches, gelatin, natural and synthetic gums such as acacia, xanthan, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone (e.g., povidone, crospovidone, copovidone, etc), methyl cellulose, Methocel, pregelatinized starch (e.g., STARCH 1500® and STARCH 1500 LM®, sold by Colorcon, Ltd.), hydroxypropyl methyl cellulose, microcrystalline cellulose (FMC Corporation, Marcus Hook, Pa., USA), Emdex, Plasdone, or mixtures thereof, FILLERS: talc, calcium carbonate (e.g., granules or powder), dibasic calcium phosphate, tribasic calcium phosphate, calcium sulfate (e.g., granules or powder), microcrystalline cellulose, powdered cellulose, dextrates, kaolin, mannitol, silicic acid, sorbitol, starch, pre-gelatinized starch, dextrose, fructose, honey, lactose anhydrate, lactose monohydrate, lactose and aspartame, lactose and cellulose, lactose and microcrystalline cellulose, maltodextrin, maltose, mannitol, microcrystalline cellulose & guar gum, molasses, sucrose, or mixtures thereof, DISINTEGRANTS: agar-agar, alginic acid, calcium carbonate, microcrystalline cellulose, croscarmellose sodium, crospovidone, polacrilin potassium, sodium starch glycolate, (such as Explotab), potato or tapioca starch, other starches, pre-gelatinized starch, clays, other algins, other celluloses, gums (like gellan), low-substituted hydroxypropyl cellulose, ployplasdone, or mixtures thereof, LUBRICANTS: calcium stearate, magnesium stearate, mineral oil, light mineral oil, glycerin, sorbitol, mannitol, polyethylene glycol, other glycols, compritol, stearic acid, sodium lauryl sulfate, sodium stearyl fumarate, (such as Pruv), vegetable based fatty acids lubricant, talc, hydrogenated vegetable oil (e.g., peanut oil, cottonseed oil, sunflower oil, sesame oil, olive oil, corn oil and soybean oil), zinc stearate, ethyl oleate, ethyl laurate, agar, syloid silica gel (AEROSIL 200, W.R. Grace Co., Baltimore, Md. USA), a coagulated aerosol of synthetic silica (Deaussa Co., Piano, Tex. USA), a pyrogenic silicon dioxide (CAB-O-SIL, Cabot Co., Boston, Mass. USA), or mixtures thereof, ANTI-CAKING AGENTS: calcium silicate, magnesium silicate, silicon dioxide, colloidal silicon dioxide, talc, or mixtures thereof, ANTIMICROBIAL AGENTS: benzalkonium chloride, benzethonium chloride, benzoic acid, benzyl alcohol, butyl paraben, cetylpyridinium chloride, cresol, chlorobutanol, dehydroacetic acid, ethylparaben, methylparaben, phenol, phenylethyl alcohol, phenoxyethanol, phenylmercuric acetate, phenylmercuric nitrate, potassium sorbate, propylparaben, sodium benzoate, sodium dehydroacetate, sodium propionate, sorbic acid, thimersol, thymo, or mixtures thereof, ANTOXIDANTS: ascorbic acid, BHA, BHT, EDTA, or mixture thereof, and COATING AGENTS: sodium carboxymethyl cellulose, cellulose acetate phthalate, ethylcellulose, gelatin, pharmaceutical glaze, hydroxypropyl cellulose, hydroxypropyl methylcellulose (hypromellose), hydroxypropyl methyl cellulose phthalate, methylcellulose, polyethylene glycol, polyvinyl acetate phthalate, shellac, sucrose, titanium dioxide, carnauba wax, microcrystalline wax, gellan gum, maltodextrin, methacrylates, microcrystalline cellulose and carrageenan or mixtures thereof.

The formulation can also include other excipients and categories thereof including but not limited to Pluronic®, Poloxamers (such as Lutrol® and Poloxamer 188), ascorbic acid, glutathione, protease inhibitors (e.g. soybean trypsin inhibitor, organic acids), pH lowering agents, creams and lotions (like maltodextrin and carrageenans); materials for chewable tablets (like dextrose, fructose, lactose monohydrate, lactose and aspartame, lactose and cellulose, maltodextrin, maltose, mannitol, microcrystalline cellulose and guar gum, sorbitol crystalline); parenterals (like mannitol and povidone); plasticizers (like dibutyl sebacate, plasticizers for coatings, polyvinylacetate phthalate); powder lubricants (like glyceryl behenate); soft gelatin capsules (like sorbitol special solution); spheres for coating (like sugar spheres); spheronization agents (like glyceryl behenate and microcrystalline cellulose); suspending/gelling agents (like carrageenan, gellan gum, mannitol, microcrystalline cellulose, povidone, sodium starch glycolate, xanthan gum); sweeteners (like aspartame, aspartame and lactose, dextrose, fructose, honey, maltodextrin, maltose, mannitol, molasses, sorbitol crystalline, sorbitol special solution, sucrose); wet granulation agents (like calcium carbonate, lactose anhydrous, lactose monohydrate, maltodextrin, mannitol, microcrystalline cellulose, povidone, starch), caramel, carboxymethylcellulose sodium, cherry cream flavor and cherry flavor, citric acid anhydrous, citric acid, confectioner's sugar, D&C Red No. 33, D&C Yellow #10 Aluminum Lake, disodium edetate, ethyl alcohol 15%, FD&C Yellow No. 6 aluminum lake, FD&C Blue #1 Aluminum Lake, FD&C Blue No. 1, FD&C blue no. 2 aluminum lake, FD&C Green No. 3, FD&C Red No. 40, FD&C Yellow No. 6 Aluminum Lake, FD&C Yellow No. 6, FD&C Yellow No. 10, glycerol palmitostearate, glyceryl monostearate, indigo carmine, lecithin, manitol, methyl and propyl parabens, mono ammonium glycyrrhizinate, natural and artificial orange flavor, pharmaceutical glaze, poloxamer 188, Polydextrose, polysorbate 20, polysorbate 80, polyvidone, pregelatinized corn starch, pregelatinized starch, red iron oxide, saccharin sodium, sodium carboxymethyl ether, sodium chloride, sodium citrate, sodium phosphate, strawberry flavor, synthetic black iron oxide, synthetic red iron oxide, titanium dioxide, and white wax.

In some embodiments the anti-CD3 formulation is a liquid and the concentration of sodium acetate is about 10 mM to 500 mM; the concentration of sodium chloride is about 10 mM to 500 mM; the concentration of polysorbate 80 is about 0.01% to 1% (w/v); the concentration of trehalose is about 5% to 50% (w/v); and the concentration of methionine is 0.01% to 1% (w/v). Optionally, the formulation further includes EDTA at the concentration of about 0.01% to 1% (w/v). The unit dose of the anti-CD3 antibody or antigen binding fragment thereof is in the range of about 0.1 mg to 10 mg. In some embodiments the liquid formulation is lyophilized to form a powder.

In some embodiments the anti-CD3 formulation is a liquid and contains 25 mM sodium acetate, 125 mM sodium chloride, 0.02% polysorbate 80 (w/v), 20% trehalose (w/v), 0.1% methionine (w/v) and a unit dose of the anti-CD3 antibody or antigen binding fragment thereof in the range of about 0.1 mg to 10 mg. Optionally, the formulation further includes 0.1% EDTA (w/v). In some embodiments the liquid formulation is lyophilized to form a powder.

In a specific embodiment, the liquid anti-CD3 formulation includes 25 mM sodium acetate, 125 mM sodium chloride, 0.02% polysorbate 80 (w/v), 20% trehalose (w/v), 0.1% methionine (w/v) and a 0.5 mg unit dose of the anti-CD3 antibody or antigen binding fragment. Also included in the invention is a lyophilized powder of this formulation.

In a specific embodiment, the liquid anti-CD3 formulation includes 25 mM sodium acetate, 125 mM sodium chloride, 0.02% polysorbate 80 (w/v), 20% trehalose (w/v), 0.1% methionine (w/v) and a 0.2.5 mg unit dose of the anti-CD3 antibody or antigen binding fragment. Also included in the invention is a lyophilized powder of this formulation.

In a specific embodiment, the liquid anti-CD3 formulation includes 25 mM sodium acetate, 125 mM sodium chloride, 0.02% polysorbate 80 (w/v), 20% trehalose (w/v), 0.1% methionine (w/v) and a 5.0 mg unit dose of the anti-CD3 antibody or antigen binding fragment. Also included in the invention is a lyophilized powder of this formulation.

In a specific embodiment, the liquid anti-CD3 formulation includes 25 mM sodium acetate, 125 mM sodium chloride, 0.02% polysorbate 80 (w/v), 20% trehalose (w/v), 0.1% methionine (w/v), 0.1% EDTA (w/v) and a 0.5 mg unit dose of the anti-CD3 antibody or antigen binding fragment. Also included in the invention is a lyophilized powder of this formulation.

In a specific embodiment, the liquid anti-CD3 formulation includes 25 mM sodium acetate, 125 mM sodium chloride, 0.02% polysorbate 80 (w/v), 20% trehalose (w/v), 0.1% methionine (w/v), 0.1% EDTA (w/v) and a 0.2.5 mg unit dose of the anti-CD3 antibody or antigen binding fragment. Also included in the invention is a lyophilized powder of this formulation.

In a specific embodiment, the liquid anti-CD3 formulation includes 25 mM sodium acetate, 125 mM sodium chloride, 0.02% polysorbate 80 (w/v), 20% trehalose (w/v), 0.1% methionine (w/v), 0.1% EDTA (w/v) and a 5.0 mg unit dose of the anti-CD3 antibody or antigen binding fragment. Also included in the invention is a lyophilized powder of this formulation.

In some embodiments the formulation is a lyophilized powder where the ratio of anti-CD3 antibody or antigen binding fragment to polysorbate 80 is about 1:0.01 to 0.1 (w/w); the ratio of anti-CD3 antibody or antigen binding fragment trehalose is about 1:10 to 50 (w/w); the ratio of anti-CD3 antibody or antigen binding fragment methionine about 1:0.1 to 0.5 (w/w); the ratio of anti-CD3 antibody or antigen binding fragment sodium acetate is about 1:0.1 to 1.0 (w/w); and the ratio of anti-CD3 antibody or antigen binding fragment sodium chloride is about 1:0.5 to 2.0 (w/w). Optionally, the formulation further includes EDTA where the ratio of anti-CD3 antibody or antigen binding fragment to: EDTA is about 1:0.1 to 0.5 (w/w). The unit dose of the anti-CD3 antibody or antigen binding fragment thereof is in the range of about 0.1 mg to 10 mg.

In some embodiments, the anti-CD3 formulation is a powder, e.g., a lyophilized powder having a unit dose of about 0.1 mg to 10 mg of an anti-CD3 antibody or antigen binding fragment thereof and about 0.58 mg of sodium acetate trihydrate, about 1.25 mg sodium chloride, about 0.034 mg polysorbate 80, about 34 mg trehalose and about 0.17 mg methionine per 1 mg of anti-CD3 antibody or antigen binding fragment thereof Optionally, the powder formulation further included 0.17 mg EDTA per 1 mg of anti-CD3 antibody or antigen binding fragment thereof. Preferably, the unit dose is 0.5 mg, 2.5 mg or 5.0 mg.

In a specific embodiment, the anti-CD3 formulation is a powder, e.g., a lyophilized powder having a unit dose of about 0.5 mg of an anti-CD3 antibody or antigen binding fragment thereof and about 0.58 mg of sodium acetate trihydrate, about 1.25 mg sodium chloride, about 0.034 mg polysorbate 80, about 34 mg trehalose and about 0.17 mg methionine per 1 mg of anti-CD3 antibody or antigen binding fragment thereof.

In a specific embodiment, the anti-CD3 formulation is a powder, e.g., a lyophilized powder having a unit dose of about 2.5 mg of an anti-CD3 antibody or antigen binding fragment thereof and about 0.58 mg of sodium acetate trihydrate, about 1.25 mg sodium chloride, about 0.034 mg polysorbate 80, about 34 mg trehalose and about 0.17 mg methionine per 1 mg of anti-CD3 antibody or antigen binding fragment thereof.

In a specific embodiment, the anti-CD3 formulation is a powder, e.g., a lyophilized powder having a unit dose of about 5 mg of an anti-CD3 antibody or antigen binding fragment thereof and about 0.58 mg of sodium acetate trihydrate, about 1.25 mg sodium chloride, about 0.034 mg polysorbate 80, about 34 mg trehalose and about 0.17 mg methionine per 1 mg of anti-CD3 antibody or antigen binding fragment thereof.

In a specific embodiment, the anti-CD3 formulation is a powder, e.g., a lyophilized powder having a unit dose of about 0.5 mg of an anti-CD3 antibody or antigen binding fragment thereof and about 0.58 mg of sodium acetate trihydrate, about 1.25 mg sodium chloride, about 0.034 mg polysorbate 80, about 34 mg trehalose, about 0.17 mg EDTA and about 0.17 mg methionine per 1 mg of anti-CD3 antibody or antigen binding fragment thereof In a specific embodiment, the anti-CD3 formulation is a powder, e.g., a lyophilized powder having a unit dose of about 2.5 mg of an anti-CD3 antibody or antigen binding fragment thereof and about 0.58 mg of sodium acetate trihydrate, about 1.25 mg sodium chloride, about 0.034 mg polysorbate 80, about 34 mg trehalose, about 0.17 mg EDTA and about 0.17 mg methionine per 1 mg of anti-CD3 antibody or antigen binding fragment thereof In a specific embodiment, the anti-CD3 formulation is a powder, e.g., a lyophilized powder having a unit dose of about 5 mg of an anti-CD3 antibody or antigen binding fragment thereof and about 0.58 mg of sodium acetate trihydrate, about 1.25 mg sodium chloride, about 0.034 mg polysorbate 80, about 34 mg trehalose, about 0.17 mg EDTA and about 0.17 mg methionine per 1 mg of anti-CD3 antibody or antigen binding fragment thereof The moisture (i.e., water) content of the formulations according to the invention (either in a liquid, lyophilized or final dosage form (e.g. capsule) is less than about 7%, 6%, 5%, 4%, 3%, 2% or 1%. Preferably, the moisture content is in the range of 2-5%, more preferably he moisture content is in the range of 1-2%, most preferably, the moisture content is less than 1%. Methods of determining moisture content is known in the art, for example moisture content is determined by Karl Fischer titration.

In some embodiments, the osmolality of the formulation is about 800-950 (e.g., about 825-925) mOsm/kg.

The anti-CD3 antibody formulations of the invention (either in a liquid, lyophilized or final dosage form (e.g. capsule) is suitable for storage at about 2° C. to about 4° C., 15° C. or at ambient temperature. In some embodiments, the formulations are formulation is stored with a desiccant molecular sieve pack to reduce moisture during storage. In some embodiments, the formulation is stored in a container, e.g., a bottle or other suitable container, with a desiccant molecular sieve pack to reduce moisture during storage.

The formulations of the present invention (either in a liquid, lyophilized or final dosage form (e.g. capsule) provide for the chemical stability of the formulated antibody and other optional active agents of the formulation. "Stability" and "stable" in this context refers to the resistance of antibody and other optional active agents to chemical degradation and physical changes such as settling, precipitation, aggregation under given manufacturing, and preparation, transportation and storage conditions. The "stable" formulations of the invention also preferably retain at least 90%, 95%, 98%, 99%, or 99.5% of a starting or reference amount under given manufacturing, preparation, transportation, and/or storage conditions. The amount of antibody and other optional active agents can be determined using any art-recognized method, for example, as UV-Vis spectrophotometry and high pressure liquid chromatography (HPLC), or SDS-PAGE.

The anti-CD3 antibody formulations of the invention (either in a liquid, lyophilized or final dosage form (e.g. capsule) are stable for at least 3 months at either 4° C., 15° C., or ambient temperature. The formulations are stable for more than 3 months at either 4° C. or 15° C., for example, at least 4 months, at least 5 months, at least 6 months, at least 7 months, at least 8 months, at least 9 months, at least 10 months, at least 11 months, at least 12 months, at least 18 months, at least 24 months and/or greater than 24 months at either 4° C., 15° C., or ambient temperature.

The anti-CD3 antibody formulations of the invention (either in a liquid, lyophilized or final dosage form (e.g. capsule) have a purity of at least 90%, 91%, 92% 95%, 95%, 97%, 985, 99% or more IgG as heavy and light chains.

The anti-CD3 antibody formulations of the invention (either in a liquid, lyophilized or final dosage form (e.g. capsule) have less than 5%, 4%, 3%, 2%, 1% total impurities.

The anti-CD3 antibody formulations of the invention (either in a liquid, lyophilized or final dosage form (e.g. capsule) have least 90%, 91%, 92% 95%, 95%, 97%, 985, 99% or more IgG monomers.

The anti-CD3 antibody formulations of the invention (either in a liquid, lyophilized or final dosage form (e.g. capsule) have less than 5%, 4%, 3%, 2%, 1%, 0.9%, 0.8%, 0.7%, 0.6%, 0.5%, 0.4%, 0.3%, 0.2%, 0.1% total IgG aggregates.

Dosage Forms

The formulations of the invention may be specifically formulated for enteral, parenteral, or nasal administration.

For enteral administration, i.e., oral, the formulations may be a capsule or a tablet. Parental administration includes intravenous, subcutaneous, intramuscular, and intra-articular administration and may be a liquid or lyophilized powder in a sealed vial or other container.

For nasal administration, the formulations may be an aerosol in a sealed vial or other suitable container The capsules include soft gel capsules or hard shell capsules. Soft gel capsules are a soft gel or gelatin or gelatin-like material. The hard shell or soft gel capsules are HPMC capsules. The capsules, soft gel or hard shell may be filed with a liquid anti-CD3 formulation or a powdered, e.g., lyophilized, anti-CD3 formulation. Exemplary, liquid and powdered anti-CD3 formulations are described above.

In some embodiments, each capsule includes a sufficient enteric coating to bypass stomach acidity. Any suitable enteric coating can be used in the oral anti-CD3 antibody formulations, including, by way of non-limiting example, enteric coatings such as Eudragit®, e.g., Eudragit® L 30 D/L 100-55, which releases the anti-CD3 antibody at a pH above 4 or 5.

In some embodiments, each capsule in the oral anti-CD3 antibody formulation comprises a soft gel or gelatin or gelatin-like material having a size in the range of 0 to 2, e.g., a size 0, a size 1, and/or a size 2.

In some embodiments capsule in the oral anti-CD3 antibody formulation is a liquid-filled hard capsule (LFHC). Any suitable LFHC can be used in the oral anti-CD3 antibody formulation of the disclosure, including, by way of non-limiting example, Licaps® and other LFHC by Capsugel®.

In some embodiments, each liquid-filled capsule in the oral anti-CD3 antibody formulation contains a volume less than about 1000 μL, e.g., less than about 75 μL, and/or less than about 500 μL. In some embodiments, each liquid-filled capsule in the oral anti-CD3 antibody formulation contains a volume in a range from about 50 μL to about 1000 μL, from about 100 μL to about 1000 μL, from about 200 μL to about 1000 μL, from about 250 μL to about 1000 μL, from about 50 μL to about 500 μL, from about 100 μL to about 500 μL, from about 200 μL to about 500 μL, and/or from about 250 μL to about 500 μL.

A preferred oral formulation includes an enteric coated oral capsule containing an anti-CD3 antibody lyophilized formulation having a unit dose of about 0.1 mg to 10 mg of an anti-CD3 antibody or antigen binding fragment thereof and about 0.58 mg of sodium acetate trihydrate, about 1.25 mg sodium chloride, about 0.034 mg polysorbate 80, about 34 mg trehalose and about 0.17 mg methionine per 1 mg of anti-CD3 antibody or antigen binding fragment thereof Optionally, the enteric-coated oral capsule further includes 0.17 mg EDTA per 1 mg of anti-CD3 antibody or antigen binding fragment thereof. The unit dosed is 0.5 mg, 2.5 mg or 5.0 mg.

Another preferred oral formulation includes an enteric coated oral capsule containing an anti-CD3 antibody liquid formulation comprising a unit dose of about 0.1 mg to 10 mg of an anti-CD3 antibody or antigen binding fragment thereof, 25 mM sodium acetate trihydrate, 125 mM sodium chloride, 0.02% polysorbate 80 (w/v), 20% trehalose (w/v), and 0.1% methionine (w/v). Optionally, the enteric-coated oral capsule further includes 0.1% EDTA The unit dosed is 0.5 mg, 2.5 mg or 5.0 mg.

In some embodiments, the anti-CD3 antibody formulation is a subcutaneous formulation. In some embodiments, the subcutaneous anti-CD3 antibody formulation is housed in a sealed vial or other container.

In some embodiments, the subcutaneous anti-CD3 antibody formulation includes an anti-CD3 antibody, at least one salt, at least one surfactant, and a volume of water necessary to bring the formulation to the desired injection volume.

In some embodiments, the subcutaneous anti-CD3 antibody formulation includes about 2 mg/mL of the anti-CD3 antibody, about 7.31 mg sodium chloride, about 3.40 mg sodium acetate trihydrate, about 0.20 mg Polysorbate 80, and water in an amount to bring the formulation volume up to 1 ml for the desired injection volume. The subcutaneous anti-CD3 formulation should be at a pH in the range of about 4 to 6.

In some embodiments, the subcutaneous anti-CD3 antibody formulation is stored in a vial or other suitable container under refrigeration, e.g., in the range of about 2° C. to about 8° C. In some embodiments, the subcutaneous anti-CD3 antibody formulation is not shaken. In some embodiments, the subcutaneous anti-CD3 antibody formulation is not frozen. In some embodiments, the subcutaneous anti-CD3 antibody formulation is diluted prior to administration.

In some embodiments, the subcutaneous anti-CD3 antibody formulation is administered at a dose in a range from about 1 mg/60 kg body weight to about 10 mg/60 kg body weight.

In some embodiments, the anti-CD3 antibody formulation is a nasal formulation. In some embodiments, the nasal anti-CD3 antibody formulation is an aerosol formulation. In some embodiments, the nasal anti-CD3 antibody formulation is suitable for once daily administrations. In some embodiments, the nasal anti-CD3 antibody formulation provides for aerosol of an anti-CD3 antibody at a dosage in the range of about 0.1 mg to about 10 mg once a day. In some embodiments, the nasal anti-CD3 antibody formulation provides for aerosol of an anti-CD3 antibody fragment at a dosage in the range of about 0.1 mg to about 10 mg once a day. In some embodiments, the nasal anti-CD3 antibody formulation provides for aerosol of an anti-CD3 antibody at a dosage in the range of about 0.1 mg to about 10 mg once a day.

In some embodiments, the nasal anti-CD3 antibody formulation comprises a population of particles having a particle size in the range of about 1 mm to about 5 mm.

Particles of a particle formulation have diameters of between about 1 mm to about 5 mm, e.g., less than 5 mm in diameter, less than 4 mm in diameter, less than 3 mm in diameter, less than 2 mm in diameter, and about 1 mm in diameter.

Particles of a particle formulation comprising an anti-CD3 antibody or antigen-binding fragment thereof have average diameters of between about 0.1 mm to about 50 mm. Particles of a particle formulation comprising an anti-CD3 antibody or antigen-binding fragment thereof have average diameters of between about 1 mm to about 10 mm, e.g., less than 10 mm in average diameter, less than 9 mm in average diameter, less than 8 mm in average diameter, less than 7 mm in average diameter, less than 6 mm in average diameter, less than 5 mm in average diameter, less than 4 mm in average diameter, less than 3 mm in average diameter, and about 2 mm in average diameter. In some embodiments, particles have average diameters of between about 2 mm and 5 mm. In some embodiments, the particles have an average diameter between 2 mm and 5 mm, where each particle is less than about 50 mm in diameter.

In some embodiments, the nasal anti-CD3 antibody formulation includes a full length anti-CD3 antibody. In some embodiments, the nasal anti-CD3 antibody formulation includes an antibody fragment that specifically binds CD3. In some embodiments, the nasal anti-CD3 antibody formulation includes a combination of full-length anti-CD3 antibodies and antigen binding fragments that specifically bind CD3.

In some embodiments, the nasal anti-CD3 antibody formulation includes a solution comprising an anti-CD3 antibody at a dosage in the range of about 0.1 mg to about 10 mg, a citrate buffer at a concentration in the range of about 25 mm to about 50 mm, and a salt at a concentration of about 150 mm, where the solution has a pH in the range of about 4 to 6.

In some embodiments, the nasal anti-CD3 antibody formulation includes a solution comprising an anti-CD3 antibody at a dosage in the range of about 0.1 mg to about 10 mg, a sodium citrate buffer at a concentration in the range of about 25 mm to about 50 mm, and sodium chloride at a concentration of about 150 mm, where the solution has a pH in the range of about 4 to 6.

In some embodiments, the nasal anti-CD3 antibody formulation includes a solution comprising an anti-CD3 antibody fragment at a dosage in the range of about 0.1 mg to about 10 mg, a citrate buffer at a concentration in the range of about 25 mm to about 50 mm, and a salt at a concentration of about 150 mm, where the solution has a pH in the range of about 4 to 6. In some embodiments, the nasal anti-CD3 antibody formulation includes a solution comprising an anti-CD3 antibody fragment at a dosage in the range of about 0.1 mg to about 10 mg, a sodium citrate buffer at a concentration in the range of about 25 mm to about 50 mm, and sodium chloride at a concentration of about 150 mm, where the solution has a pH in the range of about 4 to 6.

In some embodiments, the nasal anti-CD3 antibody formulation includes a solution comprising a full-length NI-0401 antibody at a dosage in the range of about 0.1 mg to about 10 mg, a citrate buffer at a concentration in the range of about 25 mm to about 50 mm, and a salt at a concentration of about 150 mm, where the solution has a pH in the range of about 4 to 6. In some embodiments, the nasal anti-CD3 antibody formulation includes a solution comprising a full-length NI-0401 antibody at a dosage in the range of about 0.1 mg to about 10 mg, a sodium citrate buffer at a concentration in the range of about 25 mm to about 50 mm, and sodium chloride at a concentration of about 150 mm, where the solution has a pH in the range of about 4 to 6.

In some embodiments, the nasal anti-CD3 antibody formulation includes a solution comprising a NI-0401 antibody fragment at a dosage in the range of about 0.1 mg to about 10 mg, a citrate buffer at a concentration in the range of about 25 mm to about 50 mm, and a salt at a concentration of about 150 mm, where the solution has a pH in the range of about 4 to 6. In some embodiments, the nasal anti-CD3 antibody formulation includes a solution comprising a NI-0401 antibody fragment at a dosage in the range of about 0.1 mg to about 10 mg, a sodium citrate buffer at a concentration in the range of about 25 mm to about 50 mm, and sodium chloride at a concentration of about 150 mm, where the solution has a pH in the range of about 4 to 6.

In some embodiments, the nasal anti-CD3 antibody formulation includes one or more polyols as stabilizing excipients. In some embodiments, the polyol is mannitol at a concentration in the range of about 0.1% to about 10%. In some embodiments, the polyol is trehalose at a concentration in the range of about 0.1% to about 1%. In some embodiments, the polyol is sorbitol at a concentration in the range of about 1% to about 10%. In some embodiments, the polyol is glycerol at a concentration in the range of about 1% to about 10%. In some embodiments, the polyol is mannitol at a concentration in the range of about 0.1% to about 10%, and trehalose at a concentration in the range of about 0.1% to about 1%. In some embodiments, the polyol is mannitol at a concentration in the range of about 0.1% to about 10%, and sorbitol at a concentration in the range of about 1% to about 10%. In some embodiments, the nasal anti-CD3 antibody formulation includes one or more polyols as stabilizing excipients, and glycerol at a concentration in the range of about 1% to about 10%. In some embodiments, the polyol is trehalose at a concentration in the range of about 0.1% to about 1%, and sorbitol at a concentration in the range of about 1% to about 10%. In some embodiments, the polyol is trehalose at a concentration in the range of about 0.1% to about 1%, and glycerol at a concentration in the range of about 1% to about 10%. In some embodiments, the polyol is sorbitol at a concentration in the range of about 1% to about 10%, and glycerol at a concentration in the range of about 1% to about 10%. In some embodiments, the polyol is mannitol at a concentration in the range of about 0.1% to about 10%, trehalose at a concentration in the range of about 0.1% to about 1%, and sorbitol at a concentration in the range of about 1% to about 10%. In some embodiments, the polyol is mannitol at a concentration in the range of about 0.1% to about 10%, trehalose at a concentration in the range of about 0.1% to about 1%, and glycerol at a concentration in the range of about 1% to about 10%. In some embodiments, the polyol is trehalose at a concentration in the range of about 0.1% to about 1%, sorbitol at a concentration in the range of about 1% to about 10%, and glycerol at a concentration in the range of about 1% to about 10%. In some embodiments, the polyol is mannitol at a concentration in the range of about 0.1% to about 10%, trehalose at a concentration in the range of about 0.1% to about 1%, sorbitol at a concentration in the range of about 1% to about 10%, and the polyol is glycerol at a concentration in the range of about 1% to about 10%.

In some embodiments, the nasal anti-CD3 antibody formulation includes one or more surfactants such as, by way of non-limiting example, Polysorbate 20 or Polysorbate 80. In some embodiments, the Polysorbate 20 or Polysorbate 80 is present at a concentration in the range of about 0.01% to about 0.05%.

In some embodiments, the nasal anti-CD3 antibody formulation is suitable for storage at about 2° C. to about 4° C. In some embodiments, the nasal anti-CD3 antibody formulation is stored in a sealed vial or other suitable container. In some embodiments, the nasal anti-CD3 antibody formulation is stored in a sealed vial or other suitable container at about 2° C. to about 4° C.

It will be appreciated that administration of therapeutic entities in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic Administration

Therapeutic formulations provided herein, which include an anti-CD3 antibody formulation disclosed herein, are used to treat or alleviate a symptom associated with an immune-related disorder, such as, for example, an autoimmune disease or an inflammatory disorder. The anti-CD3 antibody formulation disclosed herein are also used to treat or alleviate a symptom associated with a neurodegenerative disorder or cancer.

Autoimmune diseases include, for example, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis juvenile, discoid lupus, essential mixed cryoglobulinemia, experimental autoimmune encephalomyelitis (EAE), fibromyalgia-fibromyositis, Graves' disease, Guillain-Barré syndrome, Hashimoto's thyroiditis, idiopathic pulmonary fibrosis, idiopathic thrombocytopenia purpura (ITP), IgA nephropathy, insulin-dependent diabetes mellitus (Type I diabetes; Type 2 diabetes), juvenile chronic arthritis (Still's disease), juvenile rheumatoid arthritis, Ménière's disease, mixed connective tissue disease, multiple sclerosis, myasthenia gravis, nonalcoholic steatohepatitis (NASH), pernacious anemia, polyarteritis *nodosa*, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjögren's syndrome, stiff-man syndrome, systemic lupus erythematosus, Takayasu arteritis, temporal arteritis/giant cell arteritis, ulcerative colitis, uveitis, vitiligo and Wegener's granulomatosis.

Inflammatory disorders, include, for example, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, inflammatory bowel disease (IBD), nonalcoholic fatty liver disease (NAFLD), osteoarthritis, sepsis, stroke, transplantation of tissue and organs, vasculitis, diabetic retinopathy and ventilator induced lung injury.

The formulations of anti-CD3 antibody are administered to a subject suffering from an immune-related disorder, such as an autoimmune disease or an inflammatory disorder a neurodegenerative disorder or cancer. A subject suffering from an autoimmune disease, an inflammatory disorder, neurodegenerative disorder or cancer is identified by methods known in the art. For example, subjects suffering from an autoimmune disease such as Crohn's disease, ulcerative colitis or inflammatory bowel disease, are identified using any of a variety of clinical and/or laboratory tests such as, physical examination, radiologic examination, and blood, urine and stool analysis to evaluate immune status. For example, patients suffering from multiple sclerosis are identified, e.g., by using magnetic resonance imaging the presence of central nervous system (CNS) lesions that are disseminated in time and space (i.e., occur in different parts of the CNS at least three months apart). Patients suffering from rheumatoid arthritis are identified using, e.g., blood tests and/or x-ray or other imaging evaluation. Patients suffering from Type I diabetes are identified, e.g., when any three of these tests is positive, followed by a second positive test on a different day: (1) fasting plasma glucose of greater than or equal to 126 mg/dl with symptoms of diabetes; (2) casual plasma glucose (taken at any time of the day) of greater than or equal to 200 mg/dl with the symptoms of diabetes; or (3) oral glucose tolerance test (OGTT) value of greater than or equal to 200 mg/dl measured at a two-hour interval (the OGTT is given over a three-hour time span).

Administration of an anti-CD3 antibody formulation to a patient suffering from an immune-related disorder such as an autoimmune disease, an inflammatory disorder, neurodegenerative disorder or cancer is considered successful if any of a variety of laboratory or clinical results is achieved. For example, administration of an anti-CD3 antibody formulation to a patient suffering from an immune-related disorder such as an autoimmune disease or an inflammatory disorder is considered successful if one or more of the symptoms associated with the disorder is alleviated, reduced, inhibited or does not progress to a further, i.e., worse, state. Administration of an anti-CD3 antibody formulation to a patient suffering from an immune-related disorder such as an autoimmune disease or an inflammatory disorder is considered successful if the disorder, e.g., an autoimmune disorder, enters remission or does not progress to a further, i.e., worse, state.

In another embodiment, the anti-CD3 antibody formulations provided herein are used in the treatment, diagnosis and/or prevention of nonalcoholic steatohepatitis (NASH). Non-alcoholic steatohepatitis is fatty liver disease due to causes other than alcohol. NASH is associated with symptoms such as anemia; fatigue; weight loss; weakness, and in later stages, cirrhosis. The anti-CD3 antibody formulations provided herein are administered to a subject that is suffering from, has been diagnosed with, or is predisposed to NASH. The anti-CD3 antibody formulations provided herein are administered at a dosage that is sufficient to alleviate at least one symptom of NASH, to treat NASH, to prevent NASH, and/or to prevent NASH from progressing to a further disease state in a subject.

The anti-CD3 antibody formulations provided herein are used in the treatment, diagnosis and/or prevention of inflammatory bowel disorder (IBD). IBD is the chronic inflammation and irritation of tissue in the gastrointestinal (GI) tract. IBD is associated with symptoms such as abdominal cramping and pain, diarrhea, rectal bleeding, fever and elevated white blood cell count. The anti-CD3 antibody formulations provided herein are administered to a subject that is suffering from, has been diagnosed with, or is predisposed to IBD. The anti-CD3 antibody formulations provided herein are administered at a dosage that is sufficient to alleviate at least one symptom of IBD, to treat IBD, to prevent IBD, and/or to prevent IBD from progressing to a further disease state in a subject.

In another embodiment, the anti-CD3 antibody formulations provided herein are used in the treatment, diagnosis and/or prevention of ulcerative colitis. Ulcerative colitis is the chronic inflammation and irritation of the colon. Ulcerative colitis is associated with symptoms such as anemia; fatigue; weight loss; loss of appetite; rectal bleeding; loss of body fluids and nutrients; skin lesions; joint pain; and growth failure (specifically in children). The anti-CD3 antibody formulations provided herein are administered to a subject that is suffering from, has been diagnosed with, or is predisposed to ulcerative colitis. The anti-CD3 antibody formulations provided herein are administered at a dosage that is sufficient to alleviate at least one symptom of ulcerative colitis, to treat ulcerative colitis, to prevent ulcerative colitis, and/or to prevent ulcerative colitis from progressing to a further disease state in a subject.

In another embodiment, the anti-CD3 antibody formulations provided herein are used in the treatment, diagnosis and/or prevention of Crohn's disease. Crohn's disease is the chronic inflammation and irritation of the intestines. Crohn's disease is associated with symptoms such as abdominal pain, diarrhea, weight loss, poor appetite, fever, night sweats, rectal pain, and rectal bleeding. The anti-CD3 antibody formulations provided herein are administered to a subject that is suffering from, has been diagnosed with, or is predisposed to Crohn's disease. The anti-CD3 antibody formulations provided herein are administered at a dosage that is sufficient to alleviate at least one symptom of Crohn's disease, to treat Crohn's disease, to prevent Crohn's disease, and/or to prevent Crohn's disease from progressing to a further disease state in a subject.

In another embodiment, the anti-CD3 antibody formulations provided herein are used in the treatment, diagnosis and/or prevention of multiple sclerosis (MS). MS is a chronic, inflammatory disease that affects the central nervous system (CNS). Symptoms of MS include, for example, changes in sensation, visual problems, muscle weakness, depression, difficulties with coordination and speech, and pain. The anti-CD3 antibody formulations provided herein are administered to a subject that is suffering from, has been diagnosed with, or is predisposed to MS. The anti-CD3 antibody formulations provided herein are administered at a dosage that is sufficient to alleviate at least one symptom of MS, to treat MS, to prevent MS, and/or to prevent MS from progressing to a further disease state in a subject.

In another embodiment, the anti-CD3 antibody formulations provided herein are used in the treatment, diagnosis and/or prevention of Lupus. Lupus is a chronic inflammatory disease that occurs when your body's immune system attacks your own tissues and organs. Inflammation caused by lupus can affect many different body systems—including your joints, skin, kidneys, blood cells, brain, heart and lungs. The signs and symptoms of lupus that you experience will depend on which body systems are affected by the disease. The most common signs and symptoms include: fatigue and fever, joint pain, stiffness and swelling, butterfly-shaped rash on the face that covers the cheeks and bridge of the nose, skin lesions that appear or worsen with sun exposure (photosensitivity), fingers and toes that turn white or blue when exposed to cold or during stressful periods (Raynaud's phenomenon), shortness of breath, chest pain, dry eyes, headaches, confusion and memory loss. The anti-CD3 antibody formulations provided herein are administered to a subject that is suffering from, has been diagnosed with, or is predisposed to Lupus. The anti-CD3 antibody formulations provided herein are administered at a dosage that is sufficient to alleviate at least one symptom of Lupus, to treat Lupus, to prevent Lupus, and/or to prevent Lupus from progressing to a further disease state in a subject.

In another embodiment, the anti-CD3 antibody formulations provided herein are used in the treatment, diagnosis and/or prevention of experimental autoimmune encephalomyelitis (EAE). EAE is a chronic, inflammatory disease that affects the central nervous system (CNS). The anti-CD3 antibody formulations provided herein are administered at a dosage that is sufficient to alleviate at least one symptom of EAE, to treat EAE, to prevent EAE, and/or to prevent MS from progressing to a further disease state in a subject.

In another embodiment, the anti-CD3 antibody formulations provided herein are used in the treatment, diagnosis and/or prevention of insulin-dependent diabetes mellitus (Type I diabetes). Type I diabetes is a disease characterized by persistent hyperglycemia (high blood sugar levels) resulting from inadequate secretion of the hormone insulin. Type I diabetes is characterized by loss of the insulin-producing beta cells of the islets of Langerhans of the pancreas. Type I diabetes is an autoimmune disorder, in which the body's own immune system attacks the beta cells in the Islets of Langerhans of the pancreas, destroying them or damaging them sufficiently to reduce or eliminate insulin production. Symptoms of Type I diabetes include, for example, increased thirst, increased urination, weight loss despite increased appetite, nausea, vomiting, abdominal pain, and fatigue. The anti-CD3 antibody formulations provided herein are administered to a subject that is suffering from, has been diagnosed with, or is predisposed to Type I diabetes. The anti-CD3 antibody formulations provided herein are administered at a dosage that is sufficient to alleviate at least one symptom of Type I diabetes, to treat Type I diabetes, to prevent Type I diabetes, and/or to prevent Type I diabetes from progressing to a further disease state in a subject.

In another embodiment, the anti-CD3 antibody formulations provided herein are used in the treatment, diagnosis and/or prevention of Type II diabetes. Type II diabetes is a disease is a long-term metabolic disorder that is characterized by high blood sugar, insulin resistance, and relative lack of insulin. Common symptoms include increased thirst, frequent urination, and unexplained weight loss. Symptoms may also include increased hunger, feeling tired, and sores that do not heal. Often symptoms come on slowly. Long-term complications from high blood sugar include heart disease, strokes, diabetic retinopathy which can result in blindness, kidney failure, and poor blood flow in the limbs which may lead to amputations. The sudden onset of hyperosmolar hyperglycemic state may occur; however, ketoacidosis is uncommon. The anti-CD3 antibody formulations provided herein are administered to a subject that is suffering from, has been diagnosed with, or is predisposed to Type II diabetes. The anti-CD3 antibody formulations provided herein are administered at a dosage that is sufficient to alleviate at least one symptom of Type II diabetes, to treat Type II diabetes, to prevent Type II diabetes, and/or to prevent Type II diabetes from progressing to a further disease state in a subject.

In another embodiment, the anti-CD3 antibody formulations provided herein are used in the treatment, diagnosis and/or prevention of rheumatoid arthritis (RA). Rheumatoid arthritis is an autoimmune disease that causes chronic inflammation of the joints. Rheumatoid arthritis can also cause inflammation of the tissue around the joints, as well as other organs in the body. RA is associated with symptoms such as fatigue, lack of appetite, low grade fever, muscle and joint aches, and stiffness. The anti-CD3 antibody formulations provided herein are administered to a subject that is suffering from, has been diagnosed with, or is predisposed to RA. The anti-CD3 antibody formulations provided herein are administered at a dosage that is sufficient to alleviate at least one symptom of RA, to treat RA, to prevent RA, and/or to prevent RA from progressing to a further disease state in a subject.

The present invention also provides methods of treating or alleviating a symptom associated with an immune-related disorder or a symptom associated with rejection following organ transplantation. For example, the formulations used herein are used to treat or alleviate a symptom of any of the autoimmune diseases and inflammatory disorders provided herein.

The therapeutic formulations used herein are also used as immunosuppression agents in organ or tissue transplantation. As used herein, "immunosuppression agent" refers to an agent whose action on the immune system leads to the immediate or delayed reduction of the activity of at least one pathway involved in an immune response, whether this response is naturally occurring or artificially triggered, whether this response takes place as part of the innate immune system, the adaptive immune system, or both. These immunosuppressive anti-CD3 antibody formulations are administered to a subject prior to, during and/or after organ or tissue transplantation. For example, an anti-CD3 antibody formulation provided herein is used to treat or prevent rejection after organ or tissue transplantation.

In yet another embodiment used herein, an anti-CD3 antibody formulation is administered to a human individual upon detection of the presence of auto-reactive antibodies within the human individual. Such auto-reactive antibodies are known within the art as antibodies with binding affinity to one or more proteins expressed endogenously within the human individual. In one aspect used herein, the human individual is tested for the presence of auto-reactive antibodies specifically involved in one or more autoimmune diseases as are well known within the art. In one specific embodiment, a human patient is tested for the presence of antibodies against insulin, glutamic acid decarboxylase and/or the IA-2 protein, and subsequently administered with an anti-CD3 antibody upon positive detection of one or more such auto-reactive antibodies.

In yet another embodiment used herein, an anti-CD3 formulation is administered to a human individual to activate mucosal immunity and immunomodulation.

The anti-CD3 antibody formulation is used to activate regulatory T-cells (Tregs).

In another embodiment used herein, an anti-CD3 antibody composition is administered to human subjects to prevent, reduce or decrease the recruitment of immune cells into human tissues. An anti-CD3 antibody used herein is administered to a subject in need thereof to prevent and treat conditions associated with abnormal or deregulated immune cell recruitment into tissue sites of human disease.

In another embodiment used herein, an anti-CD3 antibody composition is administered to human subjects to prevent, reduce or decrease the extravasation and diapedesis of immune cells into human tissues. Thus, the anti-CD3 antibodies used herein are administered to prevent and/or treat conditions associated with abnormal or deregulated immune cell infiltration into tissue sites of human disease.

In another embodiment used herein, an anti-CD3 antibody composition is administered to human subjects to prevent, reduce or decrease the effects mediated by the release of cytokines within the human body. The term "cytokine" refers to all human cytokines known within the art that bind extracellular receptors upon the cell surface and thereby modulate cell function, including but not limited to IL-2, IFN-g, TNF-a, IL-4, IL-5, IL-6, IL-9, IL-10, and IL-13.

In another embodiment used herein, an anti-CD3 antibody composition is administered to human subjects to prevent, reduce or decrease the effects mediated by the release of cytokine receptors within the human body. The term "cytokine receptor" refers to all human cytokine receptors within the art that bind one or more cytokine(s), as defined herein, including but not limited to receptors of the aforementioned cytokines. Thus, an anti-CD3 antibody used herein is administered to treat and/or prevent conditions mediated through abnormal activation, binding or ligation of one or more cytokine receptor(s) within the human body. It is further envisioned that administration of the anti-CD3 antibody in vivo will deplete the intracellular signaling mediated by cytokine receptor(s) within such human subject.

In one aspect used herein, an anti-CD3 antibody composition is administered to a human individual upon decrease of pancreatic beta-cell function therein. In one embodiment, the individual is tested for beta-cell function, insulin secretion or c-peptide levels as are known within the art. Subsequently, upon notice of sufficient decrease of either the indicator, the human individual is administered with a sufficient dosage regimen of an anti-CD3 antibody to prevent further progression of autoimmune destruction of beta-cell function therein.

Preferably, the therapeutic anti-CD3 antibody formulations provided herein are administered to a subject oral, subcutaneously or nasally. Other routes of administration are contemplated. For example, the anti-CD3 antibody formulations are administered intravenously, intramuscularly, or any combination of these routes of administration.

Combination Therapy

The anti-CD3 antibody formulation is administered during and/or after treatment in combination with one or more additional agents such as, for example, a chemotherapeutic agent, an anti-inflammatory agent, and/or a an immunosuppressive agent.

In some embodiments, the anti-CD3 antibody formulation and the additional agent are formulated into a single therapeutic composition, and the anti-CD3 antibody formulation and additional agent are administered simultaneously.

Alternatively, the anti-CD3 antibody formulation and additional agent are separate from each other, e.g., each is formulated into a separate therapeutic composition, and the anti-CD3 antibody formulation and the additional agent are administered simultaneously, or the anti-CD3 antibody formulation and the additional agent are administered at different times during a treatment regimen. For example, the anti-CD3 antibody formulation is administered prior to the administration of the additional agent, the anti-CD3 antibody formulation is administered subsequent to the administration of the additional agent, or the anti-CD3 antibody formulation and the additional agent are administered in an alternating fashion. As described herein, the anti-CD3 antibody formulation and additional agent are administered in single doses or in multiple doses.

In some embodiments, the anti-CD3 antibody formulation and the additional agent(s) are administered simultaneously. For example, the anti-CD3 antibody formulation and the additional agent(s) can be formulated in a single composition or administered as two or more separate compositions.

In some embodiments, the anti-CD3 antibody formulation and the additional agent(s) are administered sequentially, or the anti-CD3 antibody formulation and the additional agent are administered at different times during a treatment regimen.

Administration of an anti-CD3 antibody formulation, alone or in combination with one or more additional agents, to a patient suffering from an autoimmune disease, inflammation disorder, a neurodegenerative disorder or cancer is considered successful if any of a variety of laboratory or clinical objectives is achieved. For example, administration of an anti-CD3 antibody formulation, alone or in combination with one or more additional agents, to a patient suffering from an autoimmune disease, inflammation disorder, a neurodegenerative disorder or cancer is considered successful if one or more of the symptoms associated with the disease or disorder is alleviated, reduced, inhibited or does not progress to a further, i.e., worse, state. Administration of an anti-CD3 antibody formulation, alone or in combination with one or more additional agents, to a patient suffering from an autoimmune disease, inflammation disorder, a neurodegenerative disorder or cancer is considered successful if the disease or disorder enters remission or does not progress to a further, i.e., worse, state.

Second agents suitable for use with the compositions and methods of the present invention include for example, an NF-kB inhibitor, a GLP-1 or a beta cell resting compound, mesalamine or another 5-ASA drug, pentoxifylline, ursodeoxycholic acid, a PPARγ agonist, All Trans Retinoic Acid (ATRA), DPP-4 (gliptins-sitagliptin), a fatty acid synthesis inhibitor (e.g., cerulenin, quercetin, C7, apigenin, AICAR), a FXR agonist (e.g., bile salt activators, chenodeoxycholic acid, Obeticholic acid (OIBA, Ocaliva), fexaramine, cafestol, bile Acid Sequestrants (cholestyramine, cholestipol, coleserelam), SGLT2 inhibitors (ex-dapagliflozin (reduce HbA1c levels), an anti-IL-6R mAb, anti-TNF antibody (Remicade® (Infliximab), and Humira® (Adalimumab), Enbrel® (Etanercept) anti-inflammatory and/or immunosuppressive compounds (e.g., methotrexate, cyclosporin A cyclosporin microemulsion), tacrolimus, corticosteroids, statins, interferon beta, glatiramer acetate (Copaxone), interferon beta-1a (Avonex), interferon beta-1a (Rebif), interferon beta-1b (Betaseron or Betaferon), mitoxantrone (Novantrone), dexamethasone (Decadron), methylprednisolone (Depo-Medrol), prednisone (Deltasone) or an anti-obesity drug.

In some embodiments, the combination therapy that includes an anti-CD3 antibody formulation and at least a second therapeutic agent is used in the treatment of ulcerative colitis. In some embodiments, the underlying gastric inflammation associated with ulcerative colitis is suppressed prior to administration of the anti-CD3 antibody formulation. In some embodiments, the underlying gastric inflammation associated with ulcerative colitis is suppressed prior to administration of the additional therapeutic agent(s). In some embodiments, the underlying gastric inflammation associated with ulcerative colitis is suppressed prior to administration of the anti-CD3 antibody formulation and the additional therapeutic agent(s). In some embodiments, the subject to be treated is pre-treated with an anti-inflammatory agent that is dosed prior to treatment with the anti-CD3 antibody formulation. In some embodiments, the subject to be treated is pre-treated with an anti-inflammatory agent that is dosed prior to treatment with the additional agent(s). In some embodiments, the subject to be treated is pre-treated with an anti-inflammatory agent that is dosed prior to treatment with the anti-CD3 antibody formulation and the additional agent(s).

In some embodiments, the second agent is an anti-interleukin 6R (IL-6R) agent, such as for example, an anti-IL-6R antibody or fragment thereof. In some embodiments, the second agent is one or more anti-inflammatory agent(s). In some embodiments, the second agent is an NF-kB inhibitor.

In some embodiments, the second agent is All Trans Retinoic Acid (ATRA). ATRA is produced at high levels in the intestine and it plays important roles in mucosal immunity and immune tolerance. RA at basal levels is required for immune cell survival and activation. ATRA is also known to help in regulator T cell (Treg) differentiation.

In some embodiments, the second agent is mesalamine or another 5-ASA drug. In some embodiments, the combination therapy that includes an anti-CD3 antibody formulation and mesalamine or another 5-ASA drug is administered once daily throughout the treatment regimen.

In some embodiments, the second agent is an anti-tumor necrosis factor (TNF) antibody. Any suitable anti-TNF antibody or antigen-binding fragment thereof can be used in the combination therapies that include anti-CD3 antibody formulation of the disclosure, including, by way of non-limiting example, Remicade® and Humira®.

In some embodiments the second agent is, GLP-1 or a beta cell resting compound (i.e., a compound that reduces or otherwise inhibits insulin release, such as potassium channel openers). Examples of suitable GLP-1 compounds are described in e.g., the published application U.S. 20040037826, and suitable beta cell resting compounds are described in published application U.S. 20030235583, each of which is hereby incorporated by reference in its entirety.

In another embodiment, the anti-CD3 antibody formulations used to treat an immune-related disorder are administered in combination with any of a variety of known anti-inflammatory and/or immunosuppressive compounds. Suitable known compounds include, but are not limited to methotrexate, cyclosporin A (including, for example, cyclosporin microemulsion), tacrolimus, corticosteroids, statins, interferon beta, Remicade (Infliximab), Enbrel (Etanercept) and Humira (Adalimumab).

For example, in the treatment of rheumatoid arthritis, the anti-CD3 antibody formulations used herein can be co-administered with corticosteroids, methotrexate, cyclosporin A, statins, an anti-IL-6R antibody, Remicade (Infliximab), Enbrel (Etanercept) and/or Humira (Adalimumab).

In the treatment of uveitis, the anti-CD3 antibody formulations can be administered in conjunction with, e.g., corticosteroids, methotrexate, cyclosporin A, cyclophosphamide and/or statins. Likewise, patients afflicted with a disease such as Crohn's Disease or psoriasis can be treated with a combination of an anti-CD3 antibody composition used herein and Remicade (Infliximab), an anti-IL-6R antibody, and/or Humira (Adalimumab).

Patients with multiple sclerosis can receive a combination of an anti-CD3 antibody composition used herein in combination with, e.g., glatiramer acetate (Copaxone), interferon beta-1a (Avonex), interferon beta-1a (Rebif), interferon beta-1b (Betaseron or Betaferon), mitoxantrone (Novantrone), an anti-IL-6R antibody, dexamethasone (Decadron), methylprednisolone (Depo-Medrol), and/or prednisone (Deltasone) and/or statins.

In one embodiment, the immunosuppressive anti-CD3 antibody formulations used herein are administered in conjunction with a second agent such as, for example, GLP-1 or a beta cell resting compound, as described above.

In another embodiment, these immunosuppressive anti-CD3 antibody formulations are administered in combination with any of a variety of known anti-inflammatory and/or immunosuppressive compounds. Suitable anti-inflammatory and/or immunosuppressive compounds for use with the anti-CD3 antibodies used herein include, but are not limited to, methotrexate, cyclosporin A (including, for example, cyclosporin microemulsion), tacrolimus, corticosteroids and statins.

Figure 34:
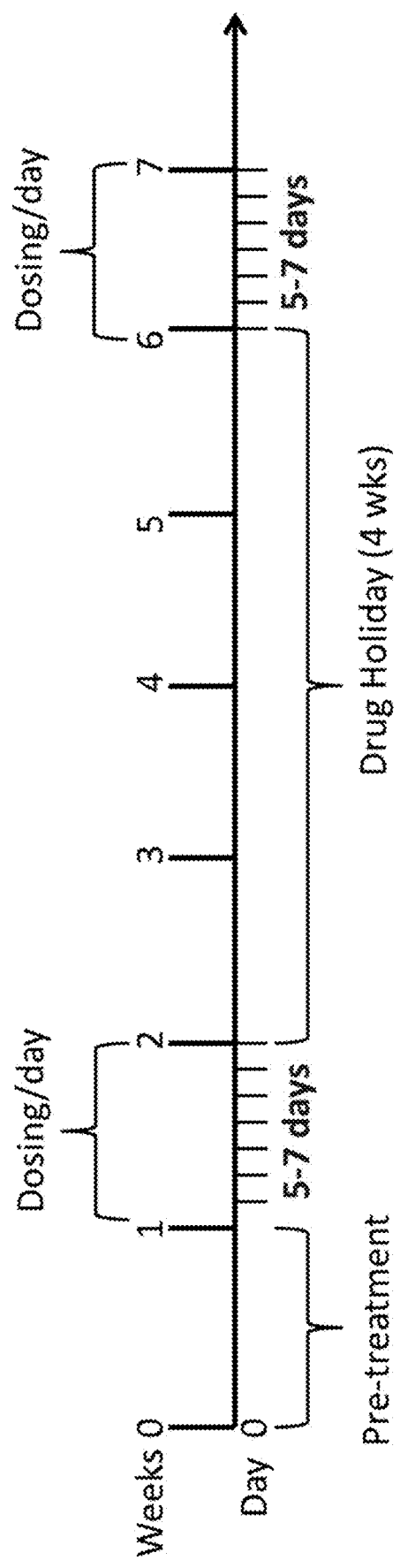
FIG. 34 is a schematic representation of a dosing regimen and drug holiday cycle for a combination therapy using anti-CD3 antibody formulation of the present disclosure and at least a second agent for the treatment of ulcerative colitis.

In some embodiments, the combination therapy that includes an anti-CD3 antibody formulation and at least a second therapeutic agent is administered in a dosing regimen shown in FIG. 34. In some embodiments, the combination therapy that includes an anti-CD3 antibody formulation and at least a second therapeutic agent is administered in a dosing regimen shown in FIG. 34, and the dosing regimen is repeated. In some embodiments, the combination therapy that includes an anti-CD3 antibody formulation and at least a second therapeutic agent is administered in a dosing regimen shown in FIG. 34, and the dosing regimen is repeated after the drug holiday period. In some embodiments, the combination therapy that includes an anti-CD3 antibody formulation and at least a second therapeutic agent is administered in a dosing regimen shown in FIG. 34, and the drug holiday cycle is repeated. In some embodiments, the combination therapy that includes an anti-CD3 antibody formulation and at least a second therapeutic agent is administered in a dosing regimen shown in FIG. 34, and the dosing regimen and drug holiday cycle are repeated. In some of the above-embodiments, the second agent is selected from the group consisting of ATRA, mesalamine or other 5-ASA drug, and an anti-TNF antibody or antigen binding fragment thereof.

In some embodiments, the combination therapy that includes an anti-CD3 antibody formulation and at least a second therapeutic agent is used in the treatment of Nonalcoholic Steatohepatitis (NASH). NASH is an autoimmune disease that is associated with severe underlying liver fibrosis due to excessive fat deposit. The natural bile acid, chenodeoxycholic acid, is the most active physiological ligand for the farnesoid X receptor (FXR), which is involved in many physiological and pathological processes. Obeticholic acid is the first FXR agonist to be used in human drug studies. However, therapeutic utility of OBA may be limited to a sub-set of patients. OBA does not suppress autoimmune disorder. Hence, combinations of an FXR agonist with the anti-CD3 antibody formulations of the present disclosure produce synergistic effects when administered in combination.

In some embodiments, the second agent is metformin. In some embodiments, the second agent is metformin administered at a dose of about 500 mg BID for 44 weeks of treatment.

In some embodiments, the second agent is pentoxyfillin. In some embodiments, the second agent is pentoxyfillin administered at a dose of about 400 mg 3×/day or about 600 mg BID for 52 weeks of treatment.

In some embodiments, the second agent is ursodeoxycholic acid. In some embodiments, the second agent is ursodeoxycholic acid administered at a dose of about 10 mg/kg/day to about 20 mg/kg/day for 52 weeks of treatment.

In some embodiments, the second agent is obeticholic acid. In some embodiments, the second agent is obeticholic acid administered at a dose of about 10 mg/kg/day to about 20 mg/kg/day for 52 weeks of treatment.

Figure 35:
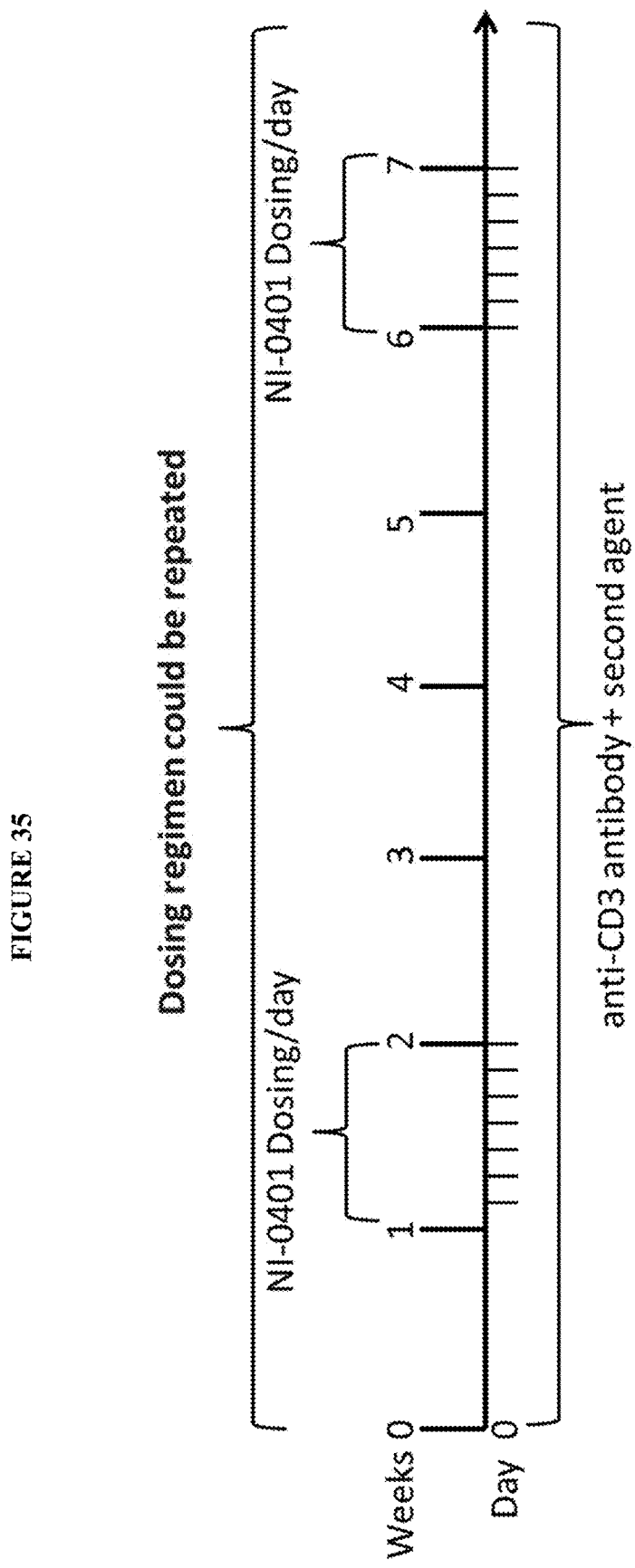
FIG. 35 is a schematic representation of a dosing regimen and drug holiday cycle for a combination therapy using anti-CD3 antibody formulation of the present disclosure and at least a second agent for the treatment of Nonalcoholic Steatohepatitis (NASH).

In some embodiments, the combination therapy that includes an anti-CD3 antibody formulation and at least a second therapeutic agent is administered in a dosing regimen shown in FIG. 35. In some embodiments, the combination therapy that includes an anti-CD3 antibody formulation and at least a second therapeutic agent is administered in a dosing regimen shown in FIG. 35, and the dosing regimen is repeated. In some embodiments, the combination therapy that includes an anti-CD3 antibody formulation and at least a second therapeutic agent is administered in a dosing regimen shown in FIG. 35, and the drug holiday cycle is repeated. In some embodiments, the combination therapy that includes an anti-CD3 antibody formulation and at least a second therapeutic agent is administered in a dosing regimen shown in FIG. 35, and the dosing regimen and drug holiday cycle are repeated. In some embodiments, the combination therapy that includes an anti-CD3 antibody formulation and at least a second therapeutic agent is administered in a dosing regimen shown in FIG. 35, and the dosing regimen is repeated with the following schedule: 5-7 days on, 21-28 days off. In some of the above embodiments, the second agent is selected from the group consisting of metformin, pentoxyfillin, ursodeoxycholic acid, obeticholic acid, and combinations thereof. In some of the above embodiments, the second agent is metformin administered at 500 mg BID for 44 weeks of treatment. In some of the above embodiments, the second agent is pentoxifylline administered at a dose of 400 mg 3×/day or 600 mg BID for 52 weeks of treatment. In some of the above embodiments, the second agent is ursodeoxycholic acid administered at a dose of 10-20 mg/kg/day for 52 weeks of treatment. In some of the above embodiments, the second agent is obeticholic acid administered at a dose of 10-20 mg/kg/day for 52 weeks of treatment.

In some embodiments, the combination therapy that includes an anti-CD3 antibody formulation and at least a second therapeutic agent is used in the treatment of type I diabetes. In some embodiments, the second agent is any art-recognized agent useful in the treatment of type I diabetes and/or type II diabetes. In some embodiments, the second agent is metformin. In some embodiments, the second agent is metformin, and the anti-CD3 antibody formulation is an oral formulation. In some embodiments, the second agent is metformin, and the anti-CD3 antibody formulation is an oral capsule formulation. In some embodiments, the metformin is administered at dose of about 500 mg BID. In some embodiments, the metformin is administered at dose of about 500 mg BID, and the anti-CD3 formulation is administered in an amount such that the combination therapy reduces insulin dependency in the subject. In some embodiments, the metformin is administered at dose of about 500 mg BID, and the anti-CD3 formulation is administered is administered to specific patient population. In some embodiments, the metformin is administered at dose of about 500 mg BID, and the anti-CD3 formulation is administered to patients having serum levels of c-peptide in the range of about 0.1 nmol/L to about 0.4 nmol/L, HbA1c level of less than 7%, and/or insulin dependency in the range of about 0.25 U/kg/day.

Figure 36:
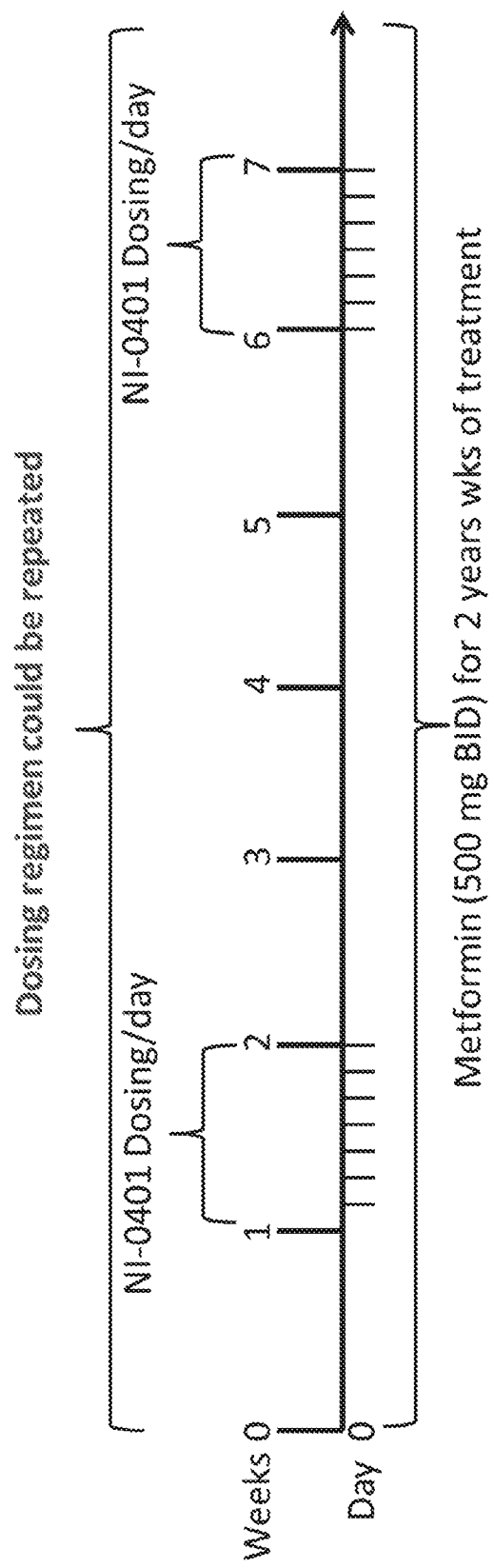
FIG. 36 is a schematic representation of a dosing regimen and drug holiday cycle for a combination therapy using anti-CD3 antibody formulation of the present disclosure and at least a second agent for the treatment of type I diabetes.

In some embodiments, the combination therapy that includes an anti-CD3 antibody formulation and at least a second therapeutic agent is administered in a dosing regimen shown in FIG. 36. In some embodiments, the combination therapy that includes an anti-CD3 antibody formulation and at least a second therapeutic agent is administered in a dosing regimen shown in FIG. 36, and the dosing regimen is repeated. In some embodiments, the combination therapy that includes an anti-CD3 antibody formulation and at least a second therapeutic agent is administered in a dosing regimen shown in FIG. 36, and the drug holiday cycle is repeated. In some embodiments, the combination therapy that includes an anti-CD3 antibody formulation and at least a second therapeutic agent is administered in a dosing regimen shown in FIG. 36, and the dosing regimen and drug holiday cycle are repeated. In some of the above-embodiments, the drug holiday period is based on the improvement of serum levels of c-peptide and/or reduction of HbA1c from the baseline. In some of the above-embodiments, the second agent is metformin.

The present disclosure also provides methods of using the anti-CD3 antibody formulations in various therapeutic indications, alone or in combination with at least one additional agent. In some embodiments, the anti-CD3 antibody formulations, alone or in combination with one or more additional agents, are useful in the treatment of an autoimmune disease and/or an inflammatory disorder.

In some embodiments, an oral anti-CD3 antibody formulation, alone or in combination with one or more additional agents, is used in a method of treating an autoimmune disease and/or an inflammatory disorder. In some embodiments, an oral anti-CD3 antibody formulation, alone or in combination with one or more additional agents, is used in a method of treating inflammatory bowel disorder (IBD). In some embodiments, an oral anti-CD3 antibody formulation, alone or in combination with one or more additional agents, is used in a method of treating graft vs. host disease (GvHD). In some embodiments, an oral anti-CD3 antibody formulation, alone or in combination with one or more additional agents, is used in a method of treating NASH. In some embodiments, an oral anti-CD3 antibody formulation, alone or in combination with one or more additional agents, is used in a method of treating type I diabetes.

In some embodiments, an oral anti-CD3 antibody formulation, alone or in combination with one or more additional agents, is used in a method of treating primary biliary cirrhosis (PBC). In some embodiments, an oral anti-CD3 antibody formulation, alone or in combination with one or more additional agents, is used in a method of treating Nonalcoholic Steatohepatitis (NASH).

In some embodiments, a subcutaneous anti-CD3 antibody formulation, alone or in combination with one or more additional agents, is used in a method of treating an autoimmune disease and/or an inflammatory disorder. In some embodiments, a subcutaneous anti-CD3 antibody formulation, alone or in combination with one or more additional agents, is used in a method of treating IBD. In some embodiments, a subcutaneous anti-CD3 antibody formulation, alone or in combination with one or more additional agents, is used in a method of treating GvHD. In some embodiments, a subcutaneous anti-CD3 antibody formulation, alone or in combination with one or more additional agents, is used in a method of treating type I diabetes.

In some embodiments, a subcutaneous anti-CD3 antibody formulation, alone or in combination with one or more additional agents, is used in a method of inhibiting rejection of and/or prolonging survival of transplanted biological material in a subject. The biological material to be transplanted is one or more cells or cell types, one or more tissues or tissue types, or an organ or portion thereof. For example, the biological material to be transplanted is allogeneic biological material. In some embodiments, the biological material to be transplanted is islet cells. In some embodiments, the islet cells are allogeneic islet cells. In some embodiments, the biological material to be transplanted is or is derived from kidney, pancreas, liver, or intestine. For example, in some embodiments, the biological material to be transplanted is or is derived from one or more kidney cells. In some embodiments, the subcutaneous anti-CD3 antibody formulation is administered during and/or after transplantation. In some embodiments, the subcutaneous anti-CD3 antibody formulation is administered during and/or after transplantation in combination with one or more additional agents. In some embodiments, the subcutaneous anti-CD3 antibody formulation and the additional agent(s) are administered simultaneously. For example, the subcutaneous anti-CD3 antibody formulation and the additional agent(s) can be formulated in a single composition or administered as two or more separate compositions. In some embodiments, the subcutaneous anti-CD3 antibody formulation and the additional agent(s) are administered sequentially.

Prophylactic Administration

The anti-CD3 antibody formulations (also referred to herein as antibody compositions) provided herein are used in diagnostic and prophylactic formulations. In one embodiment, an anti-CD3 antibody formulation provided herein is administered to patients that are at risk of developing one of the aforementioned autoimmune diseases. A patient's predisposition to one or more of the aforementioned autoimmune diseases can be determined using genotypic, serological or biochemical markers. For example, the presence of particular HLA subtypes and serological autoantibodies (against insulin, GAD65 and IA-2) are indicative of Type I diabetes.

In another embodiment provided herein, an anti-CD3 antibody formulation is administered to human individuals diagnosed with one or more of the aforementioned autoimmune diseases. Upon diagnosis, an anti-CD3 antibody is administered to mitigate or reverse the effects of autoimmunity. In one such example, a human individual diagnosed with Type I diabetes is administered with sufficient dose of an anti-CD3 antibody to restore pancreatic function and minimize damage of autoimmune infiltration into the pancreas. In another embodiment, a human individual diagnosed with rheumatoid arthritis is administered with an anti-CD3 antibody to reduce immune cell infiltration into and destruction of limb joints.

Preferably, the therapeutic, diagnostic and/or prophylactic anti-CD3 antibody formulations provided herein are administered to a subject intravenously or subcutaneously. Other routes of administration are contemplated. For example, the anti-CD3 antibody formulations are administered intravenously, subcutaneously, orally, parenterally, nasally, intramuscularly, or any combination of these routes of administration.

Other Aspects of the Invention

In another aspect, the disclosure provides methods of purifying an anti-CD3 antibody by affinity chromatography, ion-exchange chromatography, and/or hydroxyapatite chromatography. For example, the affinity chromatography is protein A chromatography. The ion exchange chromatography is, e.g., anion exchange chromatography.

In a further aspect the invention provides oral formulation of therapeutic antibodies know in the art. The formulation is a liquid or a lyophilized powder.

The lyophilized formulation includes a unit dose an antibody or antigen binding fragment thereof and about 34 mg trehalose and 0.17 mg methionine per mg of antibody or antigen binding fragment thereof.

The liquid formulation includes a unit dose of an antibody or antigen binding fragment thereof, 20% trehalose (w/v), and 0.1% methionine (w/v).

These oral formulation can be in the form of a capsule, preferably an enteric coat capsule.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. By "specifically bind" or "immunoreacts with" is meant that the antibody reacts with one or more antigenic determinants of the desired antigen and does not react (i.e., bind) with other polypeptides or binds at much lower affinity ($K_d$>10') with other polypeptides.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ea., 2nd ed. Raven Press, N.Y.

(1989)). The variable regions of each light/heavy chain pair form the antibody binding site.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

As used herein, the term "epitope" includes any protein determinant capable of specific binding to an immunoglobulin, a scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is ≤1 μM; preferably ≤100 nM and most preferably ≤10 nM.

As used herein, the terms "immunological binding" and "immunological binding properties" and "specific binding" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides are quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to a CD3 epitope when the equilibrium binding constant ($K_d$) is ≤1 μM, preferably ≤100 nM, more preferably ≤10 nM, and most preferably ≤100 pM to about 1 pM, as measured by assays such as radioligand binding assays or similar assays known to those skilled in the art.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family.

The term "agent" is used herein to denote a chemical compound, a mixture of chemical compounds, a biological macromolecule, or an extract made from biological materials.

The term patient includes human and veterinary subjects.

The disclosure also includes $F_v$, $F_{ab}$, $F_{ab'}$ and $F_{(ab')2}$ anti-CD3 antibody fragments, single chain anti-CD3 antibodies, bispecific anti-CD3 antibodies, heteroconjugate anti-CD3 antibodies, trispecific antibodies, immunoconjugates and fragments thereof.

Bispecific antibodies are antibodies that have binding specificities for at least two different antigens. In the present case, one of the binding specificities is for CD3. The second binding target is any other antigen, and advantageously is a cell-surface protein or receptor or receptor subunit.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The disclosure having now been described by way of written description, those of skill in the art will recognize that the disclosure can be practiced in a variety of embodiments and that the foregoing description and examples below are for purposes of illustration and not limitation of the claims that follow.

Example 1: Dosing

Animal model data indicated that a suitable dose for an oral anti-CD3 formulation of the disclosure is about 15 mcg/mouse 20 g body weight or approximately 750 mcg/kg for each mouse. The conversion factor for the human equivalent dose based on body surface area is 12.3. Thus, the human equivalent dose comes to 3.67 mg/60 kg body weight. Human subjects will receive between 0.1 mg to 10 mg of anti-CD3 antibody.

Animal data has demonstrated that the subcutaneous dose needs to be at least two-fold higher than the dose for the oral anti-CD3 formulation. Thus, the dose range for the subcutaneous anti-CD3 formulations of the disclosure are in the range of about 1 mg/60 kg body weight to 60 kg body weight.

Example 2: General Methods for the Production of a Lyophilized NI-0401/CD3 Antibody Dosage Form for Use in Oral Formulation The goal of these studies was to develop oral dosage formulations of NI0401. Specifically, the goal of this study was to produce a lyophilized dosage form of NI-0401/CD3 antibody. The lyophilized form of NI0401 will be the active ingredient of an oral formulation in a capsule.

A lyophilizable formulation was developed through excipient screening for bulking agents and stabilizers, followed by stability assessment at T0&T14. Briefly, feasibility assessment was done as summarized
  Iteration 1: Screening with bulking agents and stability analysis at T0&T14: Bulking agents such as Trehalose, Sucrose, Mannitol and Lactose were used.
  Iteration 2: Screening with stabilizers and stability analysis: stabilizers such as Methionine, Arginine, Sodium Ascorbate and EDTA were used combination with selected bulking agent, Trehalose from iteration #1.
    Determination of glass transition temperature (Tg) using MDSC on selected lead formulation from iteration #2 (containing Trehalose as bulking agent, and stabilizers Methionine+/−EDTA).
  Iteration 3: Lyophilization of lead formulations, and 14-day short-term stability analysis at T0&T14 (50° C.&4° C.).
Materials and Methods
Dialysis Dialysis promotes the exchange of aqueous buffer with the protein of interest via selective diffusion through a semi-permeable membrane with a known molecular weight cut off. Membranes used for this technique differ on pore size.

A sample aliquot NI-0401 in 25 mM sodium acetate/125 mM NaCl/0.02% W/V Polysorbate was taken in a Slide-A-Lyzer® Dialysis Cassette (3-12 mL with MW cut off 10,000). Then the sample was dialyzed against 0.5 liter of the buffer containing 25 mM sodium acetate/0.02% W/V Polysorbate without sodium chloride, pre-equilibrated to 2-8° C. with first 3 buffer exchanges (in an interval of ~1 hrs) with 500 mL of buffer, for the removal of sodium chloride from sample. The dialyzed samples were collected from the cassette and the concentration of NI-0401 sample was assessed without dilution by UV spectroscopy using a Nano Drop spectrophotometer based on the theoretical extinction of 1 mg/mL is 1.52 at A280 nm provided by Tiziana.

pH

The pH of NI-0401 formulation sample or placebo was measured using a Thermo Scientific, Orion Star Model A 211 pH meter equipped with a Ross PerpHecT micro electrode, Model 8220BNWP. For buffer solution preparation, a triode electrode was used to measure the pH (Thermo Scientific, US Gel-filled Ultra Triode Electrodes). The instruments were standardized using pH 4, 7 and 10 buffers before each use.

A280

For A280 method verification, was assessed by UV spectroscopy using the SpectraMax Plus 384 system by Molecular Dynamics, equipped with SoftMAX Pro 6.4. Standard quartz cuvettes (Starna Cells) with the path length set to 1 cm was used for A280 analysis. All wells of the 96-well quartz plate were filled with 200 µl of water and read at 280 nm, 252 and 330 using standard water check. A 1×PBS buffer was used for all dilutions and as blank buffer. The NI-0401 stock solution of 5.9 mg/mL was diluted to 1.2 mg/mL using 1×PBS into a 1.5 mL tube. This stock solution was used to make the following dilutions of 1.0, 0.8, 0.6, 0.4, 0.2, and 0.1 mg/mL. All dilutions were made in separate micro-centrifuge tubes and vortex mixed for couple of seconds. Each dilution was performed in 3 replicates except for 1.0 mg/mL, which was performed in 6 replicates. The target concentration for sample analysis was selected at 1 mg/mL. The dilution with six replicates was to obtain the intra- and inter-precision at 100% target concentration. The standard dilutions were transferred over to the 96-well quartz plate at 200 µl each. The plate with the dilutions were ran at wavelengths 280 nm, and 330 nm. The background at 330 nm was subtracted from A280 and then the values were analyzed for linearity, precision and accuracy.

SDS-PAGE

NI-0401 Purity/Stability was determined using sodium dodecyl sulfate-polyacrylamide gel electrophoresis (SDS-PAGE) under reducing and non-reducing conditions. Samples were analyzed on 4-12% Bis-Tris gels. Samples for reducing analysis were reduced in the presence of beta mercapto ethanol and separated on 4-12% Bis-Tris gels. The method was verified by running three gels with three different loads for establishing precision and linearity in estimation of protein purity. Linearity of each gel was determined by utilizing the GS800 densitometer Quantity One Software.

SEC-HPLC

A size-exclusion high performance liquid chromatography (SE-HPLC) method was verified for linearity, accuracy and precision over three consecutive days. Tiziana provided NI-0401 sample at ~6.5 mg/mL (6.0+/−0.6 mg/mL) that was used as a standard for the method verification.

MDSC

MDSC is used to determine and compare the glass transition (Tg) temperature of lead (liquid) formulations. MDSC measures the difference in heat flow between a sample and inert reference as both are subjected to a simultaneous linear and sinusoidal temperature program. Thermal behavior of the in-process samples was carried out with differential scanning calorimetry.

For the MDSC study, the un-dialyzed/dialyzed NI-0401 protein sample was aliquoted 2.5 mgs per vial. 30 µL of liquid formulations were loaded into T Zero pans and crimped with T Zero hermetic lids. Empty TZero pan crimped with TZero hermetic lid was used as reference. Samples were examined by placing 30 µL of the lead formulation into Tzero pans and hermetically sealed. Empty pans were used as the reference. Glass transition temperatures (Tg) and Eutectic temperature (Teu) were evaluated using the method parameters listed below.

MDSC method parameters used to determine Tg & Teu of NI0401

Modulate +/−1° C. every 60 sec
Isothermal for 5 min

Ramp 1° C./min to −60° C.
Mark the end of cycle 1
Isothermal for 5 min
Ramp 1° C./min to 25° C.
Mark the end of cycle 1
MDSC method parameters used to determine annealing effects on Tg of NI-0401
Equilibrate at 25° C.
Modulate +/−1° C. every 60 sec
Isothermal for 5 min
Ramp 1° C./min to −60° C.
Isothermal for 5 min
Ramp 1° C./min to −22/24/26° C.
Isothermal for 5 min
Ramp 1° C./min to −60° C.
Isothermal for 5 min
Ramp 1° C./min to 20° C.
Mark the end of cycle 1

Karl-Fischer

The moisture content was determined using a Mettler Toledo DL36 KF Coulometer with a Mettler Toledo DO305 Drying Oven. The instrument was calibrated with a Hydranal water standard for KF-Oven (Sigma, 34784, Lot # SZBD 226AV). The vials with lyophilized cake was heated at 100° C. in the drying oven and the water vapor generated was titrated coulometrically in Hydranal (Sigma, 34836, Lot # SZBE 2830V). The vial with the lyophilized cake was heated in the oven, the residual water vapor in the sample was bubbled into a vessel with a cathode and an anode solution, where the water triggered the oxidation of sulfur dioxide by iodine. The amount of iodine generated, and hence the amount of water was calculated from the quantity of electricity that flows during the reaction. Dividing the amount of water generated and the lyophilized cake weight in the sample, the percent water contents is calculated.

Osmolality

Osmolality measurements were made using a freezing-point micro Osmometer, equipped with a 20 μL Ease Eject™ Sampler). The units of measure are milliosmoles of the solute in 1 kg of pure solvent, expressed as Osmolality (mOsm/kg H20). The instrument was calibrated with 50 mOsm/kg (3MA005) and 850 mOsm/kg (3MA085) calibration standards and verified with a 290 mOsm/kg Clinitrol® control Reference Solution (3MA029) prior to analysis. Sample testing was conducted in accordance with SOP: DV-02-023. The osmolality of NI-0401 formulations were measured via depression in freezing point method.

Gel Isoelectric Focusing (IEF)

The pH of the NI0401 formulation is critical to its stability and bioactivity. The net charge on NI-0401 is zero at its isoelectric point (PI), positive at pH below PI and negative at pH above PI. The solubility is the lowest at PI. The choice of pH is made by not only solubility but also stability and binding property. Thus, a compromise pH for maximum solubility and stability should be chosen for formulation development.

NI-0401 samples were made in IEF sample buffer (pH 3-10) and samples were loaded without heat directly on to a IEF vertical slab gel (pH 3-10) along with pH gradient markers. The anode and cathode running buffers were prepared and gel conditions were run (as described in Life Technologies Novex Pre-Cast Gel Electrophoresis Manual # IM-1002). The gels were run at 100V for 1 hour, 200V for 1 hour, 500V for 30 min. After the gel run, the gel was fixed with 12% trichloroacetic acid (TCA) for 30 minutes and washed over 2 hours with DI water changes every 30 minutes to remove the 12% TCA. The gel was then stained with simply blue stain.

Capillary Isoelectric Focusing (cIEF)

A non-qualified Capillary Isoelectric Focusing cIEF method was used for confirmation purpose only. The (cIEF) was performed by Proteome PA-800 Protein Characterization System using a Neutral Capillary. pI markers 4.1, 5.5, 7.0, 9.5, and 10.0 were spiked into the sample for linear calibration of pI vs time. The sample for analysis was prepared by adding 10 μL of 6 mg/mL NI-0401 to 240 μL of a mixture containing, 200 μL of 3 M urea-cIEF Gel, 12.0 μL of Pharmalyte 3-10 carrier ampholytes, 20.0 μL of cathodic stabilizer, 2.0 μL of anodic stabilizer and 2.0 μL of each five pI markers. The contents were vortex mixed for 15 seconds, and centrifuged for 5 minutes at 10,000 rpm before analysis.

Lyophilization parameters: Iteration #1 &2

NI-0401 lyo formulations were prepared by spiking NI0401 protein sample with different bulking agents and stabilizers. After the addition of bulking agents and stabilizers, pH of the all formulations and buffers were measured, and adjusted the pH to ~5.5±0.05. For lyophilization of iteration 1&2 formulations, the vials aliquoted with 2.5 mg of formulations were placed in the middle of tray and lyophilized using the parameters shown in Table 1-2 in a FTS Lyo Star II Lyophilizer respectively. After completion of the lyophilization, the vials were back filled with Nitrogen at 600,000 mtorr and stoppard. The vials were retrieved from shelf after reaching the set pressure. The vials were promptly sealed with aluminum crimp-caps to prevent the atmospheric air contamination and to prevent the N2 releasing from the vial. All lyophilized vials were analyzed at T0 and the vials were incubated at 50° C. for analyses at T14 (except for iteration #1 which was for 12 days). Corresponding liquid formulations were also kept at 50° C. for 14 days (except for iteration #1 which was for 12 days).

Lyophilization Parameters: Iteration #3

NI-0401 lead lyo formulations were prepared by NI-0401 protein sample pH: 5.59 with 20% Trehalose as bulking agent and 0.1% Methionine+/−0.1% EDTA as stabilizers. Addition of 0.1% Methionine (from 0.3M/4.44% stock) did not alter the pH. However, addition of EDTA (from stock of 0.5M) changed the pH from 5.59 to 5.9, which was adjusted pH of ~5.5 with 1N HCl. The NI0401 sample was aliquoted at ~2.5 mg per vial. Placebo's for lead formulations were prepared without NI-0401 sample. For lyophilization of lead formulations, the vials with lead formulations are placed in the middle shelf along with vials (20) filled with ~400 ul of each placebo buffer. The rest of space on lyophilization shelves were filled with vials containing 1 ml of water per vial. One vial of each formulation and one vial of each placebo was used to check the temperature profiles by inserting temperature probe in the lyophilizer Example 3: Lyophilization Feasibility Assessment of NI-0401

The current NI-0401 formulation NI-0401 is ~6.0 mg/mL in buffer containing 25 mM sodium acetate pH 5.5, 125 mM sodium chloride and 0.02% (w/v) Polysorbate 80, the goal was to assess the lyophilization of antibody in the same formulation. Since, the presence of sodium chloride, a crystalline excipient is always a concern while lyophilizing a protein/antibody, because of its inherent nature of absorbing water over time unless it is annealed during the lyophilization step. Therefore, the excipient screening involved examination of current formulation (undilayzed formulation) as is with spiking in bulking agent and stabilizers, and also by dialyzing sodium chloride out of the formulation (dialyzed formulation) and then spiking in with bulking agent and stabilizers.

There were two sets of formulations, un-dialyzed/dialyzed NI-0401 formulations. For all iterations, 2.5 mg were lyophilized. For Dialyzed NI-0401 formulation, NI-0401 sample was dialyzed to remove the salt from the formulation buffer, which was done to remove the eutectic point during the primary dying process and to avoid the atmospheric moisture absorbance by the NI-0401 lyophilized formulation. The formulations were analyzed at T0 or T14.

The formulations for T zero stability (T0) were analyzed immediately after lyophilization.

The formulations for 14-day stability (T14) were incubated at 50° C.

At T0 &T14, the formulations were analyzed for the appearance of cake, reconstitution time, appearance of liquid sample, A280, pH, SDS-PAGE and SEC-HPLC.

The formulation with bulking agents/stabilizers showing the highest stability and lowest levels of impurities was identified for lead formulation based on the stability data.

Example 4: Iteration 1: Screening with Bulking Agents

List of Formulations

Lyophilization of NI-0401 formulations was evaluated in the current formulation buffer containing sodium acetate, pH 5.5 with and without sodium chloride, with a goal to understand the effect of crystalline salt on the stability of NI-0401 sample at T0 &T14. Therefore, NI-0401 was dialyzed against 25 mM sodium acetate buffer with 0.02% W/V Polysorbate with no sodium chloride.

The undialyzed/dialyzed NI-0401 formulations with different bulking agents (Table 4) at concentration of 2.5 mg/vial were lyophilized then evaluated at day zero (T0) and day 12 (T12) at 50° C. to understand the stability of formulation with time and temperature in reference to control formulation and the stability results at T0&T14 are summarized in Table 5-6.

Cake Appearance & Reconstitution Time

The lyophilized and liquid formulations were analyzed for stability at T0 and T12 (incubated at 50° C. for T12 days). After lyophilization, the cake appearance was amorphous for all formulations except for undialyzed/dialyzed control lyo formulations (Table 5). All lyo and liquid formulations were clear except for the lyo formulations containing mannitol and Lactose, which were cloudy (Table 5&6).

A280

The data indicated that the protein concentrations of iteration #1 formulations ranged from ~5.4 to 6.1 mg/mL with no significant difference in protein concentration at either T0 or after T12 except for the T12 formulation containing mannitol (Table 5&6) due to the opalescence of the formulation.

SEC-HPLC

SEC-HPLC analysis with all formulations showed no change in main peak RT (about 12.4+/−0.2) except for the undialyzed Lyo formulation containing Lactose which eluted with a shift in RT of 11.9 minutes SEC-HPLC analysis with un-dialyzed and dialyzed T0 Lyo and liquid formulations showed the main peak response was about 99% of total response suggesting no significant impact upon lyophilization of the formulations. Among T0&T12 lyophilized formulations, NI-0401 formulation containing Trehalose and lactose showed the highest purity (with recovery of >99% in main peak response respectively). However, the formulation containing lactose shifted the main peak retention time. A least recovery of total peak area at T12 is seen for the formulation containing mannitol (Table 5-6). The T0 and T12 formulations containing Trehalose showed less % impurity compared to other formulations including the control formulation (Table 5&6). All liquid formulations are prone for higher degradation at 50° C. and showing higher % of impurity at T12 time point compared to lyo formulations (Table 5&6).

SDS-PAGE

The SDS-PAGE gel analysis data for % purity of formulations is presented in Table 16. The undialyzed/dialyzed Lyo formulations containing Trehalose showed low levels of impurities with % purity of >98.6% & >97% respectively on non-reduced and reduced gel at T0&T12 compared to control formulations. The undialyzed/dialyzed Lyo NI0401 formulations containing Lactose showed shift in protein mobility on a non-reduced &reduced gel The dialyzed Lyo formulation at T12 showed more % purity compared to undialyzed lyo formulation on a reduced and non-reduced gel Undialyzed/dialyzed Lyo formulations containing Mannitol at T0& T12 showed very low recovery (80-87% recovery) showing higher % impurities on a non-reduced gel, which is consistent with SEC-HPLC data.

The quantitative analysis with SDS-PAGE analysis with liquid formulations using Tiziana SDS-APGE method showed higher degradation of liquid formulations at T12 compared to T0 liquid formulations on a non-reduced gel. Further liquid formulation containing Lactose showed shift in the mobility. The liquid formulation containing Trehalose showed higher % purity compared to other formulations.

Based on these results, the formulation containing 10% Trehalose with and without dialysis were selected for iteration #2 to screen in combination with different stabilizers.

SEC analysis showed high % purity and low % impurity for T0 and T12 formulations containing Trehalose compared to other formulations including the control formulation.

SEC analysis indicated that all liquid formulations are prone for high LMW degradation showing high % impurities when kept at 50 C for 12 days (T12) when compared to lyophilized formulations SEC analysis showed, among T12 lyophilized formulations containing Trehalose and lactose showed the highest purity. However, the formulation containing lactose shifted the main peak retention time.

With Non-reduced and Reduced gels analysis for undialyzed/dialyzed formulations, the formulations containing Trehalose and Lactose showed highest protein purity with low impurities. Formulations at T12 showed higher impurities compared to formulations at T0 consistent with SEC-HPLC data.

Lactose showed a shift in the mobility of protein on both reduced and non-reduced gel. Among the undialyzed/dialyzed formulations, formulations containing Mannitol showed low purity/recovery on gel analysis.

No significant difference in protein concentration of formulations was observed at either T0 or after T12 except for the formulation containing mannitol at T12. Lyophilized formulation containing Mannitol showed low solubility.

Example 4: Iteration 2: Screening with Different Stabilizers

Undialyzed or Dialyzed NI-0401 sample was lyophilized with stabilizers with a goal to understand the effect of stabilizers on stability of lyophilized NI-0401 formulation using the 10% Trehalose as bulking agent.

List of Formulations

For Iteration #2, the undialyzed/dialyzed NI-0401 formulations with different stabilizers using 10% Trehalose as bulking agent are summarized in Table 7. For the formulation study, the undialyzed/dialyzed samples were aliquoted at 2.5 mg/vial for liquid/lyophilization formulations. After lyophilization, the undialyzed/dialyzed liquid and lyo formulations were kept at 50° C. for 14 (T14) days or immediately analyzed at T0. The stability of the formulations was analyzed using A280, SDS-PAGE and SEC-HPLC and the results are presented below. Table 8 and 9 show the summary of stability analysis results with iteration #2 formulations.

Cake Appearance & Reconstitution Time

Table 8, show the appearance of the lyophilized cake at T0 and after 14 days of incubation at 50° C. which was amorphous for all formulations. The collapse of cake was higher in undialyzed formulations compared to dialyzed formulations (Table 8) and the collapse was almost 80-90% in undialyzed/dialyzed formulation containing Arginine. The dialyzed formulation containing sodium ascorbate also showed a collapse of 80-90% (Table 18).

The liquid appearance of the formulations was clear except for lyo &liquid formulation containing arginine, and the liquid formulation containing sodium ascorbate, which appeared cloudy due to precipitation (Table 8 & 9). The liquid formulation containing ascorbate became yellowish due to oxidation of ascorbic acid to dehydroascorbic acid.

A280

There was no significant change in the protein recovery among different lyo/liquid formulations except for the lyophilized un-dialyzed/dialyzed formulation with 10% Tre-Arginine (*) which showed variability in protein concentration due to precipitation/cloudiness of the formulation. The liquid and lyophilized un-dialyzed/dialyzed formulation containing 10% Tre-Sod.Ascorbate (*#) showed very high protein conc. due to the interference of ascorbate with A280 assay (Table 18-19).

SEC-HPLC

SEC-HPLC data with un-dialyzed and dialyzed T0&T14 lyo and liquid formulations showed main peak response was about 96-98% (Table 8-9), suggesting no significant impact upon lyophilization of the formulations except for formulation with Arginine. The main peak response for the formulation containing arginine was less than 97% ranging from 27% to 97% at T0 and 35-81% at T14 respectively due to the precipitation of the protein (Table 8-9). The slight reduction in the total response for formulations with EDTA is due to low protein concentration injected in to the column The liquid and lyo formulation containing arginine also showed highest % of impurities. The formulations containing methionine, Na. Ascorbate and EDTA showed least % total impurities (Table 8-9). Undialyzed/dialyzed formulations containing Trehalose or Trehalose-Methionine, showed no significant change in main peak RT. However, SEC-HPLC analysis with dialyzed NI-0401 formulations containing Arginine or EDTA at T0&T14 showed a shift in the retention time of 0.15-0.35 As expected the liquid formulations showed higher impurities compared to Lyo liquid formulations, and the recovery was about 96-99% (Table 8-9).

SDS-PAGE

The iteration #2 formulations were analyzed by SDS-PAGE under non-reducing and reducing conditions for determining the purity of formulations. The images and quantification analysis on all formulations with reduced and non-reduced gels are presented in Table 10. The undialyzed/dialyzed formulations containing methionine and EDTA showed high purity and low levels of impurities (Table 10) showing the purity of >99% on non-reduced gel and >95% on a reduced gel. Undialyzed/dialyzed liquid formulations containing arginine and Sodium Ascorbate at T14 showed very low recovery due to precipitation (Table 10), which is consistent with SEC-HPLC data.

The quantitative analysis with SDS-PAGE analysis with liquid formulations using Tiziana SDS-PAGE method showed higher degradation of liquid formulations at T14 compared to T0 liquid formulations on a non-reduced gel. Further liquid formulation containing Arginine showed higher impurities. The liquid formulation containing Trehalose with Methionine/EDTA showed higher % purity compared to other formulations.

SEC analysis showed high % purity and low % impurity for T0 and T14 undialyzed formulations containing 10% Trehalose with Met+/−EDTA compared to other formulations. T0& T14 formulations containing 10% Trehalose with Arginine showed the highest impurity and lowest recovery.

SEC analysis indicated that all liquid formulations are prone for high LMW degradation showing high % impurities when kept at 50° C. for 14 days (T14) when compared to lyo formulations.

SEC-HPLC analysis with dialyzed NI-0401 formulations containing Arginine or EDTA at T0&T14 showed a shift in the retention time of 0.15-0.35.

With non-reduced and reduced gels analysis on undialyzed/dialyzed formulations, the formulations containing 10% Trehalose with Met+/−EDTA/sod. Ascorbate showed highest protein purity with low impurities. All liquid formulations showed high impurities compared to lyo formulations. Among the undialyzed/dialyzed formulations, formulations containing Arginine and Sod. Ascorbate showed low purity/recovery.

No significant difference in protein concentration of formulations was observed at either T0 or after T12 except for the formulation containing Arginine at T0&T12 and formulation containing sod. Ascorbate at T14. The formulation containing sod. Ascorbate appeared yellow at T14.

Based on the stability data from Iteration #2 screening, the undilyzed formulation containing 10% Trehalose and 0.1% Met with and without EDTA were selected for iteration #2 to analyze for Tg using MDSC analysis.

Example 5: MDSC Analysis on Lead Formulations from Iteration #2 Screening

Based on the stability analysis with iteration #2 formulations at T0&T14, the lead formulation for undialyzed NI-0401 selected was 10% Trehalose with 0.1% methionine+/−EDTA. Modulated DSC on lead formulations was done to determine the glass transition temperature of the formulation in order to set the primary drying temperature of the formulations below the glass transition temperature (Tg) during lyophilization process.

List of Formulations

For the MDSC study, un-dialyzed and dialyzed NI-0401 liquid and lyophilization formulations were prepared with different stabilizers using 10% or 20% Trehalose as bulking agent and the sample was aliquoted at 2.5 mg per vial. Formulations used for MDSC study are summarized in Table 11 and MDSC analysis was performed using parameters in 30 μL of liquid formulations were loaded into T Zero pans and crimped with T Zero hermetic lids. Empty T Zero pan crimped with T Zero hermetic lid was used as reference.

Determination of Tg on Lead Formulations

MDSC was performed on undialyzed/dialyzed lead formulations and the current formulation to determine the thermal events including the glass transition temperature (Tg). The MDSC analysis results are summarized in Table 12 As shown in Table 12, MDSC on current formulation showed eutectic point which was completely removed by the presence of 10% Trehalose that is present in the lead formulation (undialyzed/dialyzed) along with 0.1% Methionine. However, presence of sodium chloride in the undialyzed formulation, reduced the glass transition temperature from −32° C. to −37° C. The Tg of un-dialyzed & dialyzed formulation with 0.1% Met was found to be −36.88° C. and −31.87° C. respectively.

Determination of Tg at Different Annealing Temperatures

Next, MDSC was performed at different annealing temperatures for the undialyzed lead formulation. As the transition temperature is −37° C. for the lead formulation, an attempt was made to reduce the glass transition temperature as it is difficult to maintain the product temperature at or below the collapse temperature of −37° C. during primary drying process step of lyophilization with a control of temperature and pressure. And if the shelf temperature is at below −37° C., the total lyophilization time will be longer and is not cost effective. As shown in Table 12, MDSC on lead formulation (undialyzed formulation with 10% Trehalose and 0.1% methionine) at different annealing temperatures showed no major change in the glass transition temperature (Tg of −37° C.) of undialyzed lead formulation.

Determination of Tg on Lead Formulations with 10%&20% Trehalose

The Annealing process at different temperatures did not reduce the glass transition temperature, therefore the formulation containing higher amount of Trehalose was evaluated to reduce the Tg. Furthermore, MDSC analysis indicated no significant difference between the formulation containing 20% Trehalose and 0.1% EDTA and the lead formulation containing 10% Trehalose and 0.1% methionine. In addition, there was no change observed in retention time in chromatogram (SEC-HPLC) among undialyzed NI0401 samples with 10% Trehalose-none/10% Trehalose-0.1% Methionine/20% Trehalose+0.1% EDTA. As shown in Table 12, MDSC on lead formulation (undialyzed formulation containing 0.1% methionine) with increase in Trehalose (from 10% to 20%) decreased Tg by ~2(° C.) which is desirable for lyophilization process, hence this formulation containing 20% Trehalose with 0.1% methionine+1-0.1% EDTA was selected for final iteration instead of formulation with 10% Trehalose.

Addition of 10% Trehalose as bulking agent removed the eutectic point caused by the presence of NaCl in the undialyzed lead formulation containing 0.1% methionine.

Change in the annealing temperature did not show effect on Tg of the lead formulation.

Increase in the concentration of Trehalose from 10% to 20% decreased the Tg of the lead formulation containing 0.1% Methionine from −36° C. to −34° C. which is desirable for lyophilization process. Addition of EDTA to lead formulation with 20% Trehalose did not have effect on Tg.

MDSC analysis on formulations containing 20% Trehalose and 0.1% Met with and without EDTA showed a Tg of ~−34.6° C. which is desirable for lyophilization process.

Formulations containing 20% Trehalose and 0.1% Met with and without EDTA selected as lead formulations for iteration #3. (Table 13)

Example 6: Iteration #3 Lyophilization & Stability Analysis of Lead Formulations Based on the stability analysis and MDSC results from iteration #2, undialyzed NI-0401 formulation containing 20% Trehalose 0.1% methionine was selected for the final lyophilization cycle and short-term stability assessment at T0 and T14. The analysis included residual moisture content by Karl Fisher, Appearance, Reconstitution time, A280, purity by SEC-HPLC and SDS-Page, Osmolality, % moisture content, gel IEF and cIEF. The results of the final iteration #3 are presented below and summary of stability analysis data is showed in Table 14.

Cake Appearance and Reconstitution Time

All iteration #3 lead formulations showed intact cake except for the control formulation which showed relatively more collapse. All formulations were dissolved in less than 1 minute and all formulations were clear except for control formulation at 50° C. which was slightly cloudy (centrifuged and used in the further stability analysis).

pH pH of different lyo formulations after reconstitution and before lyo are shown in Table 14. The data indicated that the pH value changed from 5.5 to 5.9 for the lead formulations containing Trehalose and 5.5 to 7.6 for the current formulation without Trehalose. The reason for a change in pH after lyophilization could be due to evaporation of acetic acid in the current formulation during lyophilization process which is more pronounced for the current formulation. Presence of bulking agent and stabilizers could have helped stabilize the pH in lead formulations.

A280

The protein concentrations of different formulations are shown in Table 14. Protein concentration (mg/mL) of different formulations were measured, without dilution using a Nano Drop spectrophotometer, based on the theoretical extinction of 1 mg/mL is 1.52 at A280 nm provided by Tiziana. The slight decrease in protein concentration after adding 20% Trehalose, is due to increase in volume after addition of 20% Trehalose. The data indicated no significant changes in protein concentrations, after incubation of the formulations at 4° or 50° C. for 14 days except for the current formulation at 50° C. due to slight precipitation.

Moisture Content (%)

The moisture content of different lead formulations along with current formulation was determined using a Mettler Toledo DL36 KF Coulometer and the results are shown in Table 14. The moisture content of the lead formulations containing Met/Met+EDTA was 3.34% and 2.32% respectively. There was no significant change in moisture content after incubating the formulations for 14 days at both 4° C. and 50° C.

Osmolality

Osmolality of different lyo formulations after reconstitution is shown in Table 14. The data indicated that the lead formulation containing Trehalose is hypertonic and the current formulation is isotonic as expected. There were no changes in osmolality after incubating the formulations for 14 days at 4° C. and 50° C.

SEC-HPLC

Figure 5:
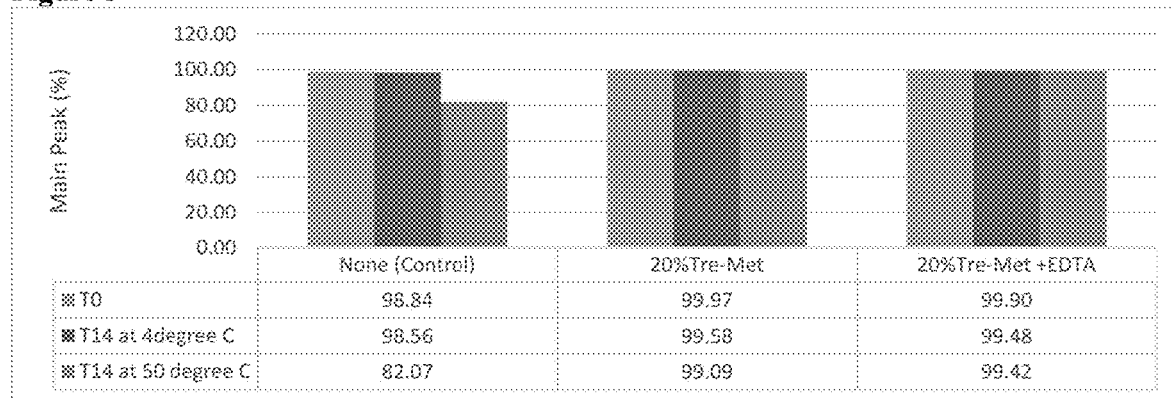
FIG. 5 is a bar chart showing the effect of time and temperature on lyophilized lead NI-0401 formulations: SEC-HPLC: % Main peak: T14 kept at 50° C. and 4° C. at 50° C.

NI-0401 formulations % main peak response, total area response (AUC) along with % impurity was assessed using SEC-HPLC analysis and the results are presented in FIG. 5-9 and Table 14). The main area response (AUC and %) for all formulations with NI-0401 is presented in FIG. 5. The overall data with T0& T14 lyo lead formulations, the main peak response was about 99.90% of total peak response (FIG. 5), suggesting no significant impact upon lyophilization of the lead formulations. However, the control formulations kept at 50° C./4° C. showed lower main peak response 82% and 98% respectively (FIG. 5). The reduction in % main peak recovery of control formulation at T14 (50°

C.) is due to the slight cloudiness/precipitation of the sample. The peaks observed between Retention times of 15-17 min are due to the components present in buffer/formulations such salt/methionine/EDTA Chromatograms for all formulations at T14 showed no significant change in main peak RT kept either at 50° C. and 4° C.

Figure 6:
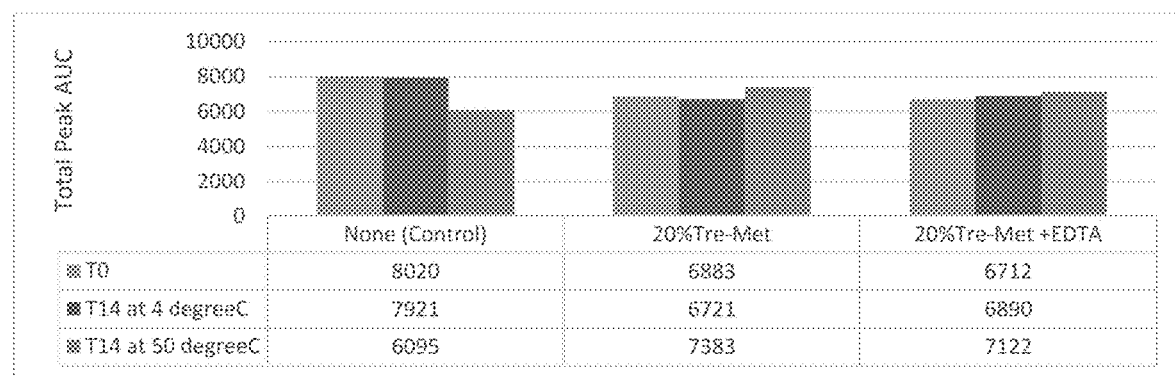
FIG. 6 is a bar chart showing the effect of time and temperature on NI-0401 lead lyophilized formulations: SEC-HPLC: Total peak AUC: T14 kept at 50° C. and 4° C.
Figure 7:
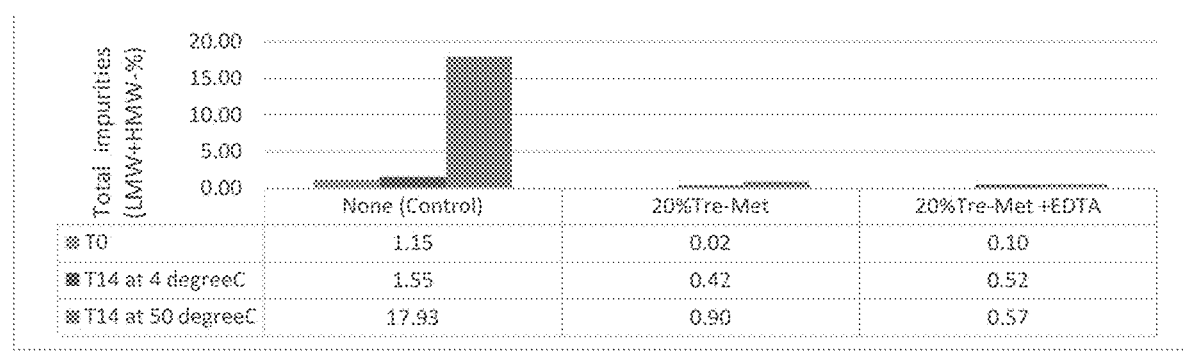
FIG. 7 is a bar chart showing the effect of time and temperature on NI-0401 lyophilized formulations: SEC-HPLC: % Total impurity: T14 kept at 50° C. and 4° C.
Figure 8:
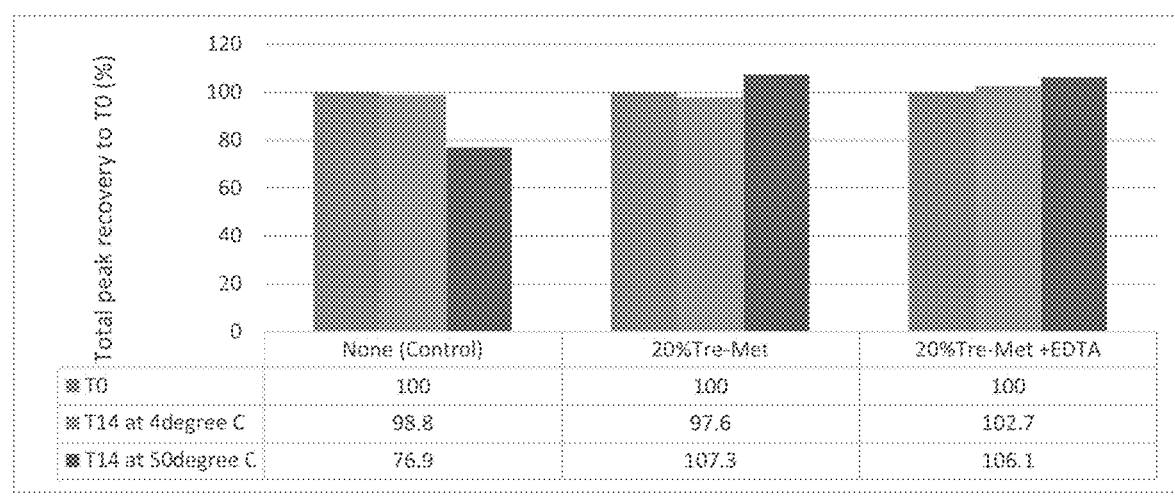
FIG. 8 is a bar chart showing the effect of time and temperature on NI-0401 lyophilized formulations: SEC-HPLC: % T14 Total peak recovery to T0.
Figure 9:
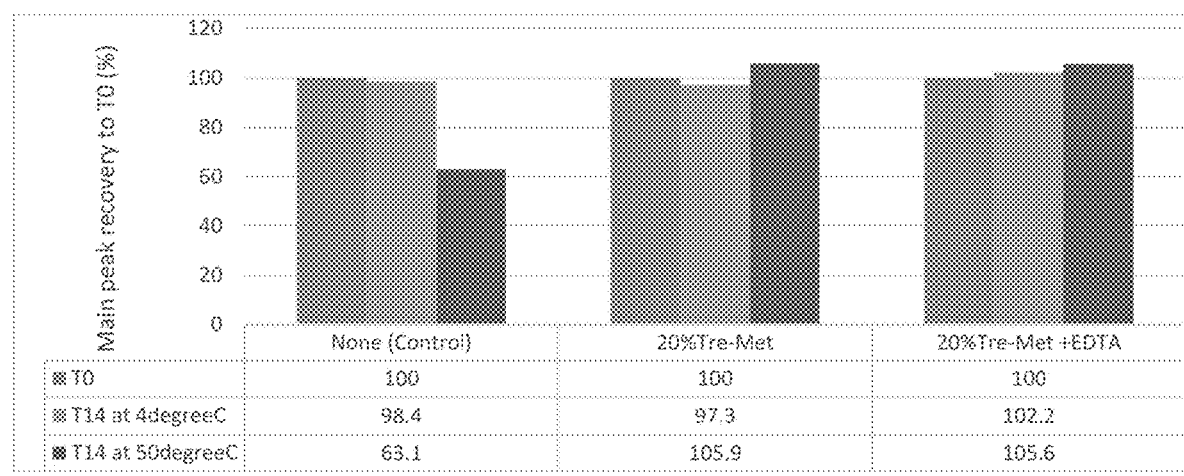
FIG. 9 is a bar chart showing the effect of time and temperature on NI-0401 lyophilized formulations: SEC-HPLC: % T14 main peak recovery to T0.

Spiking of formulations with Trehalose resulted in slight reduction in the concentration, therefore, lower response in the main peak response and total response for formulations with Trehalose and Met/Met+EDTA at either T0/T14 (4° C.) (FIG. 6). The formulations containing methionine/Met+EDTA showed least % total impurities (FIG. 7) compared to control formulation. T14 control formulation at 50° C. showed highest levels of impurities compared to T14 control formulation kept at 4° C. (FIG. 7). The % total peak recovery or % main peak recovery of T14 formulations compared to T0 formulations is not affected (FIGS. 8-9).

SDS-PAGE

Figure 10:
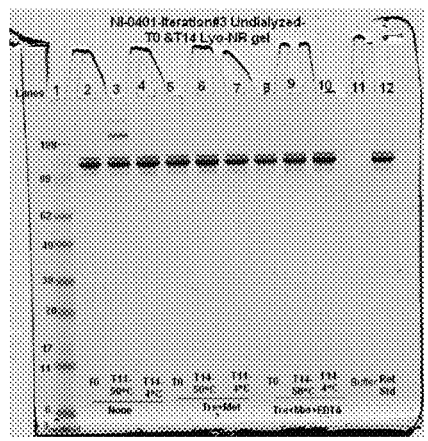
FIG. 10 is a photograph of a SDS gel showing the effect of Time and temperature on the stability of lead lyophilized formulations at T0&T14: Non-reduced SDS-PAGE.
Figure 11:
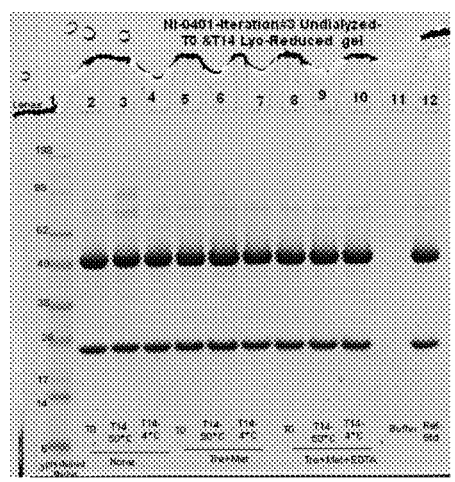
FIG. 11 is a photograph of a SDS gel showing the effect Time and temperature on the stability of lead lyophilized formulations at T0&T14: reduced SDS-PAGE.

The T0& T14 lead Lyo formulations containing Trehalose and Methionine/Trehalose, Methionine & EDTA kept either at 50° C./4° C. showed higher purity compared to control formulation (Table 15-16; FIG. 10-11) on a non-reduced and reduced gel with a percent purity of more than 99.3% and 98.5% respectively. T14 control formulation at 50° C. showed highest levels of impurities compared to T14 control formulation kept at 4° C. (Table 15-16; FIG. 10-11). There were no significant changes observed in the % purity of lead formulations on reduced and non-reduced gel at T0&T14 (Table 15-16; FIG. 10-11).

IEF Gel Analysis

Figure 12:
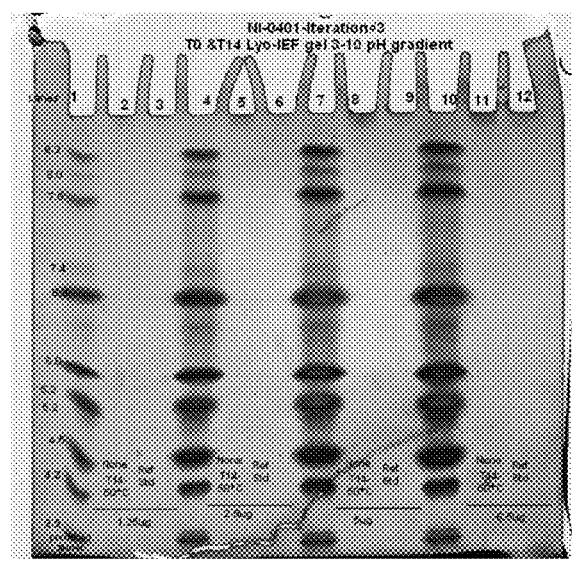
FIG. 12 is a photograph of a IEF gel showing the effect of Time and temperature on the stability of lead lyophilized formulations at T0&T14: gel IEF *Lanes 1,4,8, and 10 are pI markers with 5,10,15 and 20 ul of loading.

A test for IEF gels analysis on NI-0401 sample was performed to know the pI of the sample qualitatively using an unverified method. As shown in FIG. 12, different concentrations of control formulations T14 lyo (50° C.) and NI-0401 ref standard were loaded and analyzed on to IEF gel. The focusing of sample near the well is observed which is due to the high pI of sample that shows the approximate pI of the sample as >9.0 as the pI markers above 9.5 did not resolve on gel completely.

Since, IEF gel analysis with control formulation and NI0401 reference standard shows that pI of the NI0401 sample is too high (pI>9) to separate on IEF gel as the sample is retained near the well, further analysis for gel IEF on other lead formulations was not pursued. In summary, IEF gel analysis with control NI-0401 formulation shows that pI of NI0401 sample is around ~9.25.

cIEF Analysis

Figure 13:
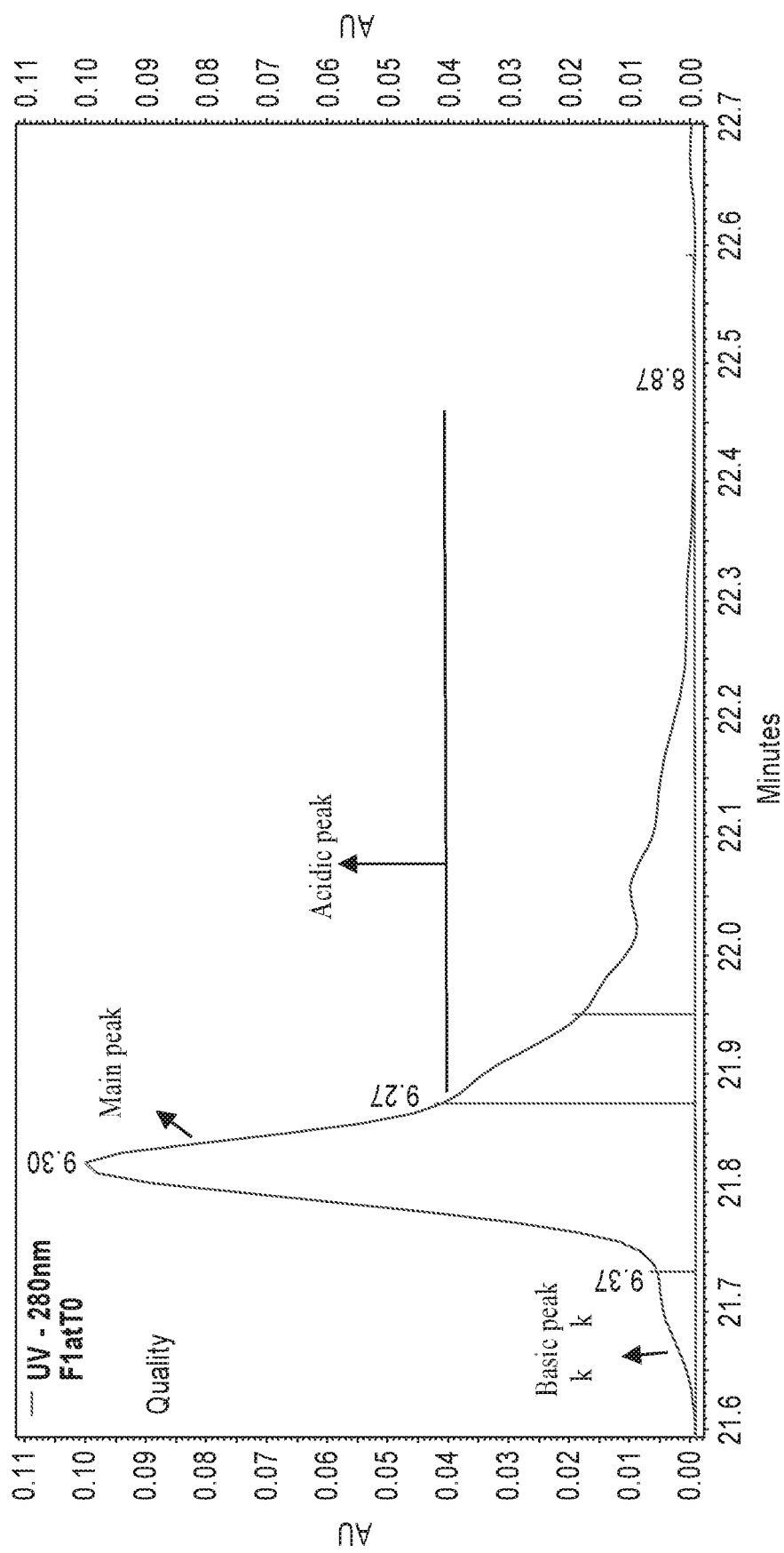
FIG. 13 is a plot showing the typical cIEF profile of current NI-0401 formulation at T0-Lyo and analysis.
Figure 14:
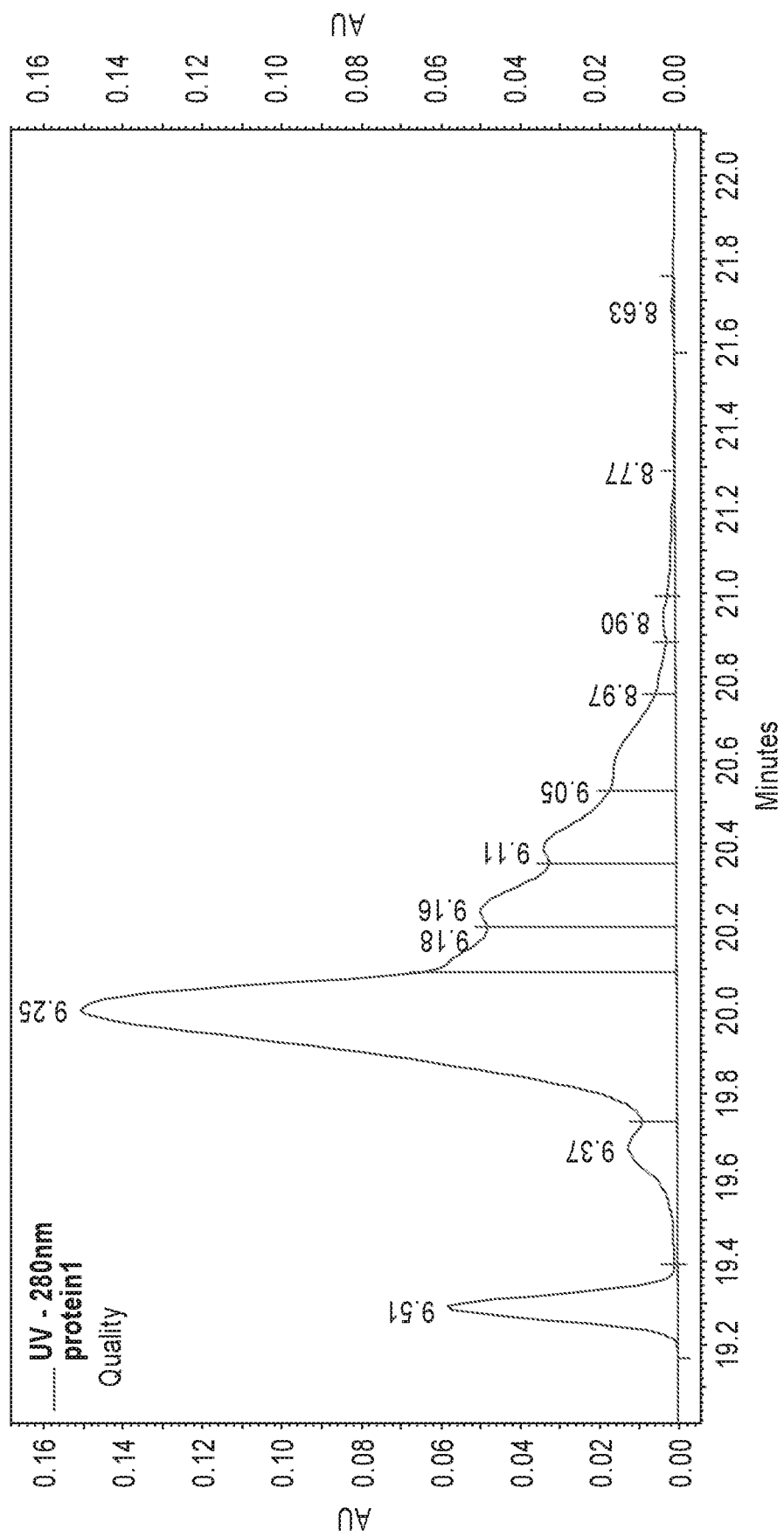
FIG. 14 is a plot showing capillary isolectric focusing (cIEF) analysis of NI-0401 following lyophilization. cIEF was conducted using 30 KV voltage for 15 min in Step 1 and 30 KV voltage for 30 min in Step 2. The pI value of NI-0401 is ~9.25 (basic).
Figure 15:
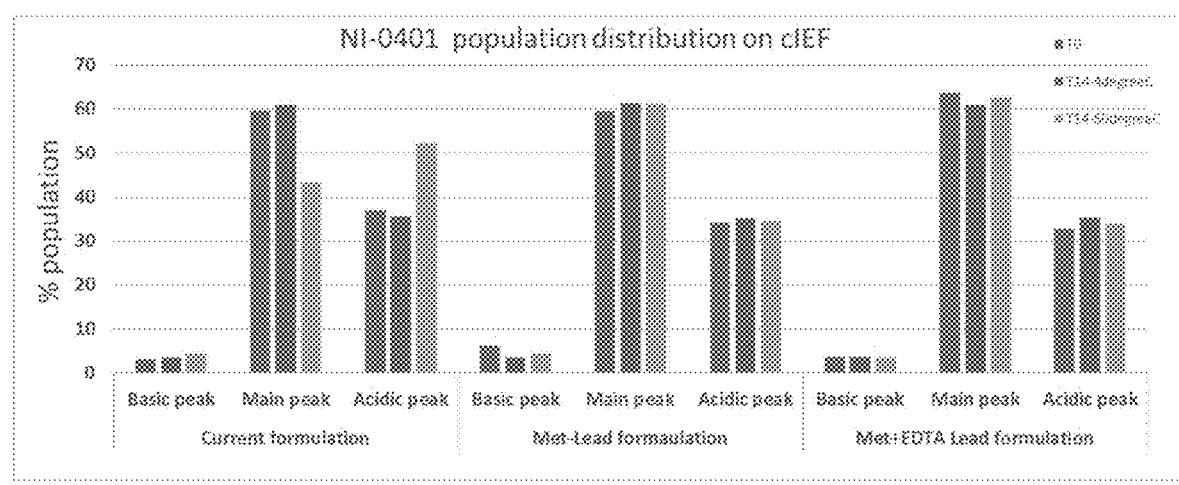
FIG. 15 is a bar chart showing the distribution of NI-0401 heterogenous population in lead formulation vs current formulation at T0&T14.
Figure 16:
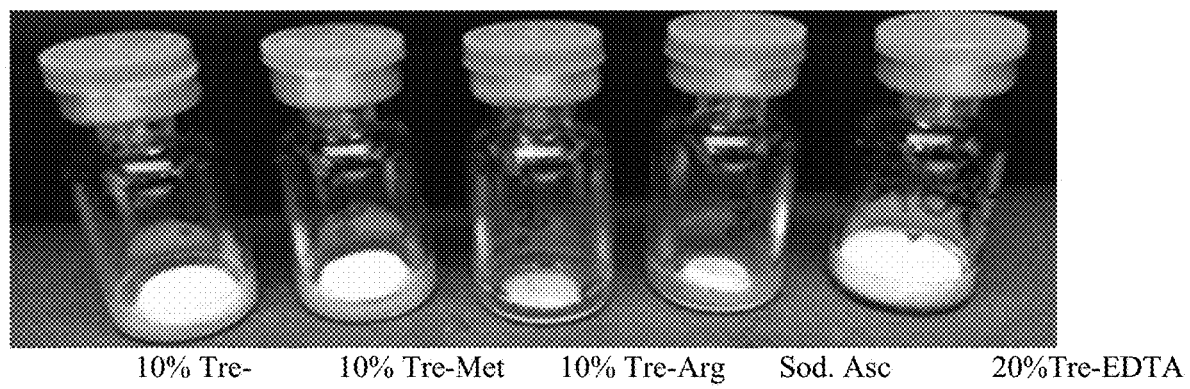
FIG. 16 is a photograph showing the stability and purity of the foralumab as determined by SEC-HPLC analysis correlated with appearance and integrity of the cake. Formulations with arginine and ascorbate showed the highest amount of collapse and loss of material FIG. 17, panels A and B, is a photograph showing cake appearance of lyophilized lead formulations at T14 (14 days after lyophilization) at 4° C. (panel A) and 50° C. (panel B). (1) Control formulation, buffer only, (2) 20% trehalose+0.1% methionine and (3) 20% trehalose+0.1% methionine+0.1% EDTA. NI-0401 showed intact cake in the formulations containing trehalose and methionine. More collapse seen in the control formulation.
Figure 17:
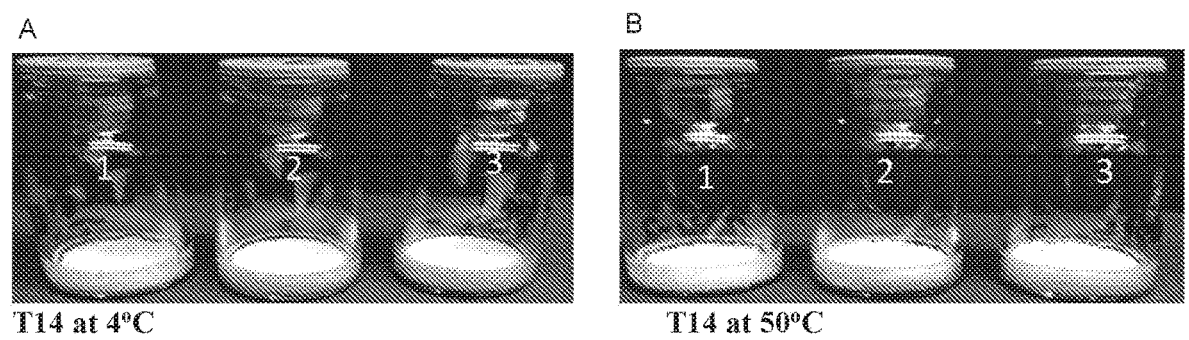
Figure 18:
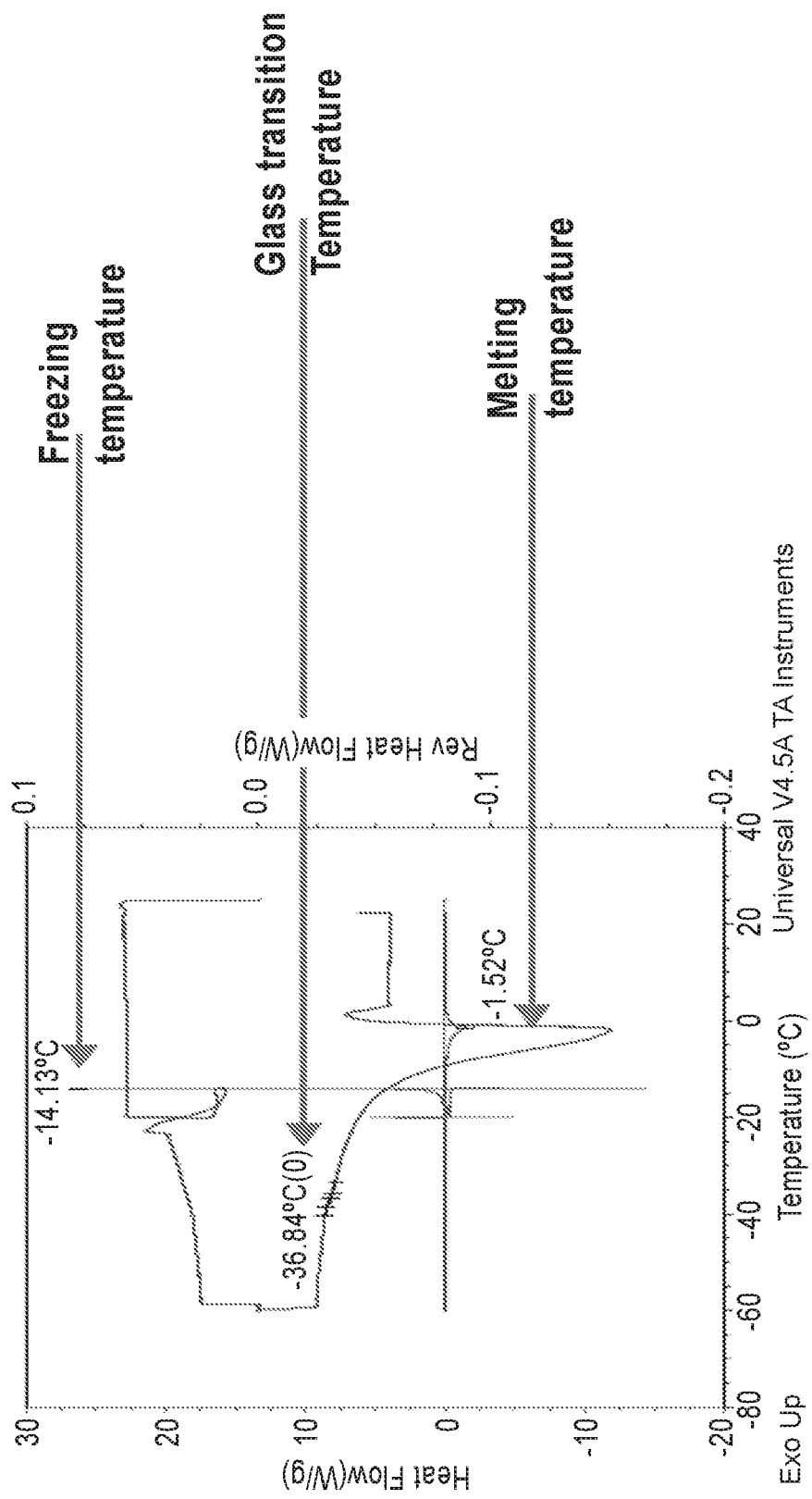
FIG. 18 is a plot showing MDSC (Modulated differential Scanning calorimetry) determination of freezing, melting and glass transition temperatures.
Figure 19:
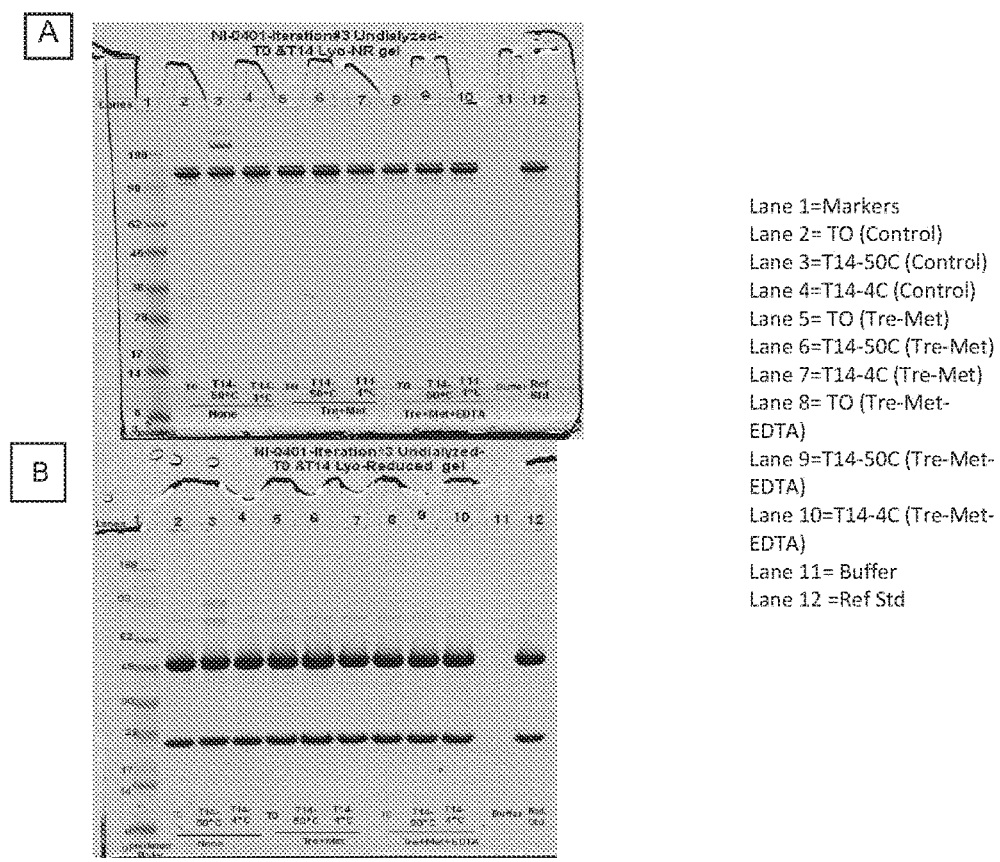
FIGS. 19 A and B: SDS-PAGE analysis of NI-0401 in lyophilized formulations at non-reduced (A) and reduced (B) conditions. No changes were observed in the purity of the NI-0401 antibody following the lyophilization cycle at ambient (T0) or after storage for 14 days (T14) at 4° C. or 50° C. Purity of the antibody was greater than 98% but in the control buffer at T14 and 50° C., the purity dropped to 85% under non-reducing conditions.
Figure 20:
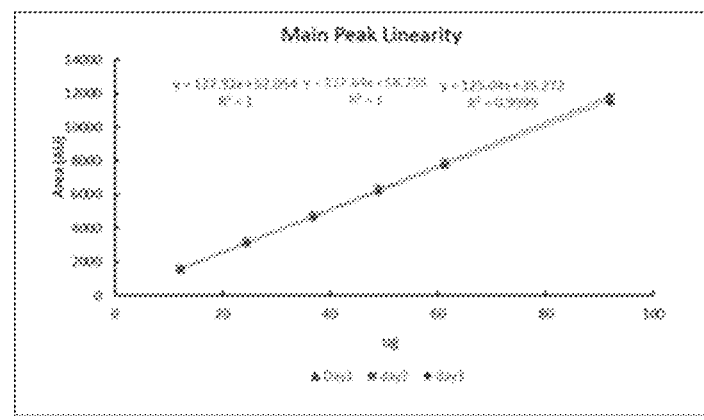
FIG. 20 is a line graph showing analysis of linear concentrations of forlaumab by SEC-HPLC to determine purity of the antibody.
Figure 21:
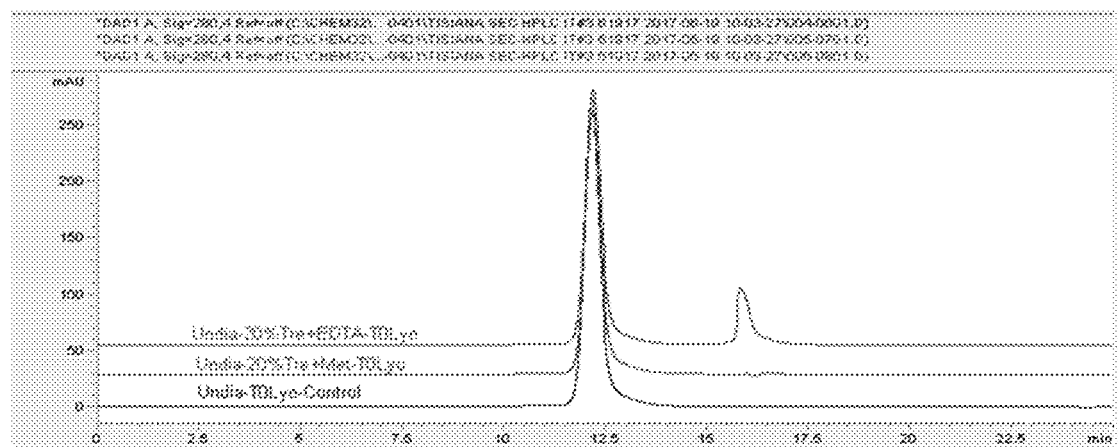
FIG. 21 A-C are a series of plots showing SEC-HPLC Analysis of the Lyophilized Foralumab Formulations at T0 (A), T14 at 4° C. (B) and T14 at 40° C. (C). Lead formulations showed excellent stability without impurity as compared to control formulation FIG. 22 A-C are plots showing representative SEC-HPLC Chromatogram at 36.78 µg or 6 ul Injection used to detect impurities. Full Scale (A). Expanded Scale (B). Overlay (C)
Figure 21:
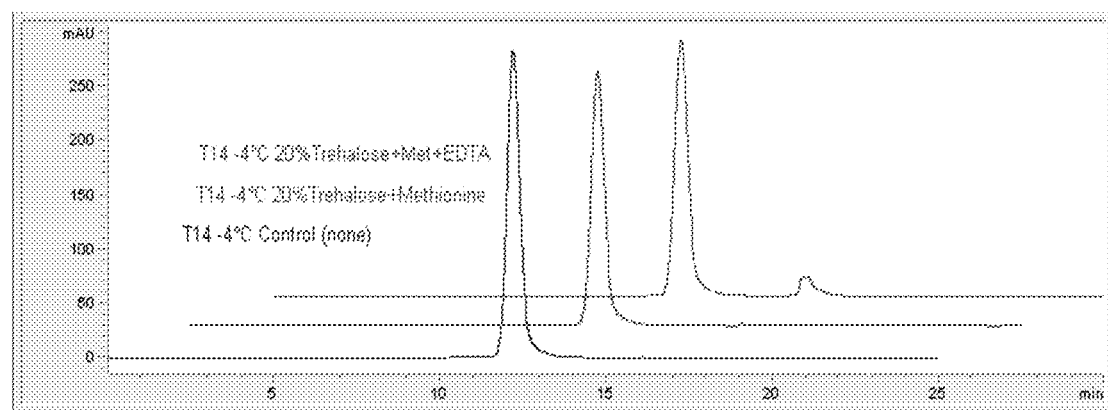
Figure 21:
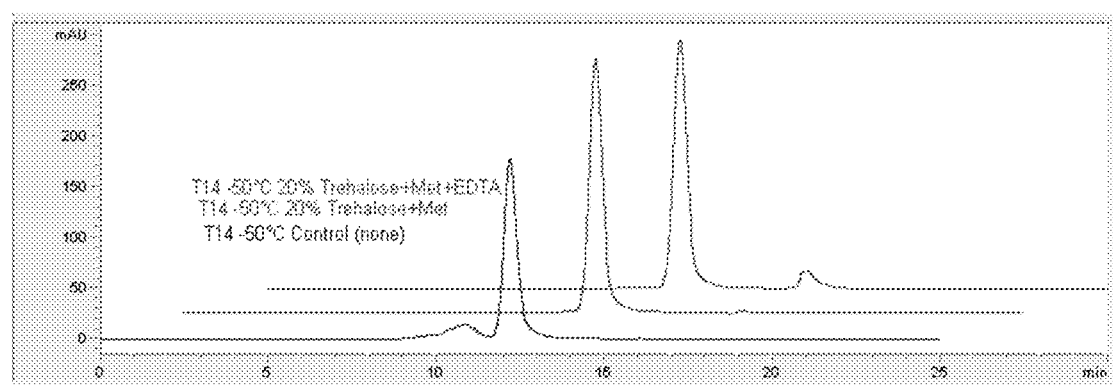
Figure 22:
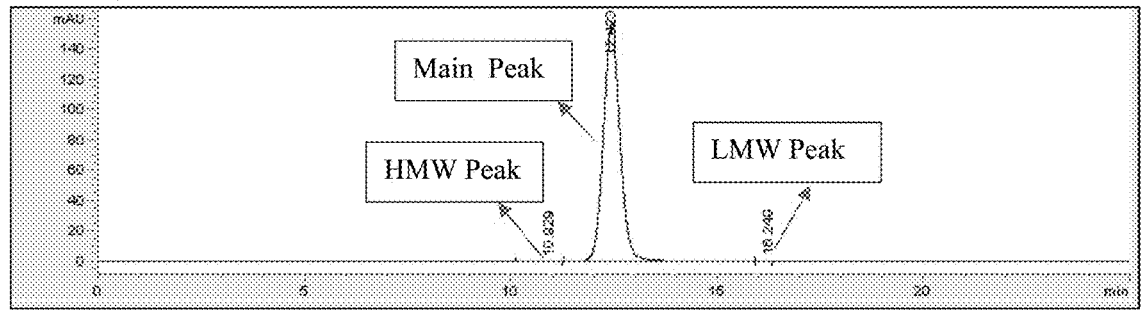
Figure 22:
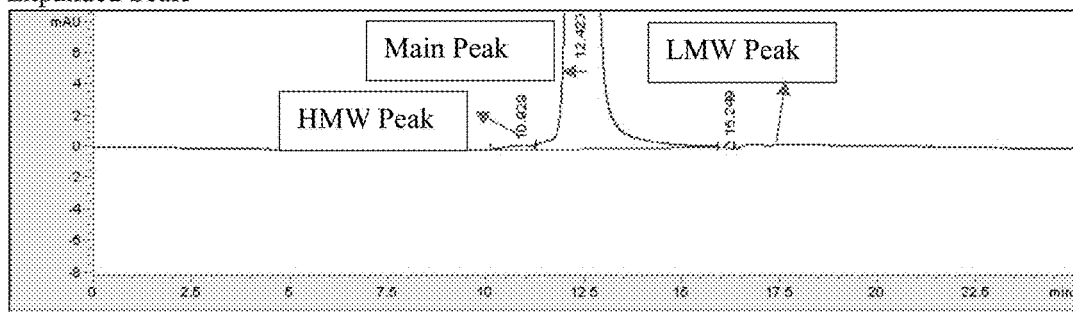
Figure 22:
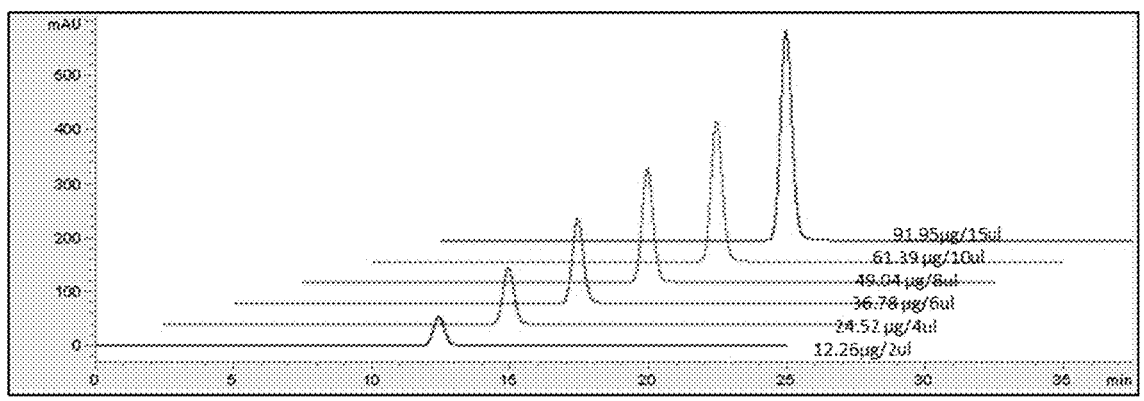
Figure 23:
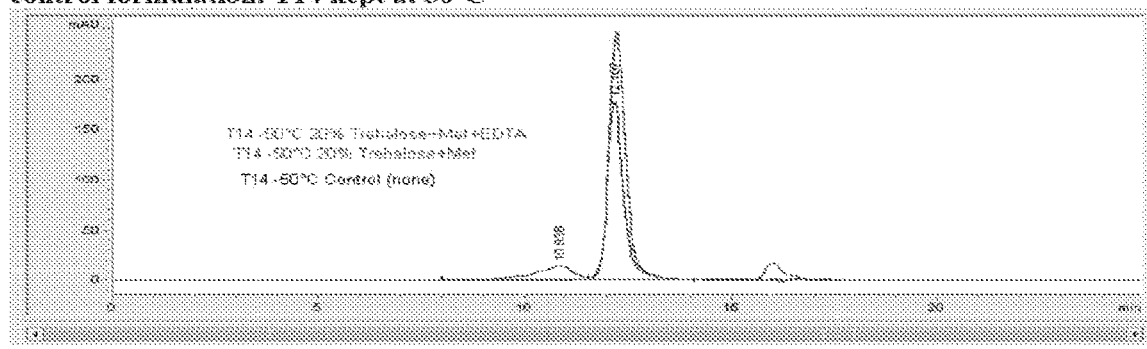
FIGS. 23 A and B are chromatographs showing lyophilized material is stable at 50° C. for 14 days. Full Scale (A). Enlarged (B).
Figure 23:
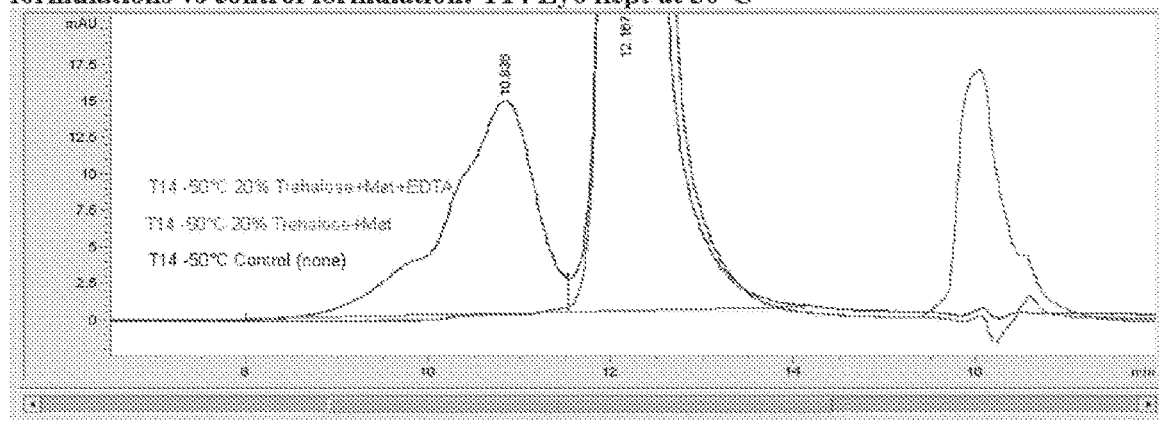
Figure 24:
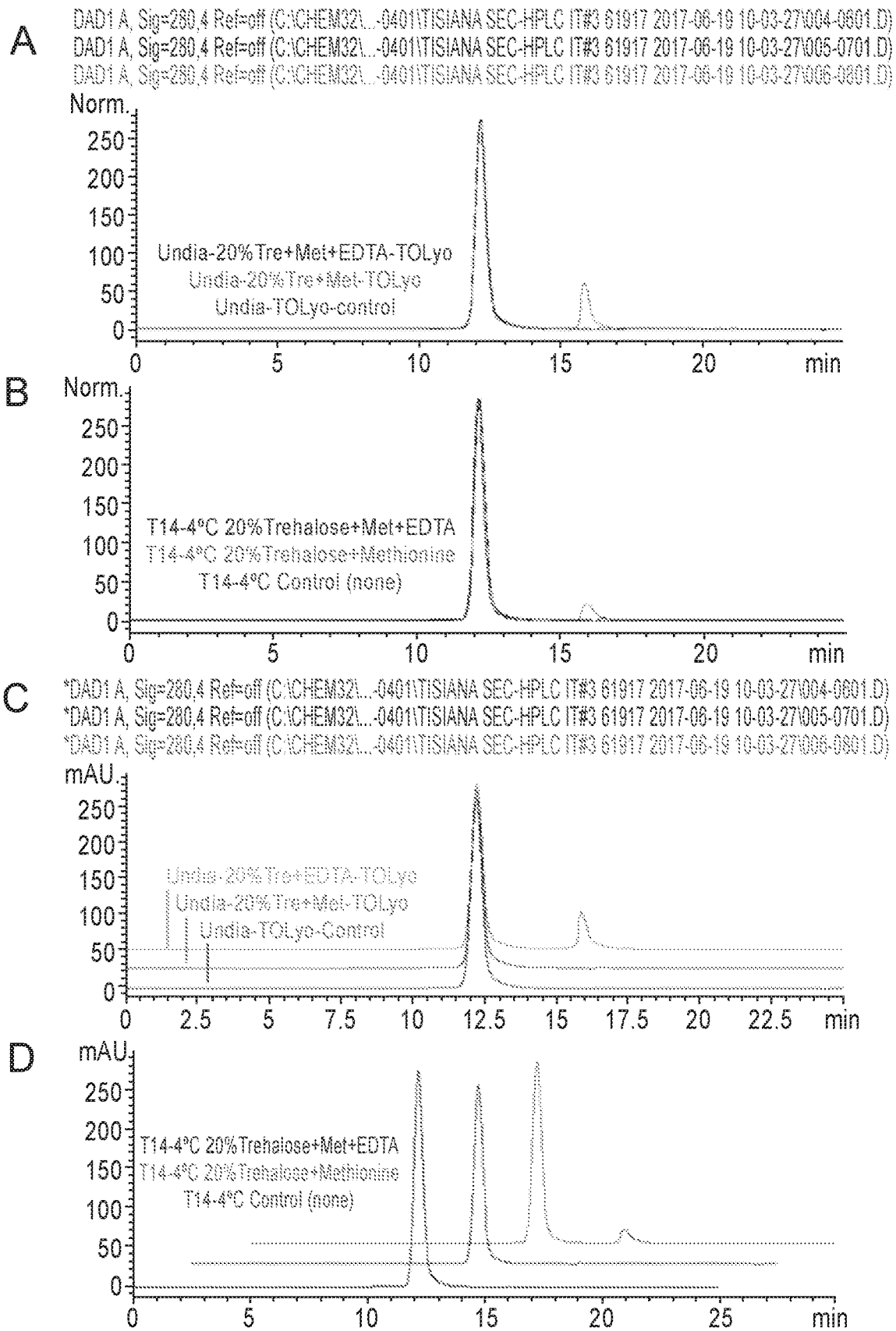
FIG. 24 A-D are a series of chromatographs showing the purity of the foralumab lead formulations after lyophilization. Both lead formulations showed >98% purity (SEC-HPLC) following lyophilization.
Figure 25:
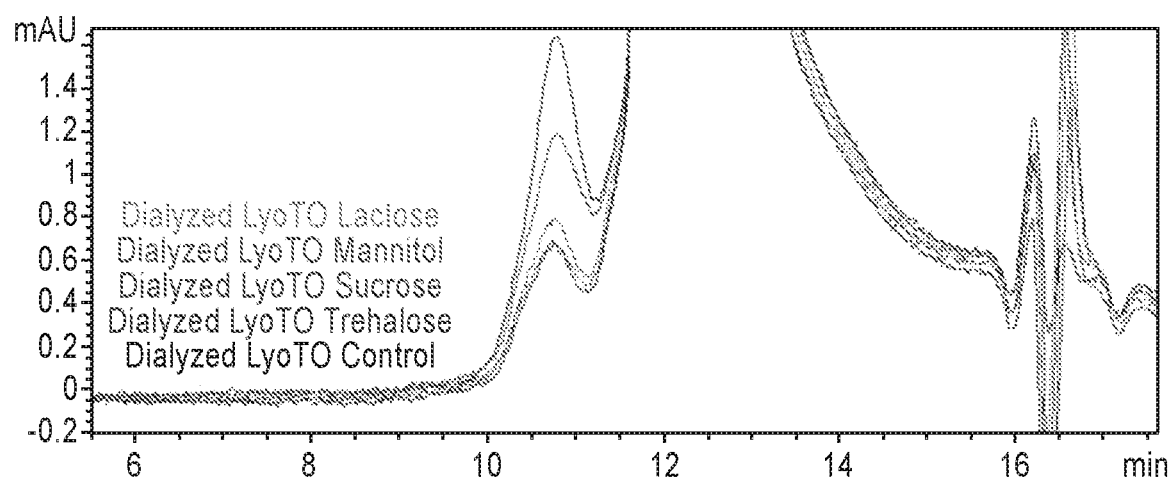
FIG. 25 is a chromatograph showing SEC-HPLC of the unformulated foralumab showing higher degradation of main peak into impurities seen in the control and mannitol formulations.
Figure 26:
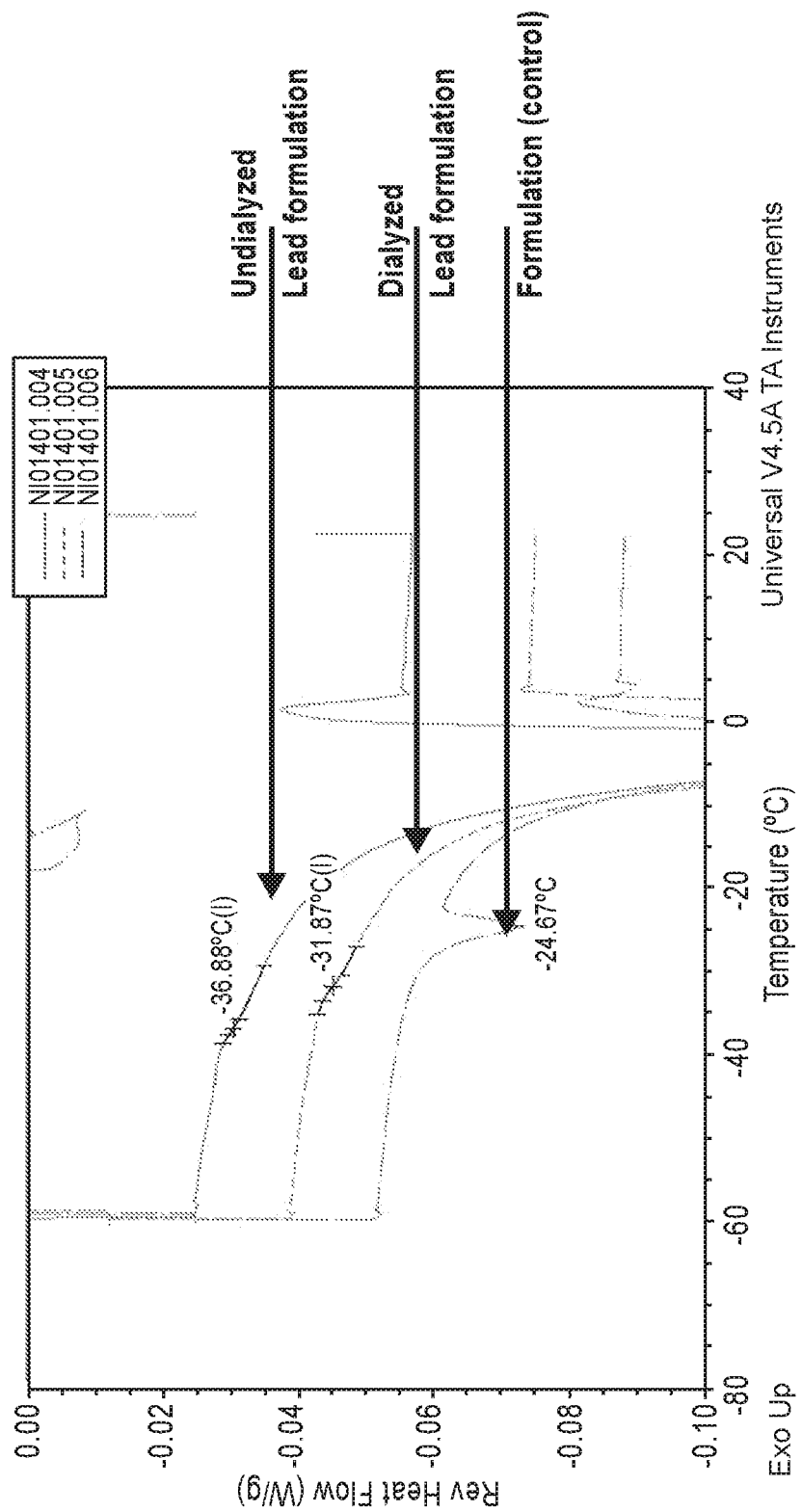
FIG. 26 is a graph showing glass transition temperature of the lead formulation compared to the control formulation (buffer). Glass transition temperature of –30-37° C. prevented collapse of the lyophilized cake. MDSC (modulated differential scanning calorimetry) analysis of NI-0401 lead formulations following the lyophilization process. MDSC analysis at different annealing temperatures. Melting, freezing and glass transition temperatures indicate that the lead formulation has minimal collapse of the lyophilized cake since they are above the glass transition temperatures.
Figure 27:
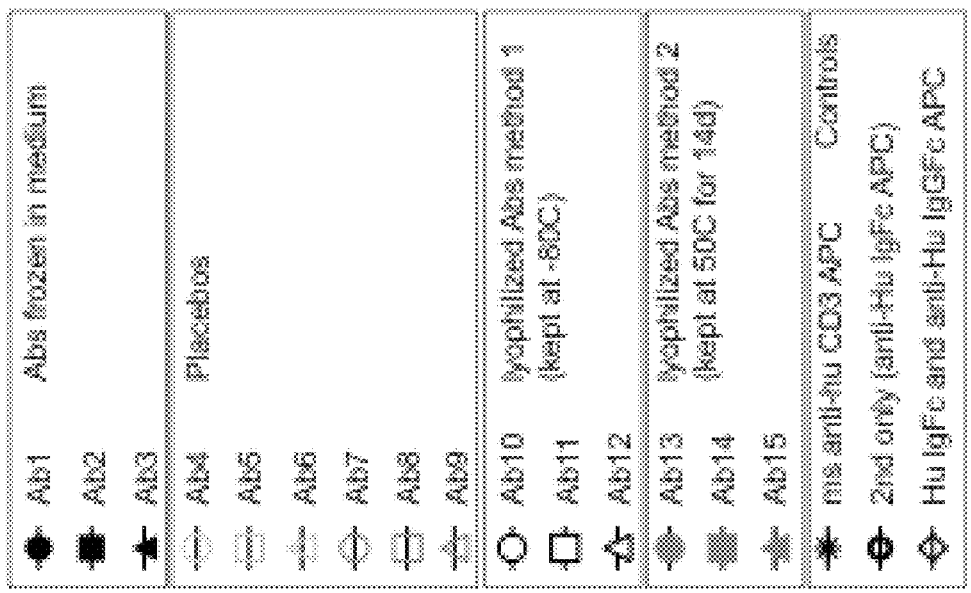
FIG. 27 is a legend key for FIG. 28.
Figure 28:
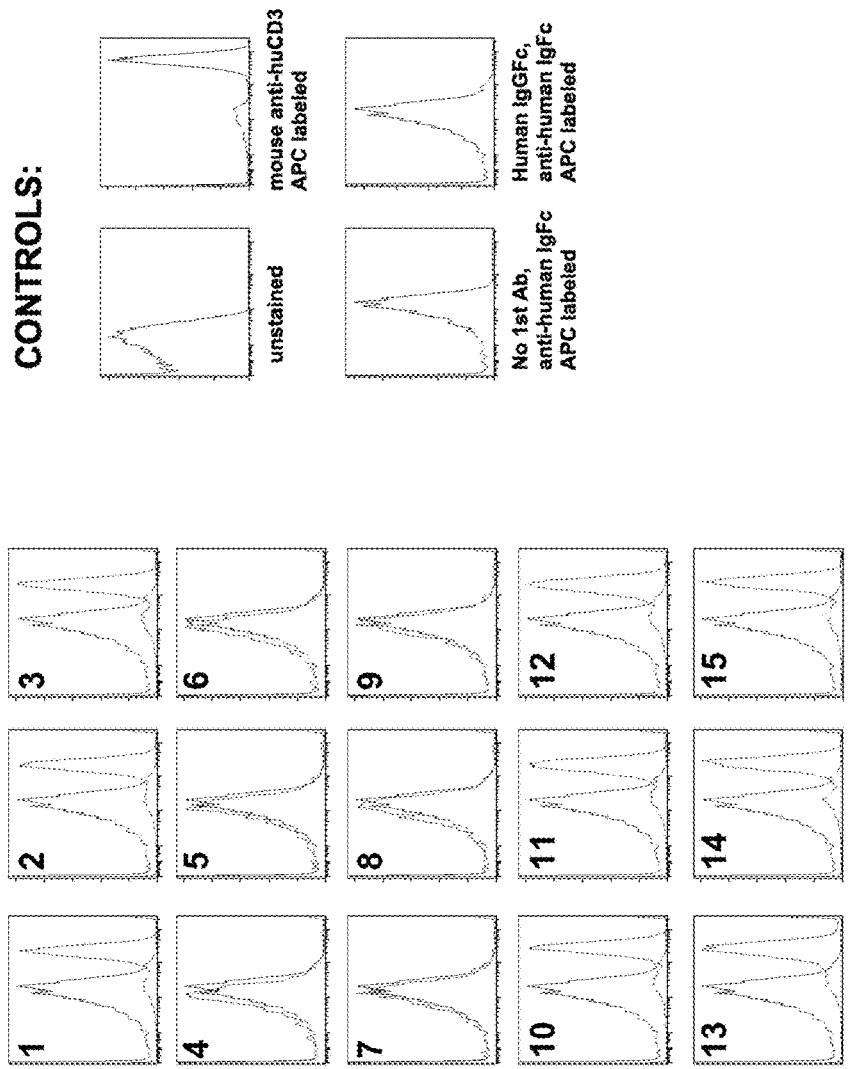
FIG. 28 is a series of graphs showing PBMCs were stained with different formulations of NI-0401 or placebo controls.
Figure 29:
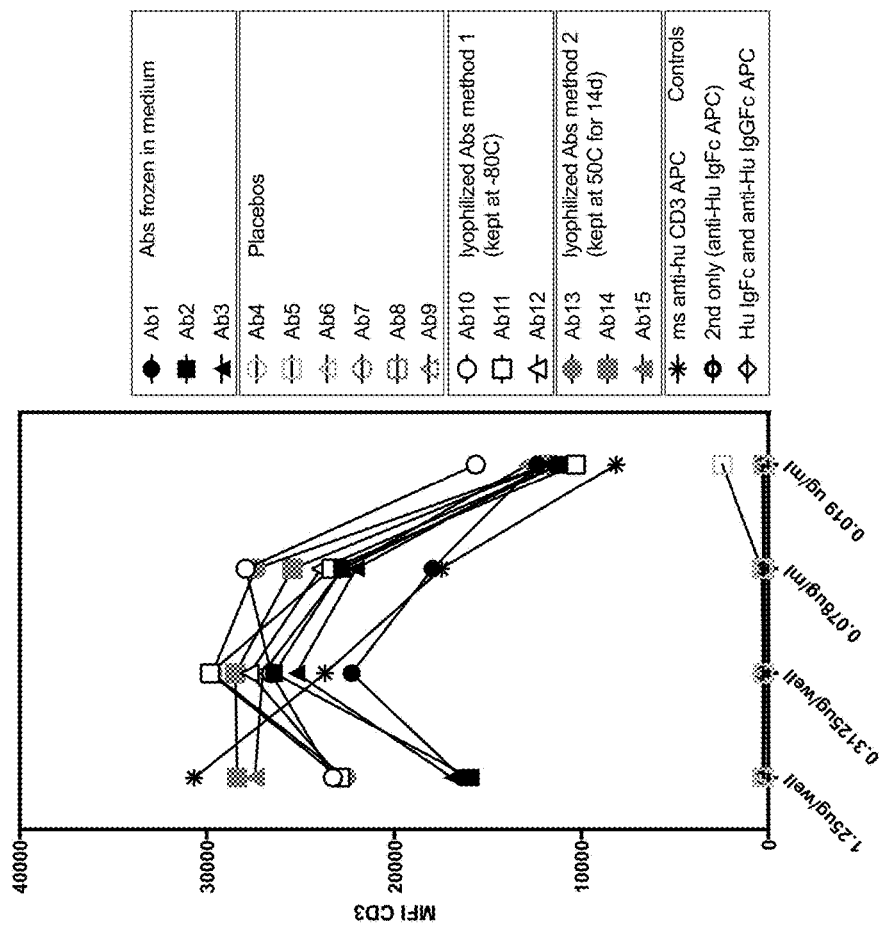
FIG. 29 is a line graph showing serial fourfold dilutions do not indicate marked differences in binding of NI-0401 reagents 1-15.
Figure 30:
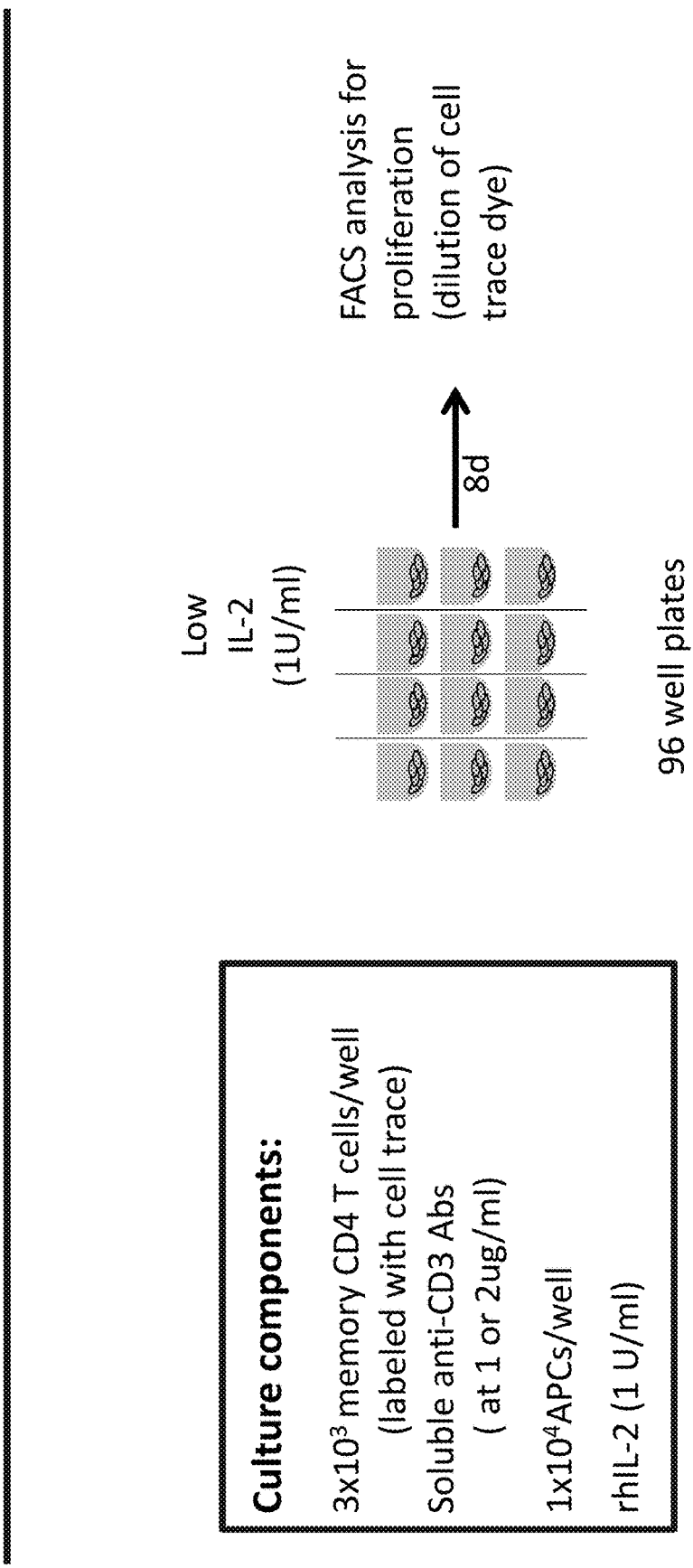
FIG. 30 shows stimulation protocol to test function of different formulations of NI-0401.
Figure 31:
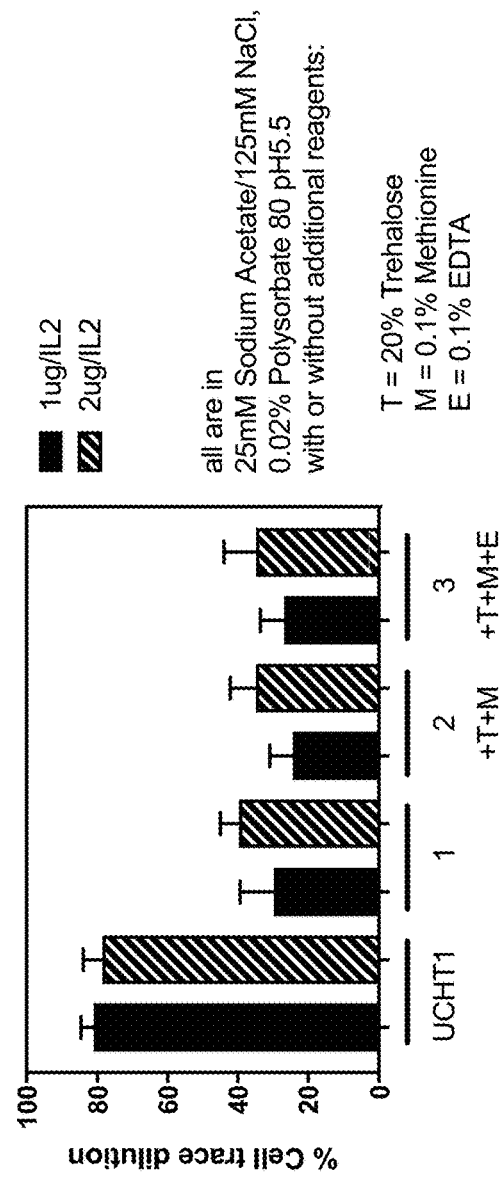
FIG. 31 show different frozen formulations of NI-0401 induce similar levels of proliferation FIG. 32 A-C is a series of bar graphs showing antibodies Lyophilized with storage at –80° C. or 50° C. show differential stimulatory capacity.
Figure 32:
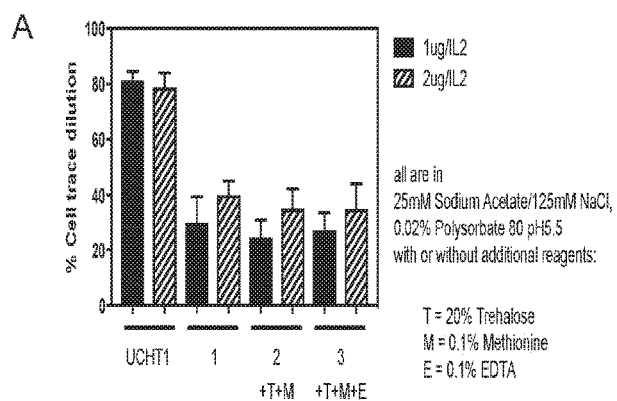
Figure 32:
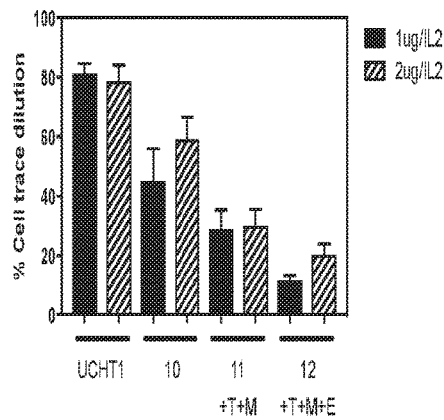
Figure 32:
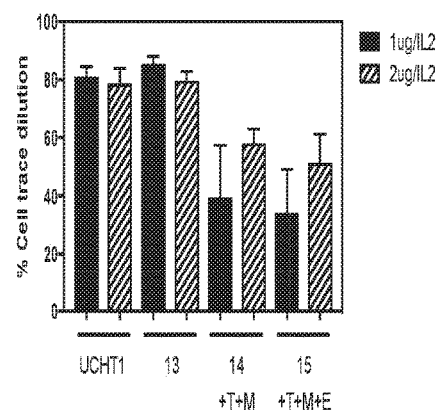
Figure 33:
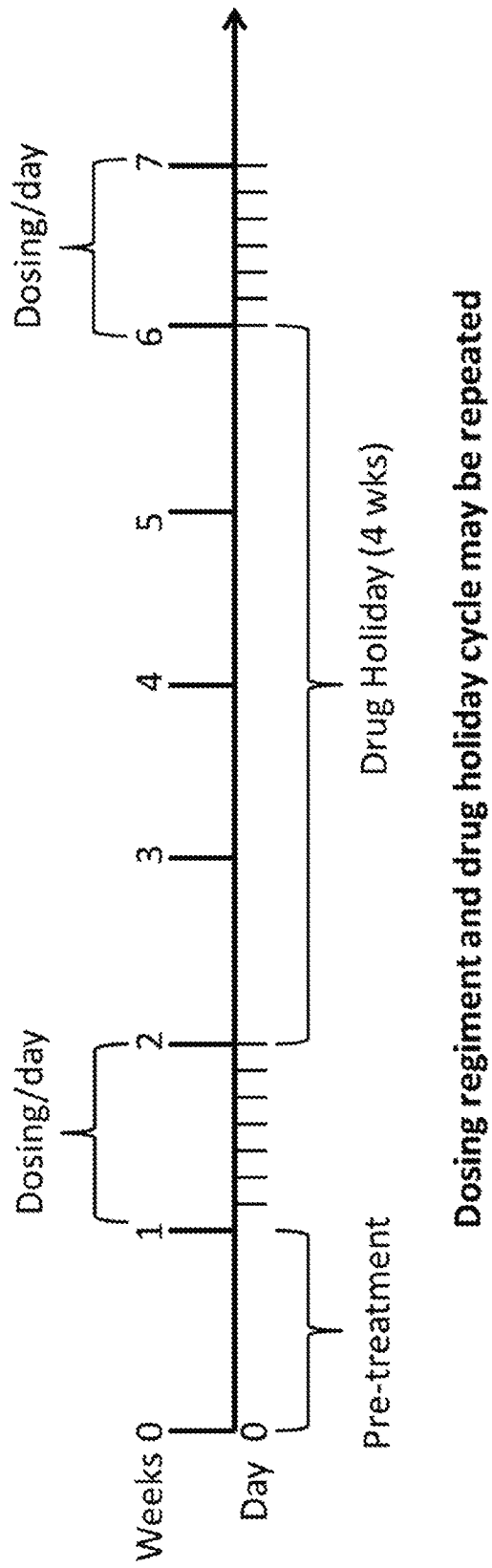
FIG. 33 is a schematic representation of a dosing regimen and drug holiday cycle for a nasal anti-CD3 antibody formulation of the present disclosure.

The lead T0 and T14 formulations were analyzed by CIEF, in order to understand the heterogeneity of NI0410 formulations. To qualitatively confirm the pI of NI-0401, cIEF was utilized and a typical profile of NI0401 is shown below (FIG. 13), with a heterogenous population of current formulation NI-0401 sample showing basic peaks (pI between >9.27-9.45), acidic peaks (compared to main peak pI between <9.3-8.60) and main peak population (pI between ~9.25-9.37). The data was analyzed based on the pI of acidic, basic and main peak population of NI-0401 sample in different formulations. Capillary isoelectric reveals that there are no significant differences in the pI of main peak, basic peak and relative acidic peak population compared to main peak of NI-0401 among lead formulations after keeping the formulations at either 4° C. or 50° C. for 14 days. However, in the control or current formulation at T14-50° C., main peak ratio is decreased and relative acid peak ratio is increased suggesting deamidation (FIG. 15). This increase in deamidation in the control/current formulation may be due to increase in pH (from ~5.5 to 7.5) of the formulation after lyophilization.

CONCLUSIONS

The analysis studies on lead formulations confirm stability of both the lead formulations i.e. NI-0401 in 25 mM sodium acetate pH 5.5, 125 mM sodium chloride, 0.02% (w/v) Polysorbate 80 buffer containing, 20% Trehalose, 0.1% Methionine; and NI-0401 in 25 mM sodium acetate pH 5.5, 125 mM sodium chloride, 0.02% (w/v) Polysorbate 80 buffer containing, 20% Trehalose, 0.1% Methionine, 0.1% EDTA.

SEC analysis showed high % purity and low % impurity for lead formulations containing 10% Trehalose with Met+/−EDTA T0 and T14 compared to current formulations. The % main peak recovery of lead formulations was >97% compared to control formulation at T0&T14.

Non-reduced and reduced gel analysis on lead formulations showed formulation containing 10% Trehalose with Met+/−EDTA had the highest protein purity. Control formulation showed more % impurities.

No significant difference in protein concentration of formulations was observed at either T0 or after T14 except for the current formulation at T14 50° C.

The pH of the current formulation changed from 5.5 to 7.5, the lead formulations pH changed from 5.5 to 5.9.

No change in Osmolality or % moisture content observed at T0& T14 with all formulations.

IEF-gel analysis for the NI0401 control formulation (T0-Lyo) showed a pI of >9.25 and the sample retained near the well of gel without clear separation.

cIEF analysis showed no significant differences among pI of main peak, basic peak and relative acidic populations of NI-0401 sample in lead formulations at T0 & T14.

cIEF analysis showed a change in the NI-0401 current formulation at T14-50C, where main peak ratio is decreased and relative acid peak ratio is increased suggesting deamidation of control formulation at T14-50C.

Summary

Based on the cumulative data from excipient screening with bulking agents and stabilizers, and stability profiles, the final lead formulations for developing the oral lyophilization dose for NI-0401/CD3 antibody are:

NI-0401 in 25 mM sodium acetate pH 5.5, 125 mM sodium chloride, 0.02% (w/v) Polysorbate 80 buffer containing 20% Trehalose, 0.1% Methionine, and NI-0401 in 25 mM sodium acetate pH 5.5, 125 mM sodium chloride, 0.02% (w/v) Polysorbate 80 buffer containing, 20% Trehalose, 0.1% Methionine, and 0.1% EDTA.

Example 7: Evaluation of Anti-CD3 Formulation in the Short Term Treatment of Primary Biliary Cirrhosis (PBC) and in the Long Term Treatment of Nonalcoholic Steatohepatitis (NASH)

The studies presented herein are designed to evaluate the use of an anti-CD3 formulation in the short term treatment of primary biliary cirrhosis (PBC) and in the long term treatment of nonalcoholic steatohepatitis (NASH).

In these studies, an anti-CD3 formulation will be administered orally, once a day for 7 days followed by drug holiday repeat cycle. The study will include 21 patients, 7 of which will receive a placebo, and 14 of which will receive the oral anti-CD3 antibody formulation at a dosage of 5 mg/day. In these studies, healthy volunteers will receive the following doses: 0.5 mg, 1.0 mg, 2.5 mg, 5 mg, 10 mg once a day for 7 days to determine the safe dose. The dosing regimen will continue for 8-12 weeks, with the following interim analysis for immunological biomarkers and/or clinical endpoints for PBC. The dosing regimen will continue with repeated cycles of ON and OFF dosing. In these studies, the oral anti-CD3 antibody formulation may be combined with adjuvants or ATRA or anti-inflammatory agent or other suitable second agent. In the studies, obeticholic acid may be administered separately from the oral anti-CD3 antibody.

TABLE 1

Temperature and pressure parameters of lyophilization for iteration# 1 formulations

| Step | Temperature | Temperature Ramp (° C./min) | Hold in hrs | Pressure |
|---|---|---|---|---|
| Loading | Ambient | N/A | N/A | NA |
| Freeze | −50° C. | 1° C./min. | 2 | NA |
| Primary Drying | −30° C. | 1° C./min | 11.8 | 75 mTorr |
| Secondary Drying | +20° C. | 1° C./min | 5.6 | 75 mTorr |

TABLE 2

Temperature and pressure parameters of lyophilization for iteration# 2 formulations

| Step | Temperature | Temperature Ramp (° C./min) | Hold in hrs | Pressure |
|---|---|---|---|---|
| Loading | Ambient | N/A | N/A | NA |
| Freeze | −50° C. | 1° C./min. | 2 | NA |
| Primary Drying | −30° C. | 1° C./min | 15 | 75 mTorr |
| Secondary Drying | +20° C. | 1° C./min | 5.0 | 75 mTorr |

TABLE 3

Temperature and pressure parameters of lyophilization for iteration# 3 formulations

| Step | Temperature | Temperature Ramp (° C./min) | Hold in hrs | Pressure |
|---|---|---|---|---|
| Loading | Ambient | N/A | N/A | NA |
| Freeze | −50° C. | 1° C./min. | 4 | NA |
| Primary Drying | −32° C. | 1° C./min | 60 hrs | 70 mTor |
| Secondary Drying | +20° C. | 1° C./min | 8 hrs | 70 mTorr |

TABLE 4

Feasibility Assessment of lyophilizing un-dialyzed/dialyzed NI-0401: Formulations with Bulking agents

| Formulation # | Formulation type | Carbohydrates/bulking agents | Abbreviations |
|---|---|---|---|
| 1 | Undialyzed NI-0401 in 25 mM sodium acetate/ 125 mM NaCl/ 0.02% W/V Polysorbate | Control (none) | Undia-liquid/lyo-none |
| 2 | | 10% Trehalose | Undia-liquid/lyo-Tre |
| 3 | | 10% Sucrose | Undia-liquid/lyo-Suc |
| 4 | | 5% Mannitol | Undia-liquid/lyo-Man |
| 5 | | 5% Lactose | Undia-liquid/lyo-Lac |
| 6 | Dialyzed NI-0401 in 25 mM sodium acetate/0.02% W/V Polysorbate | Control (none) | Dia-liquid/lyo-none |
| 7 | | 10% Trehalose | Dia-liquid/lyo-Tre |
| 8 | | 10% Sucrose | Dia-liquid/lyo-Suc |
| 9 | | 5% Mannitol | Dia-liquid/lyo-Man |
| 10 | | 5% Lactose | Dia-liquid/lyo-Lac |

TABLE 5

Effect of bulking agents on stability of NI-0401 liquid formulations at T0&T12: Appearance cake, reconstitution time, A280 and SEC-HPLC. Iteration #1 Lyo formulations Stability Results

| | | Time Point T0 Lyo Formulation No: | | | | |
|---|---|---|---|---|---|---|
| | | 1 | 2 | 3 | 4 | 5 |
| | | Formulation Type | | | | |
| | | None | 10% Tre | 10% Suc | 5% Man | 5% Lac |
| Cake appearance | Undia | White; Crystalline | White; Amorphous | White; Amorphous | White; Amorphous | White; Amorphous |
| | Dia | White; Crystalline | White; Amorphous | White; Amorphous | White; Amorphous | White; Amorphous |
| % collapse | Undia | 10 | 5 | 5 | 5 | 20 |
| | Dia | 30 | 5 | 5 | 5 | 20 |
| Reconstitution Time | Undia | 5 | 75 | 45 | 50 | 45 |
| | Dia | 5 | 85 | 90 | 75 | 75 |
| Liquid appearance | Undia | clear | clear | clear | clear | cloudy |
| | Dia | clear | clear | clear | cloudy | clear |
| Conc. (mg/mL) | Undia | 5.9 | 5.62 | 5.5 | 5.7 | 5.83 |
| | Dia | 5.98 | 5.47 | 5.5 | 5.88 | 5.9 |
| SEC-HPLC | Undia | % Purity | 99.1 | 99.9 | 99.8 | 99.4 | 99.6 |

TABLE 5-continued

Effect of bulking agents on stability of NI-0401 liquid formulations at T0&T12: Appearance cake, reconstitution time, A280 and SEC-HPLC. Iteration #1 Lyo formulations Stability Results

|  |  |  | | | | | |
|---|---|---|---|---|---|---|---|
|  |  | % Impurity | 0.93 | 0.1 | 0.2 | 0.6 | 0.4 |
|  | Dia | % Purity | 99.1 | 99.5 | 99.7 | 99.47 | 99.6 |
|  |  | % Impurity | 0.9 | 0.5 | 0.3 | 0.53 | 0.4 |

| | | Time Point T12 Lyo Formulation No: | | | | | |
|---|---|---|---|---|---|---|---|
| | | | 1 | 2 | 3 | 4 | 5 |
| | | | | | Formulation Type | | |
| | | | None | 10% Tre | 10% Suc | 5% Man | 5% Lac |
| Cake appearance | Undia | | White; Crystalline | White; Amorphous | White; Amorphous | White; Amorphous | White; Amorphous |
| | Dia | | White; Crystalline | White; Amorphous | White; Amorphous | White; Amorphous | White; Amorphous |
| % collapse | Undia | | 10 | 5 | 5 | 5 | 20 |
| | Dia | | 30 | 5 | 5 | 5 | 20 |
| Reconstitution Time | Undia | | 10 | 15 | 185 | *partially soluble | 25 |
| | Dia | | 20 | 25 | 185 | 55 | 20 |
| Liquid appearance | Undia | | clear | clear | clear | cloudy | clear |
| | Dia | | clear | clear | clear | clear | cloudy |
| Conc. (mg/mL) | Undia | | 6.1 | 5.62 | 5.84 | 4.4* | 5.45 |
| | Dia | | 6.12 | 5.45 | 5.82 | 5.81 | 5.78 |
| SEC-HPLC | Undia | % Purity | 94.64 | 99.67 | 98.84 | 72.24 | 99.01 |
| | | % Impurity | 5.36 | 0.33 | 1.16 | 27.76 | 0.99 |
| | Dia | % Purity | 82.76 | 99.47 | 75.9 | 82.45 | 99.35 |
| | | % Impurity | 17.24 | 0.53 | 24.1 | 17.55 | 0.65 |

*The formulation with mannitol showed less solubility after lyophilization.

TABLE 6

Effect of bulking agents on the stability of NI-0401 liquid formulations at T0&T12: cake appearance, cake reconstitution time, A280 and SEC-HPLC Iteration #1 liquid formulations Stability Results

| | | | Time Point | | | | | | | | | |
|---|---|---|---|---|---|---|---|---|---|---|---|---|
| | | | T0 Liquid | | | | | T12 liquid | | | | |
| | | | Formulation No: | | | | | | | | | |
| | | | 1 | 2 | 3 | 4 | 5 | 1 | 2 | 3 | 4 | 5 |
| | | | | | | | Formulation Type | | | | | |
| | | | None | 10% Tre | 10% Suc | 5% Man | 5% Lac | None | 10% Tre | 10% Suc | 5% Man | 5% Lac |
| liquid appearance | Undia | | clear | clear | clear | clear | clear | clear | clear | clear | clear | clear |
| | Dia | | clear | clear | clear | clear | clear | clear | clear | clear | clear | clear |
| Conc. (mg/mL) | Undia | | 5.74 | 5.59 | 5.56 | 5.87 | 5.77 | 6.14 | 5.74 | 5.71 | 5.91 | 5.94 |
| | Dia | | 5.9 | 5.81 | 5.62 | 5.8 | 5.78 | 6.1 | 5.65 | 5.7 | 5.91 | 5.98 |
| SEC-HPLC | Undia | % Purity | 99.7 | 99.7 | 99.68 | 99.7 | 99.68 | 96.96 | 96.38 | 96.95 | 96.16 | 94.5 |
| | | % Impurity | 0.3 | 0.3 | 0.32 | 0.3 | 0.32 | 3.04 | 3.612 | 3.045 | 3.84 | 5.5 |
| | Dia | % Purity | 99.57 | 99.57 | 99.59 | 99.68 | 99.69 | 91.25 | 91.08 | 93.12 | 94.8 | 78.64 |
| | | % Impurity | 0.43 | 0.43 | 0.41 | 0.32 | 0.31 | 8.75 | 8.92 | 6.88 | 5.2 | 21.36 |

TABLE 7

Iteration#2 Formulations: Screening with Stabilizers.

| Formulation # | Formulation type | bulking agent | Stabilizers | Abbreviations |
|---|---|---|---|---|
| 1 | Undialyzed NI-0401 in 25 mM sodium acetate/125 mM NaCl/0.02% W/V Polysorbate | 10% Trehalose | None | Undia-liq/lyo Tre-none |
| 2 | | 10% Trehalose | 0.1% Methionine | Undia-liq/lyo Tre-Met |
| 3 | | 10% Trehalose | 5% Arginine | Undia-liq/lyo Tre-Arg |
| 4 | | 10% Trehalose | 1% sod. Ascorbate | Undia-liq/lyo Tre-Sod.Asc. |
| 5 | | 20% Trehalose | 0.1% EDTA | Undia-liq/lyo Tre-EDTA |
| 6 | Dialyzed NI-0401 in 25 mM sodium acetate/0.02% W/V Polysorbate | 10% Trehalose | None | Dia-liq/lyo-Tre-none |
| 7 | | 10% Trehalose | 0.1% Methionine | Dia-liq/lyo-Tre-Met |
| 8 | | 10% Trehalose | 5% Arginine | Dia-liq/lyo-Tre-Arg |
| 9 | | 10% Trehalose | 1% sod. Ascorbate | Dia-liq/lyo-Tre-Sod.Asc. |
| 10 | | 20% Trehalose | 0.1% EDTA | Dia-liq/lyo-EDTA |

TABLE 8

Effect of stabilizers on NI-0401 Lyo formulations at T0&T14: cake appearance, cake reconstitution time, A280 & SEC-HPLC.
Iteration #2 Lyo formulations Stability Results

| | | | | T0 Lyo | | | | | T12 Lyo | | | | |
|---|---|---|---|---|---|---|---|---|---|---|---|---|---|
| | | | 1 | 2 | 3 | 4 | 5 | 1 | 2 | 3 | 4 | 5 |
| | | | Tre-None | Tre-Met | Tre-Arg | Tre-Sod.Asco. | Tre-EDTA | Tre-None | Tre-Met | Tre-Arg | Tre-Sod.Asco. | Tre-EDTA |
| Cake appearance | Undia | | White; Amorphous | White; Amorphous | White; Amorphous | White; Amorphous | White; Amorphous | White; Amorphous | White; Amorphous | White; Amorphous | White; Amorphous | White; Amorphous |
| | Dia | | White; Amorphous | White; Amorphous | White; Amorphous | White; Amorphous | White; Amorphous | White; Amorphous | White; Amorphous | White; Amorphous | White; Amorphous | White; Amorphous |
| % collapse | Undia | | 10 | 10 | 90 | 10 | 10 | 20-30 | 20-30 | 80-90 | 80-90 | 10 |
| | Dia | | 10 | 20 | 30 | 20 | 20 | 5-10 | 5-10 | 40-50 | 5-10 | 10-15 |
| Reconstitution Time | Undia | | 15 | 35 | 50 | 75 | 58 | 15 | 12 | >300 | 150 | 50 |
| | Dia | | 30 | 35 | 55 | 20 | 45 | 22 | 15 | 10 | 20 | 20 |
| Liquid appearance | Undia | | Clear | clear | cloudy | clear | clear | clear | clear | cloudy | clear | clear |
| | Dia | | Clear | clear | cloudy | clear | clear | clear | clear | cloudy | clear | clear |
| Conc. (mg/mL) | Undia | | 5.2 | 5.2 | 1.13* | 374* | 4.67 | 5.4 | 5.4 | 1.052 (*) | 357.6 (#) | 4.77 |
| | Dia | | 5.35 | 5.36 | 4.24* | 338* | 4.68 | 5.67 | 5.52 | 4.208 (*) | 264.35 (#) | 4.72 |
| SEC-HPLC | Undia | % Purity | 99.26 | 99.45 | 26.38 | 99.87 | 99.86 | 98.8 | 99.9 | 48 | 96.8 | 99.3 |
| | | % Impurity | 0.74 | 0.55 | 73.62 | 0.13 | 0.14 | 1.2 | 0.1 | 52 | 3.2 | 0.7 |
| | Dia | % Purity | 99.87 | 99.8 | 97.47 | 100 | 99.5 | 99.59 | 100 | 62.77 | 100 | 100 |
| | | % Impurity | 0.13 | 0.2 | 2.53 | 0 | 0.5 | 0.41 | 0 | 37.23 | 0 | 0 |

TABLE 9

Effect of bulking agents on stability of NI-0401 liquid formulations at T0&T12: cake appearance, cake reconstitution time, A280 & SEC-HPLC
Iteration #2 liquid formulations Stability Results

|  |  |  | Time Point |  |  |  |  |  |  |  |  |
|---|---|---|---|---|---|---|---|---|---|---|---|
|  |  |  | T0 Liquid |  |  |  |  | T14 liquid |  |  |  |
|  |  |  | Formulation No: |  |  |  |  |  |  |  |  |
|  |  |  | 1 | 2 | 3 | 4 | 5 | 1 | 2 | 3 | 4 | 5 |
|  |  |  | Formulation Type |  |  |  |  |  |  |  |  |
|  |  |  | Tre-None | Tre-Met | Tre-Arg | Tre-Sod.Asco. | Tre-EDTA | Tre-None | Tre-Met | Tre-Arg | Tre-Sod.Asco. | Tre-EDTA |
| Conc. (mg/mL) | Undia |  | 5.3 | 5.3 | 2.3* | 379 (#) | 4.6 | 5.6 | 5.4 | 0.71 (*) | 12.4 (*#) | 4.7 |
|  | Dia |  | 5.4 | 5.3 | 4.2* | 338 (#) | 4.4 | 5.6 | 5.6 | 4.6 (*) | 10.4 (*#) | 4.7 |
| Liquid appearance | Undia |  | Clear | Clear | Cloudy* | clear | Clear | Clear | Clear | Cloudy* | Yellow* | Clear |
|  | Dia |  | Clear | Clear | Cloudy* | clear | Clear | Clear | Clear | Cloudy* | Yellow* | Clear |
| SEC-HPLC | Undia | % Purity | 99.37 | 99.49 | 85.5 | 100 | 99.13 | 96.1 | 98.2 | 35 | 98.53 | 96.8 |
|  |  | % Impurity | 0.63 | 0.51 | 14.5 | 0 | 0.87 | 3.9 | 1.8 | 65 | 1.47 | 3.2 |
|  | Dia | % Purity | 100 | 99.69 | 96.9 | 100 | 99.2 | 97.78 | 98.78 | 81.9 | 99.4 | 98.5 |
|  |  | % Impurity | 0 | 0.31 | 3.1 | 0 | 0.8 | 2.22 | 1.22 | 18.1 | 0.6 | 1.5 |

*Formulation precipitated;
(#) Sod. Ascorbate interfered with A280 Assay.

TABLE 10

% purity and impurity of undialyzed/Dialyzed Lyo formulations at T0&T14 on a Non-reducing gel & Reducing Gel

|  |  | Non-reduced gel | | | | Reduced gel | | | |
|---|---|---|---|---|---|---|---|---|---|
|  |  | T0 | | T14 | | T0 | | T14 | |
| Formulations | | % impurity | % purity | % impurity | % purity | % impurity | % purity | % impurity | % purity |
| UnDialyzed Lyo Formulation | Tre-none | 0.08 | 99.92 | 0.04 | 99.96 | 4.75 | 95.25 | 4.28 | 95.72 |
|  | Tre-Methionine | 0.01 | 99.99 | 0.03 | 99.97 | 4.29 | 95.71 | 4.18 | 95.82 |
|  | Tre-Arginine | 5.97 | 94.03 | 0.55 | 99.45 | 10.41 | 89.59 | 5.63 | 94.37 |
|  | Tre-Sod.Asco | 0.19 | 99.81 | 1.09 | 98.91 | 3.42 | 96.58 | 7.29 | 92.71 |
|  | Tre-EDTA | 0.07 | 99.93 | 0.27 | 99.73 | 3.74 | 96.26 | 3.76 | 96.24 |
| Dialyzed Lyo Formulation | Tre-none | 0.87 | 99.13 | 1.40 | 98.60 | 3.09 | 96.91 | 3.28 | 96.72 |
|  | Tre-Methionine | 0.84 | 99.16 | 0.68 | 99.32 | 3.10 | 96.90 | 3.26 | 96.74 |
|  | Tre-Arginine | 4.82 | 95.18 | 5.10 | 94.90 | 5.64 | 94.36 | 5.82 | 94.18 |
|  | Tre-Sod.Asco | 4.30 | 95.70 | 3.49 | 96.51 | 2.26 | 97.74 | 2.53 | 97.47 |
|  | Tre-EDTA | 0.48 | 99.42 | 0.80 | 99.20 | 1.85 | 98.15 | 2.01 | 97.99 |

TABLE 11

Iteration#2: Lead NI-0401 formulations for MDSC analysis.

| Formulation # | Formulation type | bulking agent | Stabilizers | Abbreviations |
|---|---|---|---|---|
| 1 | Undialyzed NI-0401 | None | None | Undialyzed-None (Control) |
| 2 | in 25 mM sodium acetate/125 mM NaCl/0.02% W/V Polysorbate | 10% Trehalose | 0.1% Methionine | Undia-Tre-Met (lead formulation) |
| 3 | Dialyzed NI-0401 in 25 mM sodium acetate/0.02% W/V Polysorbate | 10% Trehalose | 0.1% Methionine | Dia-liq Tre-Met (lead formulation) |
| 4 | Undialyzed NI-0401 | 20% Trehalose | 0.1% Methionine | Undia-20% Tre-Met |

TABLE 11-continued

Iteration#2: Lead NI-0401 formulations for MDSC analysis.

| Formulation # | Formulation type | bulking agent | Stabilizers | Abbreviations |
|---|---|---|---|---|
| 5 | in 25 mM sodium acetate/125 mM NaCl/0.02% W/V Polysorbate | 20% Trehalose | 0.1% EDTA | Undia-20% Tre-EDTA |
| 6 | | 20% Trehalose | 0.1% Methionine + 0.1% EDTA | Undia-20% Tre-Met-EDTA |

TABLE 12

Freezing temperature, melting temperature and formulation glass transition temperature (tg) of undialyzed/dialyzed lead formulation and current formulation.

| | MDSC results of liquid formulations | | | | |
|---|---|---|---|---|---|
| Liquid Formulations | Annealing temp (° C.) | Freezing temp (° C.) | Melting temp (° C.) | $T_g$ (° C.) | Eutectic point (° C.) |
| Undialyzed current formulation (Control) | N/A | −11.01 | −1.02 | — | −24.67 |
| Undialyzed NI0401 lead formulation; 10% Trehalose; 0.1% methionine (Undia-Lead) | N/A | −14.13 | −1.52 | −36.88 | — |
| Dialyzed NI0401; 10% Trehalose; 0.1% methionine (Dia-lead) | N/A | −8.06 | −0.49 | −31.87 | — |
| Undialyzed NI0401 lead formulation; 10% Trehalose; 0.1% methionine (Undia-Lead) | −22 | −10.08 | 1.78 | −36.87 | — |
| | −24 | 14.85 | 1.79 | −37.65 | — |
| | −26 | −15.26 | 1.95 | −37.44 | — |
| Undialyzed NI0401 lead formulation; 10% Trehalose; 0.1% methionine (Undia-Lead-10% Tre + Met) | N/A | −14.13 | −1.52 | −36.87 | — |
| Undialyzed NI0401 lead formulation; 20% Trehalose; 0.1% methionine (Undia-Lead-20% Tre + Met) | N/A | −12.49 | −2.60 | −34.69 | — |
| Undialyzed NI0401 lead formulation; 20% Trehalose; 0.1% EDTA (Undia-Lead-20% Tre + EDTA) | N/A | −9.17 | −2.68 | −34.69 | — |
| Undialyzed NI0401 lead formulation 20% Trehalose 0.1% Methionine and 0.1% EDTA (Undia-Lead-20% Tre + Met + EDTA) | N/A | −13.11 | −2.50 | −34.66 | — |

TABLE 13

Iteration#3 NI-0401 Lead Formulations.

Lyo Formulations with NI-0401

| Formulation# | Sample | bulking agent | Stabilizers | Abbreviation |
|---|---|---|---|---|
| 1 | NI-0401 | None | None | Control |
| 2 | in 25 mM sodium acetate/125 mM NaCl/0.02% W/V Polysorbate | 20% Trehalose | 0.1% Methionine | 20% Tre-Met (Met formulation) |
| 3 | | 20% Trehalose | 0.1% Methionine + 0.1% EDTA | 20% Tre-Met-EDTA (Met + EDTA formulation) |

TABLE 14

Iteration #3 Lyo formulations: summary of stability results
Iteration #3 Lyo formulations Stability Results

| | | Time Point | | | | | | | |
|---|---|---|---|---|---|---|---|---|---|
| | | T0 Lyo | | | T14-50° C. Lyo | | | T14-4° C. Lyo | |
| | | | | | Formulation No: | | | | |
| | | 1 | 2 | 3 | 1 | 2 | 3 | 1 | 2 | 3 |
| | | | | | Formulation Type | | | | |
| | | Control | Tre-Met | Tre-EDTA | Control | Tre-Met | Tre-EDTA | Control | Tre-Met | Tre-EDTA |
| Cake appearance | | White; Crystalline | White; Amorphous | White; Amorphous | White; Crystalline | White; Amorphous | White; Amorphous | White; Crystalline | White; Amorphous | White; Amorphous |
| % collapse | | 5-40% | 5-10% | 5-10% | 50-60% | 10-20% | 10-20% | 40-60% | 10-20% | 10-20% |
| Reconstitution time (sec) | | 5 | 45 | 45 | 5 | 40 | 40 | 5 | 40 | 40 |
| solution appearance | | clear | Clear | clear | cloudy | clear | clear | clear | clear | clear |
| pH | | 7.14 | 5.8 | 5.72 | 7.57 | 5.9 | 5.81 | 7.14 | 5.8 | 5.72 |
| Conc. (mg/mL) | | 6.1 | 5.5 | 5.4 | 5* | 5.7 | 5.6 | 6.2 | 5.3 | 5.4 |
| % Moisture | | 10.86* | 3.34 | 2.32 | 7.41 | 3.04 | 2.88 | N/A | N/A | N/A |
| Osmolality (mOsmo/Kg) | | 289 | 846 | 855 | 284 | 900 | 907 | 281 | 835 | 852 |
| SEC-HPLC | % Purity | 98.85 | 99.98 | 99.9 | 82.07 | 99.09 | 99.42 | 98.56 | 99.58 | 99.48 |
| | % Impurity | 1.15 | 0.02 | 0.1 | 17.93 | 0.9 | 0.57 | 1.55 | 0.42 | 0.52 |

TABLE 15

% purity and impurity of Lyo lead formulations at T0&T14 on a non-reducing gel.

| | Non-Reduced gel | | | | | |
|---|---|---|---|---|---|---|
| | T0 | | T14-50° C. | | T14-4° C. | |
| Lyo-Formulations | % purity | % impurity | % purity | % impurity | % purity | % impurity |
| Control-none | 98.3 | 1.7 | 85.2 | 12.3 | 98.3 | 1.7 |
| 20% Tre + 0.1% Met | 99.4 | 0.6 | 99.4 | 0.6 | 99.4 | 0.6 |
| 20% Tre + 0.1% Met + 0.1% EDTA | 99.4 | 0.6 | 99.3 | 0.7 | 99.7 | 0.3 |

TABLE 16

% purity and impurity of Lyo lead formulations at T0&T14 on a reducing gel.

| | Reduced gel | | | | | |
|---|---|---|---|---|---|---|
| | T0 | | T14-50° C. | | T14-4° C. | |
| Lyo formulations | % purity | % impurity | % purity | % impurity | % purity | % impurity |
| Control-none | 98.3 | 1.7 | 95.7 | 4.3 | 98.5 | 1.5 |
| 20% Tre + 0.1% Met | 98.5 | 1.5 | 98.5 | 1.5 | 98.9 | 1.1 |
| 20% Tre + 0.1% Met + 0.1% EDTA | 99.0 | 1.0 | 99.5 | 0.5 | 99.6 | 0.4 |

Other Embodiments

While the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A formulation comprising: anti-CD3 antibody comprising a heavy chain amino acid sequence comprising the amino acid sequence of SEQ ID NO: 10 and a light chain amino acid sequence comprising the amino acid sequence of SEQ ID NO: 11, sodium acetate trihydrate, sodium chloride, polysorbate 80, trehalose, and methionine.

2. The formulation of claim 1, further comprising EDTA.

3. The formulation of claim 1, wherein the formulation is a liquid.

4. The formulation of claim 1, wherein the formulation is a lyophilized powder.

5. The formulation of claim 1, comprising a unit dose of the anti-CD3 antibody.

6. The formulation of claim 5, wherein the unit dose is about 0.1 mg to 10 mg.

7. The formulation of claim 6, wherein the unit dose is 0.5 mg, 2.5 mg or 5.0 mg.

8. The formulation of claim 3, wherein the concentration of:
   a. sodium acetate trihydrate is about 10 mM to 500 mM;
   b. sodium chloride is about 10 mM to 500 mM;
   c. polysorbate 80 is about 0.01% to 1% (w/v);
   d. trehalose is about 5% to 50% (w/v); and
   e. methionine is 0.01% to 1% (w/v).

9. The formulation of claim 8, where the concentration of EDTA is about 0.01% to 1% (w/v).

10. The formulation of claim 8, wherein the solution is at a pH in the range of 4 to 6.

11. A lyophilized powder of the formulation of claim 8.

12. A liquid formulation comprising a unit dose of about 0.1 mg to 10 mg of an anti-CD3 antibody comprising a heavy chain amino acid sequence comprising the amino acid sequence of SEQ ID NO: 10 and a light chain amino acid sequence comprising the amino acid sequence of SEQ ID NO: 11, 25 mM sodium acetate trihydrate, 125 mM sodium chloride, 0.02% polysorbate 80 (w/v), 20% trehalose (w/v), and 0.1% methionine(w/v).

13. The formulation of claim 11, further comprising 0.1% EDTA (w/v).

14. The liquid formulation of claim 12, wherein the unit dose is 0.5 mg, 2.5 mg or 5.0 mg.

15. A lyophilized powder of the formulation of claim 12.

16. The formulation of claim 4, wherein the ratio of anti-CD3 antibody to:
   a. polysorbate 80 is about 1:0.01 to 0.1 (w/w);
   b. trehalose is about 1:10 to 50 (w/w);
   c. methionine about 1:0.1 to 0.5 (w/w);
   d. sodium acetate trihydrate is about 1:0.1 to 1.0 (w/w); and
   e. sodium chloride is about 1:0.5 to 2.0 (w/w).

17. The formulation of claim 16, where the ratio of anti-CD3 antibody to EDTA is about 1: 0.1 to 0.5 (w/w).

18. A powder formulation comprising a unit dose of about 0.1 mg to 10 mg of an anti-CD3 antibody comprising a heavy chain amino acid sequence comprising the amino acid sequence of SEQ ID NO: 10 and a light chain amino acid sequence comprising the amino acid sequence of SEQ ID NO: 11 and about 0.58 mg of sodium acetate trihydrate, 1.25 mg sodium chloride, 0.034 mg polysorbate 80, 34 mg trehalose and 0.17 mg methionine per 1 mg of anti-CD3 antibody.

19. The powder formulation of claim 18, further comprising 0.17 mg EDTA per 1 mg of anti-CD3 antibody comprising a heavy chain amino acid sequence comprising the amino acid sequence of SEQ ID NO: 10 and a light chain amino acid sequence comprising the amino acid sequence of SEQ ID NO: 11.

20. The powder formulation of claim 18, wherein the unit dose is 0.5 mg, 2.5 mg or 5.0 mg.

21. An enteric coated oral capsule comprising the formulation of claim 18.

22. An enteric coated oral capsule containing an anti-CD3 antibody lyophilized formulation comprising a unit dose of about 0.1 mg to 10 mg of an anti-CD3 antibody comprising a heavy chain amino acid sequence comprising the amino acid sequence of SEQ ID NO: 10 and a light chain amino acid sequence comprising the amino acid sequence of SEQ ID NO: 11 and about 0.58 mg of sodium acetate trihydrate, 1.25 mg sodium chloride, 0.034 mg polysorbate 80, 34 mg trehalose and 0.17 mg methionine per 1 mg of anti-CD3 antibody.

23. The enteric-coated oral capsule of claim 22, wherein the anti-CD3 antibody lyophilized formulation further comprises 0.17 mg EDTA per 1 mg of anti-CD3 antibody.

24. The enteric-coated oral capsule of claim 22, wherein the unit dose is 0.5 mg, 2.5 mg or 5.0 mg.

25. An enteric coated oral capsule containing an anti-CD3 antibody liquid formulation comprising a unit dose of about 0.1 mg to 10 mg of an anti-CD3 antibody comprising a heavy chain amino acid sequence comprising the amino acid sequence of SEQ ID NO: 10 and a light chain amino acid sequence comprising the amino acid sequence of SEQ ID NO: 11, 25 mM sodium acetate trihydrate, 125 mM sodium chloride, 0.02% polysorbate 80 (w/v), 20% trehalose (w/v), and 0.1% methionine(w/v).

26. The enteric-coated oral capsule of claim 25, anti-CD3 antibody liquid formulation further comprises 0.1% EDTA.

27. The enteric-coated oral capsule of claim 25, wherein the unit dose is 0.5 mg, 2.5 mg or 5.0 mg.

28. The formulation of claim 1, wherein the formulation further comprises as least one additional active agent selected from the group consisting of: an NF-κB inhibitor, a GLP-1 or a beta cell resting compound, mesalamine or another 5-ASA drug, pentoxifylline, ursodeoxycholic acid, a PPARγ agonist, All Trans Retinoic Acid (ATRA), DPP-4 (gliptins-sitagliptin), a fatty acid synthesis inhibitor, a FXR agonist), fexaramine, cafestol, bile Acid Sequestrants, SGLT2 inhibitors, an anti-IL-6R mAb, an anti-TNF antibody, Etanercept, anti-inflammatory and/or immunosuppressive compounds, tacrolimus, corticosteroids, statins, interferon beta, glatiramer acetate, interferon beta-1a, interferon beta-1b, mitoxantrone, dexamethasone, methylprednisolone, prednisone, and an anti-obesity drug.

29. An enteric coated oral capsule of claim 25 containing an antibody liquid formulation comprising a unit dose of an antibody, 20% trehalose (w/v), and 0.1% methionine(w/v).

30. An enteric coated oral capsule of claim 25 containing an antibody lyophilized formulation comprising a unit dose an antibody and about 34 mg trehalose and 0.17 mg methionine per mg of antibody.

31. The enteric coated oral capsule of claim 25, wherein the antibody has an IgG1 isotype.

32. The formulation of claim 1, further comprising mannitol.

33. The formulation of claim 1, wherein the formulation is an oral formulation.

* * * * *